United States Patent
Zhao et al.

(10) Patent No.: US 8,344,160 B2
(45) Date of Patent: Jan. 1, 2013

(54) PYRROLONE MELANIN CONCENTRATING HORMONE RECEPTOR-1 ANTAGONISTS

(75) Inventors: Guohua Zhao, Princeton, NJ (US); William N. Washburn, Titusville, NJ (US); James J. Mignone, Hamilton, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 70 days.

(21) Appl. No.: 13/122,833

(22) PCT Filed: Oct. 8, 2009

(86) PCT No.: PCT/US2009/059918
§ 371 (c)(1),
(2), (4) Date: Apr. 6, 2011

(87) PCT Pub. No.: WO2010/042674
PCT Pub. Date: Apr. 15, 2010

(65) Prior Publication Data
US 2011/0195986 A1    Aug. 11, 2011

Related U.S. Application Data

(60) Provisional application No. 61/103,665, filed on Oct. 8, 2008.

(51) Int. Cl.
| C07D 487/04 | (2006.01) |
| C07D 401/04 | (2006.01) |
| C07D 239/02 | (2006.01) |
| A61K 31/505 | (2006.01) |
| A61K 31/44  | (2006.01) |
| A61K 31/4015 | (2006.01) |

(52) U.S. Cl. ............... 548/453; 546/277.1; 544/323; 514/275; 514/338; 514/414; 514/421

(58) Field of Classification Search ............ None
See application file for complete search history.

(56) References Cited

FOREIGN PATENT DOCUMENTS
| WO | WO2005/100334 A1 | 10/2005 |
| WO | WO2007/092416 A2 | 8/2007 |
| WO | WO2007/093366 A1 | 8/2007 |

OTHER PUBLICATIONS

Borowsky, B. et al., "Antidepressant, anxiolytic and anorectic effects of a melanin-concentrating hormone-1 receptor antagonist", Nature Medicine, vol. 8(8), pp. 825-830 (2002).

Kokkotou, E. et al., "Melanin-concentrating hormone as a mediator of intestinal inflammation", PNAS, vol. 105(30), pp. 10613-10618 (2008).

Kowalski, T. et al., "Melanin-concentrating hormone-1 receptor antagonism decreases feeding by reducing meal size", European Journal of Pharmacology, vol. 497, pp. 41-47 (2004).

Takekawa, S. et al., "T-226296: a novel, orally active and selective melanin-concentrating hormone receptor antagonist", European Journal of Pharmacology, vol. 438, pp. 129-135 (2002).

*Primary Examiner* — Kamal Saeed
*Assistant Examiner* — Nyeemah A Grazier
(74) *Attorney, Agent, or Firm* — Burton Rodney; Maureen S. Gibbons; Jing G. Sun

(57) ABSTRACT

The present application provides compounds, including all stereoisomers, solvates, prodrugs and pharmaceutically acceptable forms thereof according to Formula I

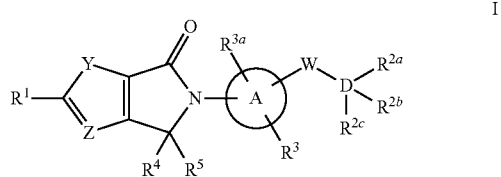

wherein $R^1$,

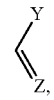

$R^4$, $R^5$,

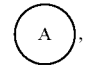

$R^3$, $R^{3a}$, W, D, $R^{2a}$, $R^{2b}$ and $R^{2c}$ are defined herein.
Additionally, the present application provides pharmaceutical compositions containing at least one compound according to Formula I and optionally at least one additional therapeutic agent. Finally, the present application provides methods for treating a patient suffering from an MCHR-1 modulated disease or disorder such as, for example, obesity, diabetes, depression, anxiety or intestinal inflammation, by administration of a therapeutically effective dose of a compound according to Formula I.

13 Claims, No Drawings

PYRROLONE MELANIN CONCENTRATING HORMONE RECEPTOR-1 ANTAGONISTS

CROSS-REFERENCE TO RELATED APPLICATIONS

The present application is a 371 application of PCT/US2009/059918 filed Oct. 8, 2009, which claims priority benefit of U.S. provisional application Ser. No. 61/103,665, filed Oct. 8, 2008, each of which is incorporated by reference herein.

FIELD OF THE INVENTION

The present invention relates to pyrrolone melanin concentrating hormone receptor-1 (MCHR1) antagonists, pharmaceutical compositions containing azolopyrrolone MCHR1 antagonists and methods of treating diabetes, obesity and related diseases employing such MCHR1 antagonists.

BACKGROUND

Several lines of pharmacological and genetic evidence support the role of Melanin Concentrating Hormone Receptor-1 (hereafter "MCHR1") as a modulator of food intake and body weight. Central administration of MCH increases food intake and body weight in both rats and mice. Chronic ICV infusion of MCH causes increased food intake and ultimately obesity in mice, while infusion of an MCH peptide antagonist blocks MCH-induced food intake and results in weight loss and decreased feeding in diet-induced obese mice.

The expression of both the MCH peptide and receptor are modulated by nutritional status. MCH mRNA is upregulated both in hyperphagic obese mice (ob/ob), and fasted animals. Targeted disruption of the gene for MCH peptide results in hypophagia and leanness. Disruption of the MCHR1 gene causes leanness, altered metabolism, and hyperlocomotion accompanied by mild hyperphagia. Conversely, over-expression of MCH peptide results in hyperphagia, obesity and diabetes. Small molecule MCHR1 antagonists have been shown to cause weight loss in rodent weight and feeding models after both oral and intraperitoneal administration; *Eur. J. Pharmacol.*, 438:129-135 (2002); *Nat. Med.*, 8:825-830 (2002); *Eur. J. Pharmacol.*, 497:41-47 (2004).

Kokkotou, E. et al., "Melanin-concentrating hormone as a mediator of intestinal inflammation", *Proc. Natl. Acad. Sci.*, 105(30):10613-10618 (Jul. 29, 2008) discloses that the intestinal melanin-concentrating hormone (MCH) and melanin-concentrating hormone receptor 1 (MCHR1) play a key role "in the pathogenesis of acute experimental colitis and possibly human IBD [inflammatory bowel disease]. We showed that MCH immunoneutralization is an effective treatment for TNBS-induced colitis . . . " (page 10616, 1st column).

DETAILED DESCRIPTION OF THE INVENTION

The present application provides compounds, including all stereoisomers, solvates, prodrugs and pharmaceutically acceptable forms thereof according to Formula I. Additionally, the present application provides pharmaceutical compositions containing at least one compound according to Formula I and optionally at least one additional therapeutic agent. Finally, the present application provides methods for treating a patient suffering from an MCHR-1 modulated disease or disorder such as, for example, obesity, diabetes, depression or anxiety by administration of a therapeutically effective dose of a compound according to Formula I.

Thus, in accordance with the present invention a compound is provided having the Formula I

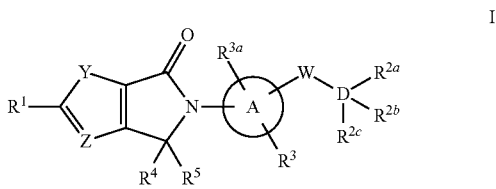

wherein:
Y is O or S;
Z is CH or N;

is selected from the group consisting of phenyl and monocyclic heteroaryl;

$R^1$ is selected from the group consisting of substituted or unsubstituted phenyl or substituted and unsubstituted monocyclic heteroaryl;

D is selected from the group consisting of a direct bond, substituted or unsubstituted $C_1$-$C_4$ alkyl, substituted or unsubstituted $C_3$-$C_7$ cycloalkyl, substituted or unsubstituted $C_3$-$C_7$-cycloalkyl-$C_1$-$C_4$-alkyl, and a 4- to 6-membered cyclic amine (also referred to as an N-containing heterocyclyl group), and an 8-membered bicyclic amine;

W is selected from the group consisting of —O— and —N($R^6$)—; or
W is a direct bond provided that

is linked to the nitrogen of a cyclic or bicyclic amine;

$R^{2a}$, $R^{2b}$ and $R^{2c}$ are the same or different and are independently selected from the group consisting of hydrogen, hydroxyl, substituted or unsubstituted $C_1$-$C_4$ alkoxy, substituted or unsubstituted $C_1$-$C_4$ alkyl, polyfluoro-$C_1$-$C_4$-alkyl, substituted or unsubstituted $C_3$-$C_7$ cycloalkyl, substituted or unsubstituted $C_3$-$C_7$ cycloalkoxy, —CN, $NR^{11}R^{11a}$, —$SO_2R^{10}$, —$CO_2R^{10}$, heterocyclyl, halo, hydroxy-$C_1$-$C_4$-alkyl, a substituted or unsubstituted 4- to 6-membered cyclic amine wherein said cyclic amine is optionally substituted with —OH, carbonylamino, alkoxycarbonylamino, or optionally at least one of $R^{2a}$, $R^{2b}$ and $R^{2c}$ is a prodrug moiety selected from an amino acid ester or a phosphoric acid ester wherein said amino acid has the formula

wherein $R^9$ is H or $C_1$-$C_4$ alkyl such as i-$C_3C_7$;
provided that when D is a direct bond, $R^{2a}$, $R^{2b}$ and $R^{2c}$ are independently selected from H, $C_1$-$C_4$ alkyl and $C_3$-$C_7$ cycloalkoxy;

or any two of $R^{2a}$, $R^{2b}$ or $R^{2c}$ may be taken together to form a ring; or where $R^{2a}$ is OH, $R^{2b}$ and $R^{2c}$ can optionally be taken together with a carbon (such as present in D) to which they are attached to fowl a $C_3$ to $C_7$ cycloalkyl ring which may be optionally substituted with one or two halogen atoms such as F, or $R^{2b}$ and $R^{2c}$ optionally can be taken together with the carbon (such as present in D) to which they are attached to form a 6-membered heterocycle which is 1,1-dioxido-tetrahydro-2H-thiopyran;

$R^3$ and $R^{3a}$ are the same or different and are independently selected from the group consisting of hydrogen, hydroxyl, substituted or unsubstituted $C_1$-$C_4$ alkoxy, halo, CN, substituted or unsubstituted $C_1$-$C_4$ alkyl, polyfluoro-$C_1$-$C_4$-alkyl, substituted or unsubstituted $C_3$-$C_7$ cycloalkyl, substituted or unsubstituted $C_3$-$C_7$ cycloalkoxy, amino, alkylamino, dialkylamino, and aminoalkyl, or $R^3$ and/or $R^{3a}$ are absent, or $R^3$ or $R^{3a}$ and D may optionally be taken together with the atoms to which they are attached to form a 5- to 7-membered ring, for example a 5- to 7-membered heterocyclyl ring;

$R^4$ and $R^5$ are the same or different and are independently selected from the group consisting of hydrogen and substituted or unsubstituted $C_3$-$C_7$ alkyl;

$R^6$ is selected from the group consisting of hydrogen, substituted or unsubstituted $C_1$-$C_4$ alkyl and substituted or unsubstituted $C_3$-$C_7$ cycloalkyl;

$R^{10}$ is independently selected from the group consisting of substituted or unsubstituted $C_1$-$C_4$ alkyl and substituted or unsubstituted $C_3$-$C_7$ cycloalkyl;

$R^{11}$ and $R^{11a}$ are the same or different and are independently selected from the group consisting of hydrogen, substituted or unsubstituted $C_1$-$C_4$ alkyl, hydroxy-$C_1$-$C_4$-alkyl, hydroxy-$C_1$-$C_4$-alkyl-$C_3$-$C_7$-cycloalkyl [or hydroxy-($C_3$-$C_7$-cycloalkyl)-$C_1$-$C_4$ alkyl], substituted or unsubstituted heterocyclo-$C_1$-$C_4$-alkyl, acyl, $C_1$-$C_4$ alkoxycarbonyl, carboxy-$C_1$-$C_4$-alkyl, substituted or unsubstituted $C_3$-$C_7$ cycloalkyl, and substituted or unsubstituted $C_3$-$C_7$ cycloalkyl-$C_1$-$C_4$-alkyl, where the $R^{11}$ and $R^{11a}$ groups and the N atom to which they are attached may optionally form a 5- to 7-membered ring, for example a 5- to 7-membered heterocyclyl ring; and a pharmaceutically acceptable salt or a stereoisomer or a prodrug ester thereof.

It will be appreciated that where D and/or W is a direct bond or other moiety as defined for D and/or W, the $R^{2a}$, $R^{2b}$ and/or $R^{2c}$ groups will be present, where possible, according to the number of available valences.

Thus, the compounds of Formula I of the invention include the following

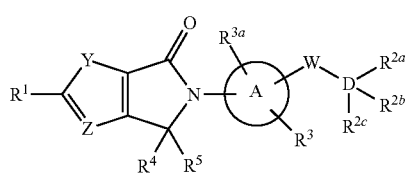

I wherein Y and Z are independently selected from C, O, S and N, wherein at least one of Y and Z is other than C;

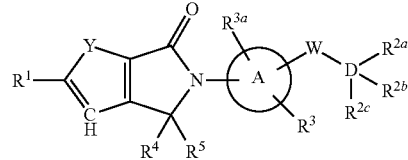

IA wherein Y is O or S; or

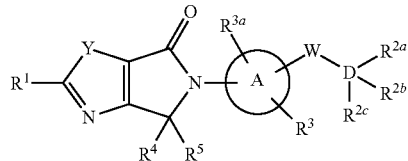

IB wherein Y is O or S.

In one embodiment of formula I of the invention, compounds are provided having the structure IC

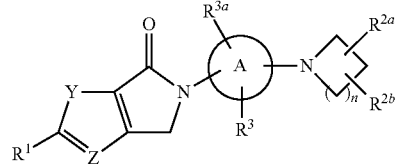

IC wherein
$R^1$, Y, Z,

$R^3$ and $R^{3a}$ are as defined for formula I;

n is 1, 2 or 3;

$R^{2a}$ and $R^{2b}$ are the same or different and can be attached to separate carbons on the cyclic amine in which case $R^{2a}$ and $R^{2b}$ are the same or different and may be independently and are preferably selected from H, $NR^{11}R^{11a}$, OH, oxo(=O), halo, cyano, acylamino, alkoxycarbonylamino, or hydroxyalkyloxycarbonylamino;

and wherein $R^{2a}$ and $R^{2b}$ and the carbons to which they are linked may optionally form a bicyclic heterocycle which can be optionally substituted with one to three substituents which can be the same or different and are independently and preferably selected from OH, CN, or oxo(=O);

and wherein $R^{2a}$ and $R^{2b}$ are the same or different and can be attached to a single carbon atom, in which case $R^{2a}$ and $R^{2b}$ may optionally be connected via a ring to form a spirocycle which can optionally be substituted with one to three substituents which may be the same or different and are independently and preferably selected from OH, CN, or oxo(=O).

Examples of preferred groups include
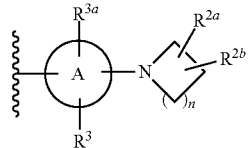
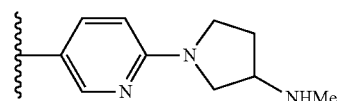
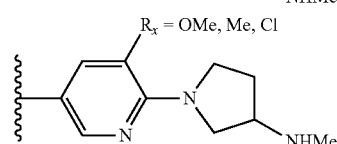
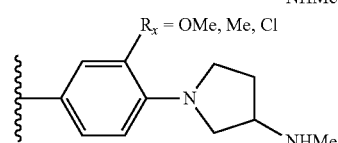
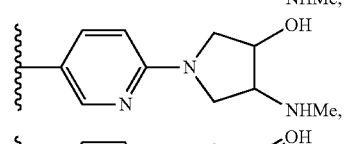
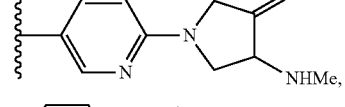
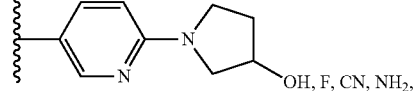
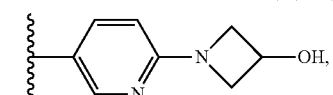
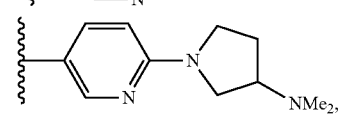
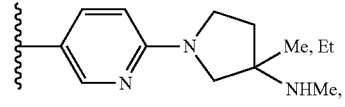
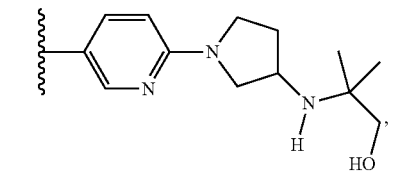
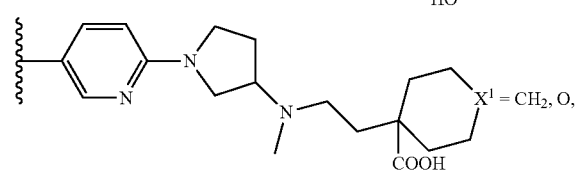
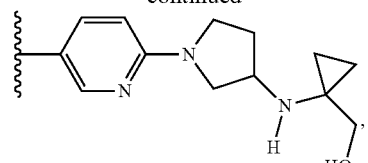
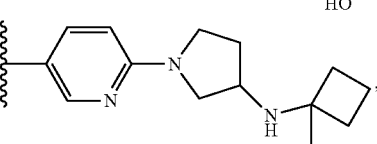
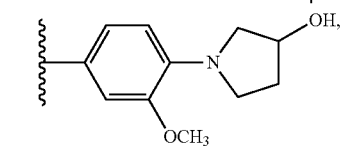
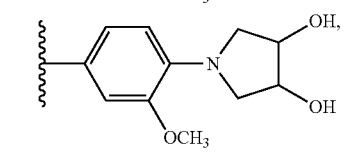
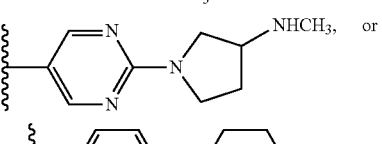
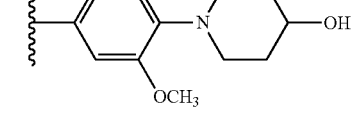
spirocyclics such as
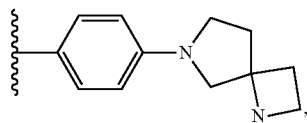
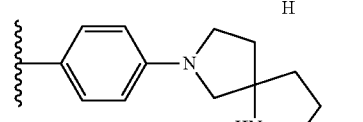
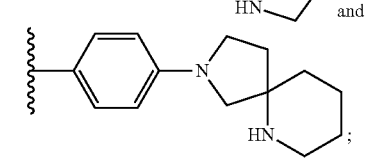
or heterocyclic azocycles such as
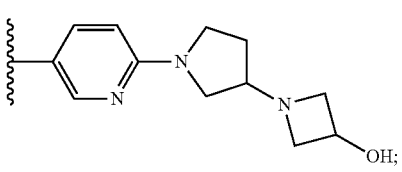 [SMILES: *c1ccc(N2CCC(N3CC(O)C3)C2)nc1]

or
 bicyclics such as

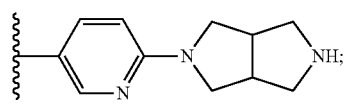

or
 carbamates such as

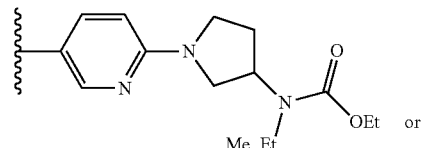

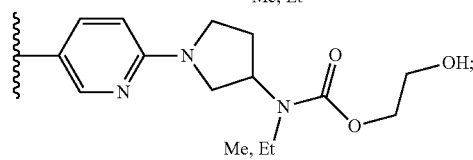

or
 amides such as

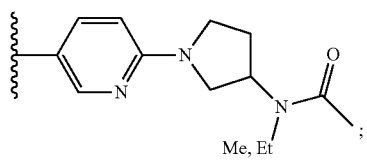

or
 lactams such as

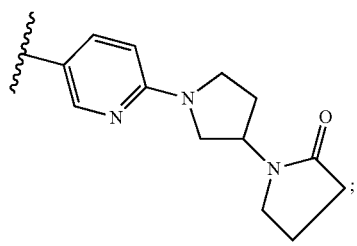 [SMILES: *c1ccc(N2CCC(N3CCCC3=O)C2)nc1]

or
 oxazolidinones such as

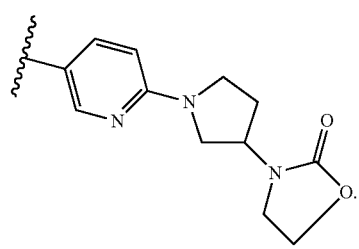 [SMILES: *c1ccc(N2CCC(N3CCOC3=O)C2)nc1]

In some embodiments of the compounds of Formula I of the invention, $R^1$ is aryl, preferably phenyl, which may or may not be substituted, and is preferably substituted at the para-position with halogen such as Cl or polyfluoroalkyl such as $CF_3$.

In some embodiments of the compounds of Formula I of the invention, Y is S and Z is CH, that is

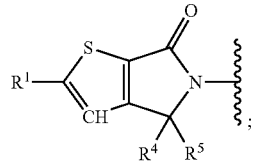

or Y is S and Z is N, that is

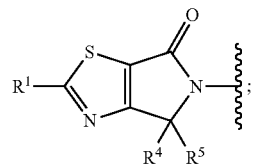

or Y is O and Z is N, that is

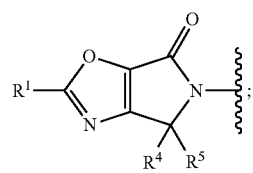

or Y is O and Z is CH, that is

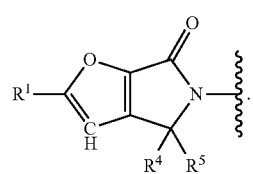

In some embodiments of the compounds of Formula I of the invention,

Ⓐ is phenylene, or a monocyclic heteroaryl which is

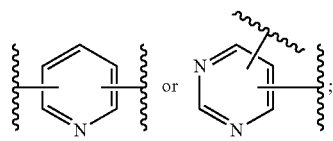

or
  wherein $R^3$ is lower alkoxy, H, halo or lower alkyl and $R^{3a}$ is H; or
  wherein W is O or a bond provided that where W is a bond (A)

is linked to the nitrogen of a cyclic or bicyclic amine; or
  wherein D is a bond or alkylene (which may optionally be substituted with cycloalkyl, lower alkyl or other substituents for alkyl), or heterocyclo (cyclic or bicyclic amine);
  wherein $R^{2a}$ is OH, heterocyclyl, or cycloalkyl; or
  wherein $R^{2b}$ and $R^{2c}$ are each hydrogen, or any of the $R^{2a}$ groups; or
  wherein $R^1$ is

[structures: phenyl; halo-phenyl; polyhaloalkyl-phenyl; halo-phenyl with halo; alkyl-phenyl; alkoxy-phenyl; polyhaloalkoxy-phenyl; alkyl-S-phenyl; alkyl-phenyl; chloropyridyl; chloropyrimidinyl; chloropyridyl; chlorothiazolyl; thienyl; pyrazolyl]

In some embodiments of the compounds of formula I of the invention, $R^1$ is phenyl, which may or may not be substituted, and is preferably substituted at the para-position with halogen such as Cl or

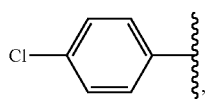

or polyfluoroalkyl such as $CF_3$, including

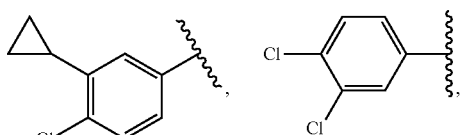

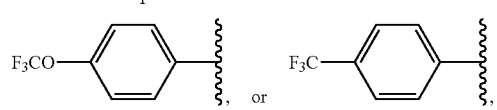, or or heteroaryl such as

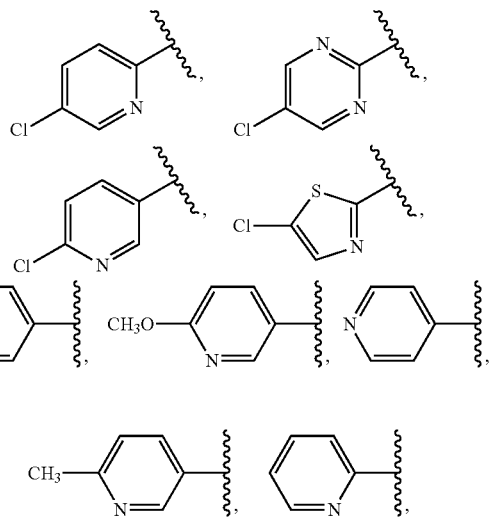, and

In some embodiments of the compounds of formula I of the invention, (A)

is phenylene, preferably

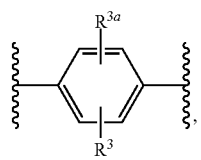

or heteroaryl which is

[chemical structures]

In some embodiments of the compounds of Formula I of the invention, $R^4$ is H and $R^5$ is H.

In some embodiments of the compounds of Formula I of the invention, $R^3$ is lower alkoxy, preferably —OCH$_3$, or H, halo or lower alkyl such as CH$_3$ or C$_2$H$_5$.

In some embodiments of the compounds of Formula I of the invention, $R^{3a}$ is H or any of the $R^3$ groups set out above.

In some embodiments of the compounds of Formula I of the invention, W is O or a direct bond provided that where W is a bond

[structure: A]

is linked to the nitrogen of a cyclic or bicyclic amine.

In some embodiments of the compounds of Formula I of the invention, D is a bond, alkylene which may be substituted with 1 or 2 of cycloalkyl, lower alkyl or other substituents for alkyl, or heterocycle such as

[chemical structures]

In some embodiments of the compounds of Formula I of the invention, $R^{2a}$ is OH or heterocycle such as

[chemical structure]

In some embodiments of the compounds of formula I of the invention, D is a bond or C$_1$-C$_2$ alkylene which may be unsubstituted or substituted.

In some embodiments of the compounds of formula I of the invention, $R^{2a}$ is H, lower alkyl, such as CH$_3$, hydroxyalkyl such as

[chemical structures]

cycloalkyl such as

[chemical structure]

cycloalkylalkyl such as

[chemical structure]

or heterocycle-C$_1$-C$_4$-alkyl such as

[chemical structures]

OH, heterocyclyl such as

[chemical structures]

(where $R^{21}$ is lower alkyl),

[chemical structures]

where $R^9$, and $R^{11}$ and $R^{11a}$ are independently H or C$_1$-C$_4$ alkyl, such as

[chemical structure]

or its HCl salt,

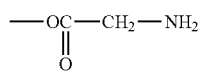

or its HCl salt, mono- or -dialkylaminoheterocyclyl such as

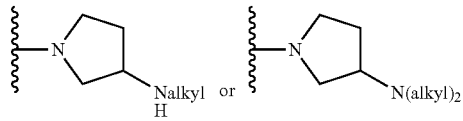

(where alkyl is preferably $CH_3$), $NR^{11}R^{11a}$ such as

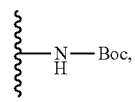

$NH_2$, $NHCH_3$ or $N(CH_3)_2$ or heteroaryl such as

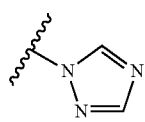

or $SO_2R^{10}$ where $R^{10}$ is $C_1$-$C_4$ alkyl, such as $CH_3$ or $C_2H_5$, $C_3$-$C_7$ cycloalkyl such as cyclopropyl or cyclobutyl or dihalocycloalkyl such as

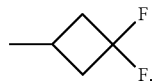

In some embodiments of the compounds of formula I of the invention, $R^{2b}$ and $R^{2c}$ are independently H, $C_3$-$C_7$ cycloalkyl such as

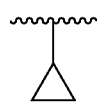 [SMILES: *C1CC1]

or $C_1$-$C_4$ alkyl such as $CH_3$, or can be any of the $R^{2a}$ groups as set out above, or are absent.

In some embodiments of the compounds of formula I of the invention

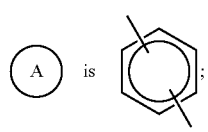

wherein W is O or a bond provided that where W is a bond

is linked to the nitrogen of a cyclic or bicyclic amine, and D is $CH_2$, $CH_2CH_2$, $CH_2CH_2CH_2$,

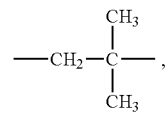

or a bond; or
wherein $R^{2a}$ is

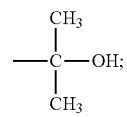

or
wherein $R^1$ is

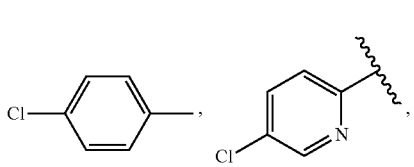

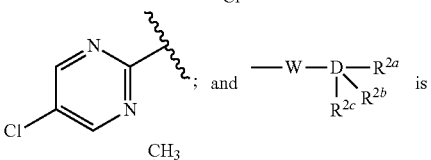; and $-W-D\genfrac{}{}{0pt}{}{R^{2a}}{R^{2c}\phantom{}R^{2b}}$ is

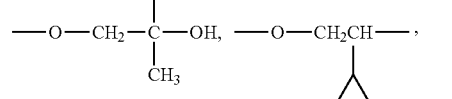

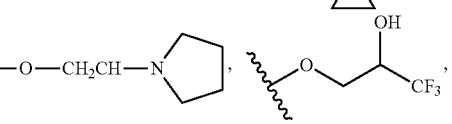

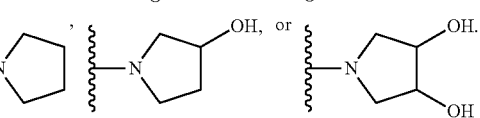

In some embodiments of the compounds of formula I of the invention,

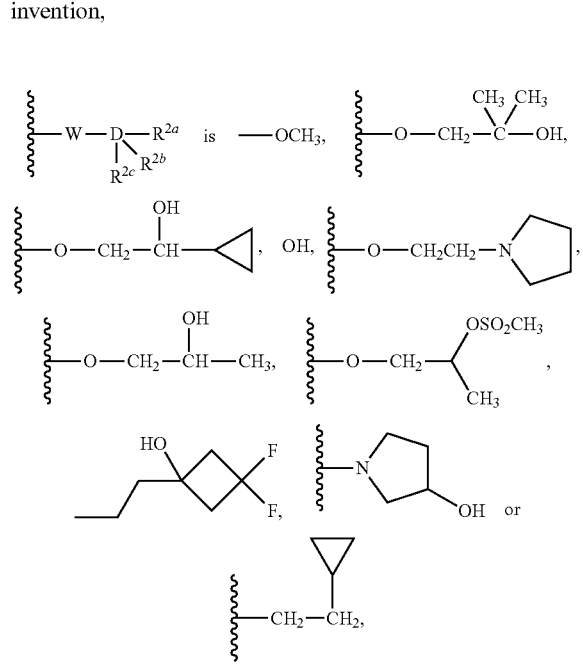

(preferably —OCH₃,

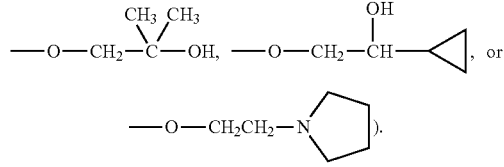

).

In some embodiments of the compounds of formula I of the invention,

R¹ is aryl such as

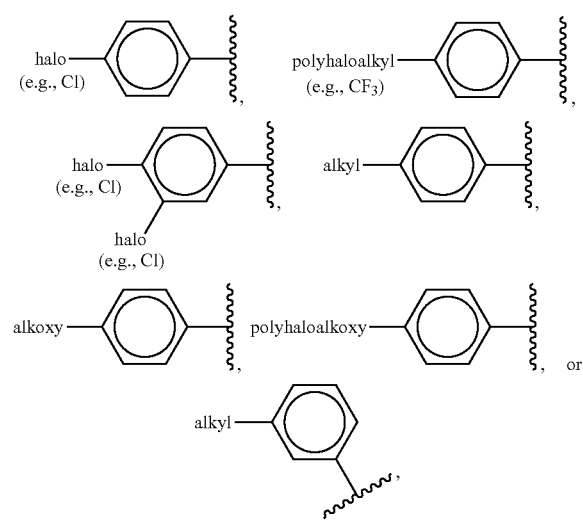

or R¹ is heteroaryl which is

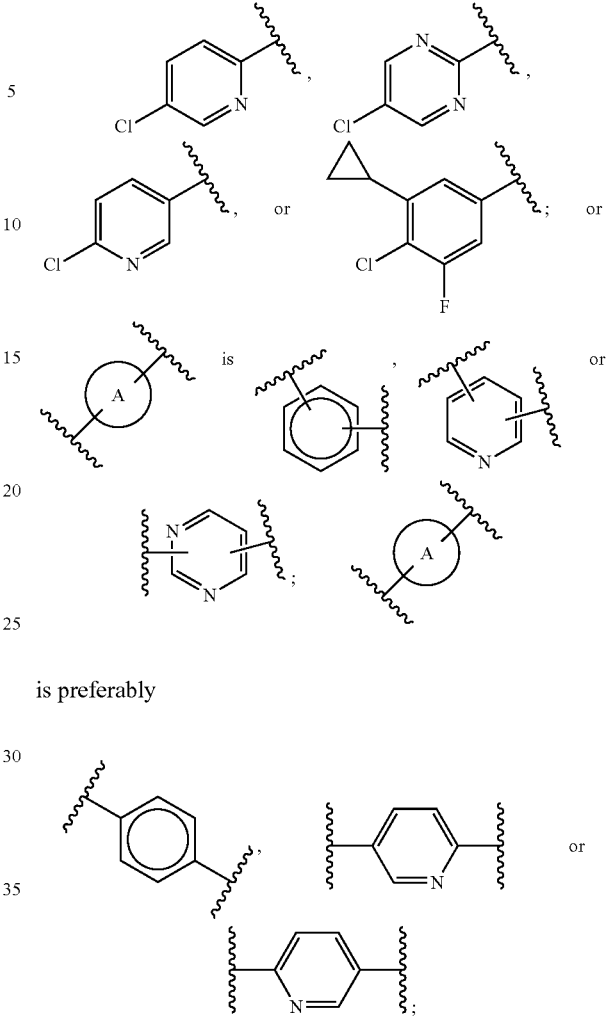

is preferably

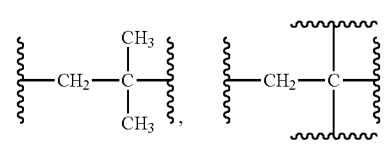

R³ is H, lower alkyl, preferably CH₃ or alkoxy, preferably OCH₃;
R$^{3a}$ is H;
R⁴ is H;
R⁵ is H;
D is lower alkyl such as CH₂, CH₂CH₂, or CH₂CH₂CH₂,

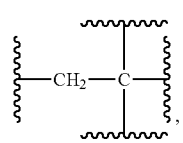

or a bond, preferably

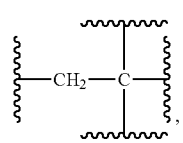

or heterocyclo, preferably

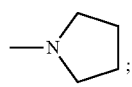

$R^{2a}$ is heterocyclyl such as

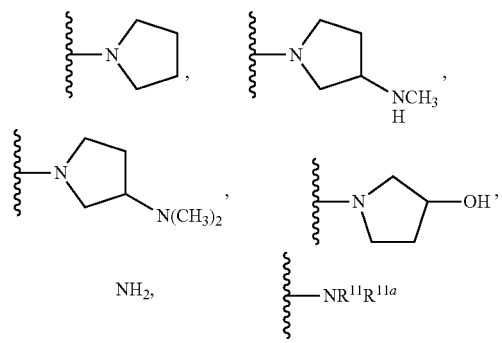

such as

or NHCH$_3$, or cycloalkyl such as

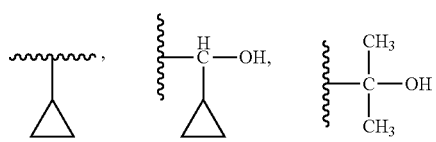

or OH;

$R^{2b}$ and $R^{2c}$ are independently H, CH$_3$OH, SO$_2$CH$_3$, SO$_2$C$_2$H$_5$, CH$_2$OH, or F; and W is O.

In some embodiments of the compounds of formula I of the invention $R^1$

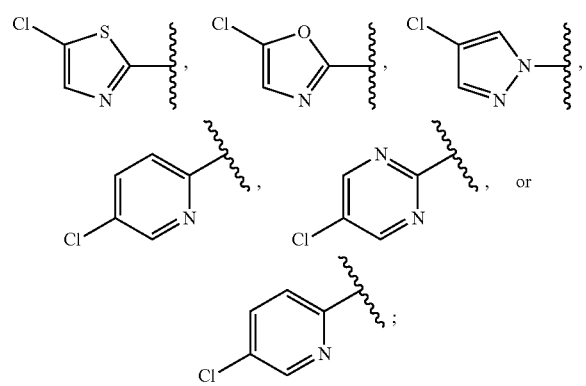

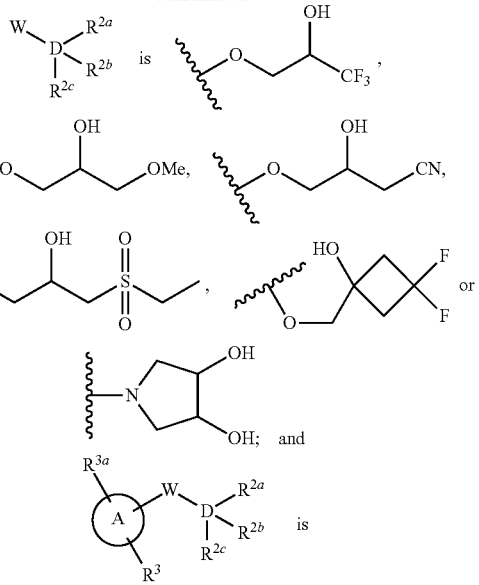

In some embodiments of the compounds of Formula I of the invention, $R^1$ is

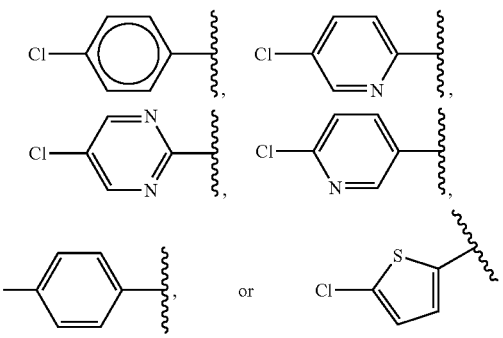

Y is —S— and Z is —CH—; or Y is —O— and Z is —CH—;

$R^4$ and $R^5$ are each H;

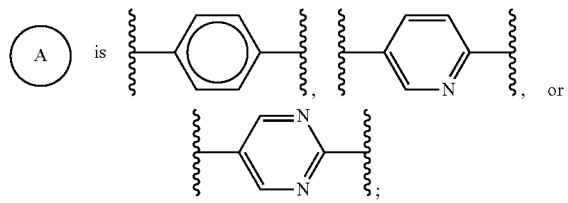

$R^{3a}$ is H, C$_1$-C$_4$ alkoxy such as CH$_3$O or C$_1$-C$_4$ alkyl such as CH$_3$;

$R^3$ is H or any of the $R^{3a}$ groups set out above;

W is O;
D is $C_1$-$C_4$ alkylene such as

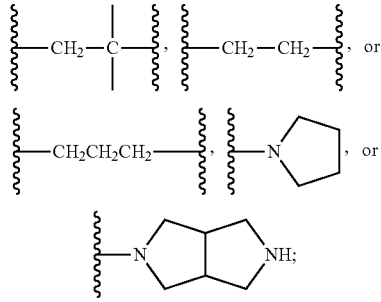

$R^{2a}$ is H, OH, heterocyclo such as

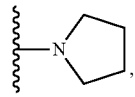

$C_1$-$C_4$ alkylamino such as —$NHCH_3$, $C_3$-$C_7$ cycloalkyl such as

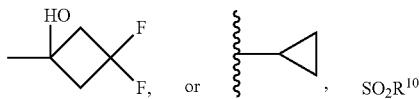

wherein $R^{10}$ is $C_1$-$C_4$ alkyl such as $CH_3$ or $C_2H_5$,

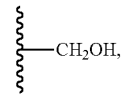

$C_1$-$C_4$ dialkylamino such as

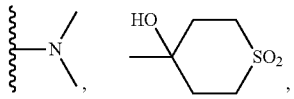

or $CF_3$;
$R^{2b}$ and $R^{2c}$ are independently selected from H, OH, $C_1$-$C_4$ alkyl such as $CH_3$, $CF_3$, $SO_2R^{10}$ where $R^{10}$ is $C_1$-$C_4$ alkyl such as $CH_3$, or $C_2H_5$, or

—$CH_2OH$, or any of the $R^{2a}$ groups set out above;
or an HCl or TFA of the compounds set out above;
or an amino acid ester prodrug of the above compounds where the amino acid has the formula $$-OC(O)CH(NH_2)\underset{R^9}{|}$$

wherein $R^9$ is H or $C_1$-$C_4$ alkyl such as $CH_3$, $C_2H_5$ or i-$C_3H_7$, or the HCl salt thereof.
Examples of compounds of the invention include:

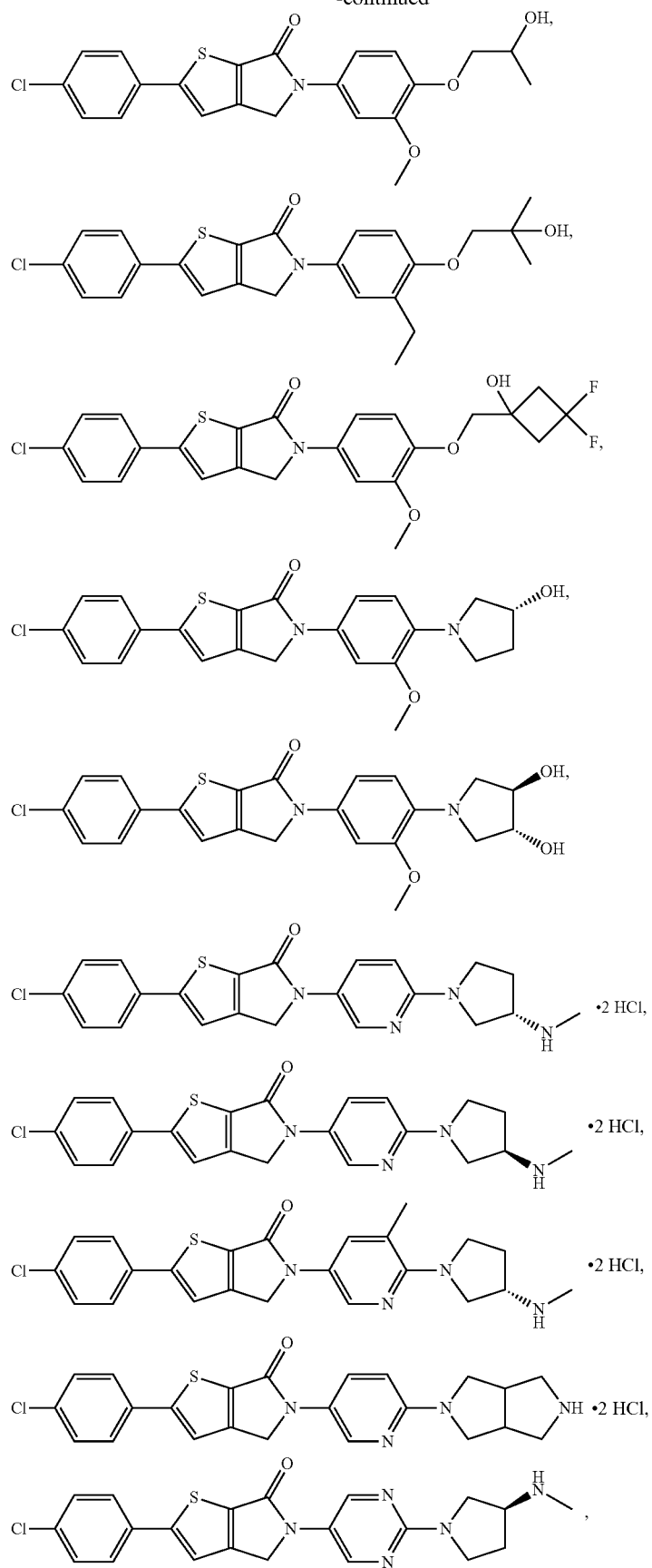

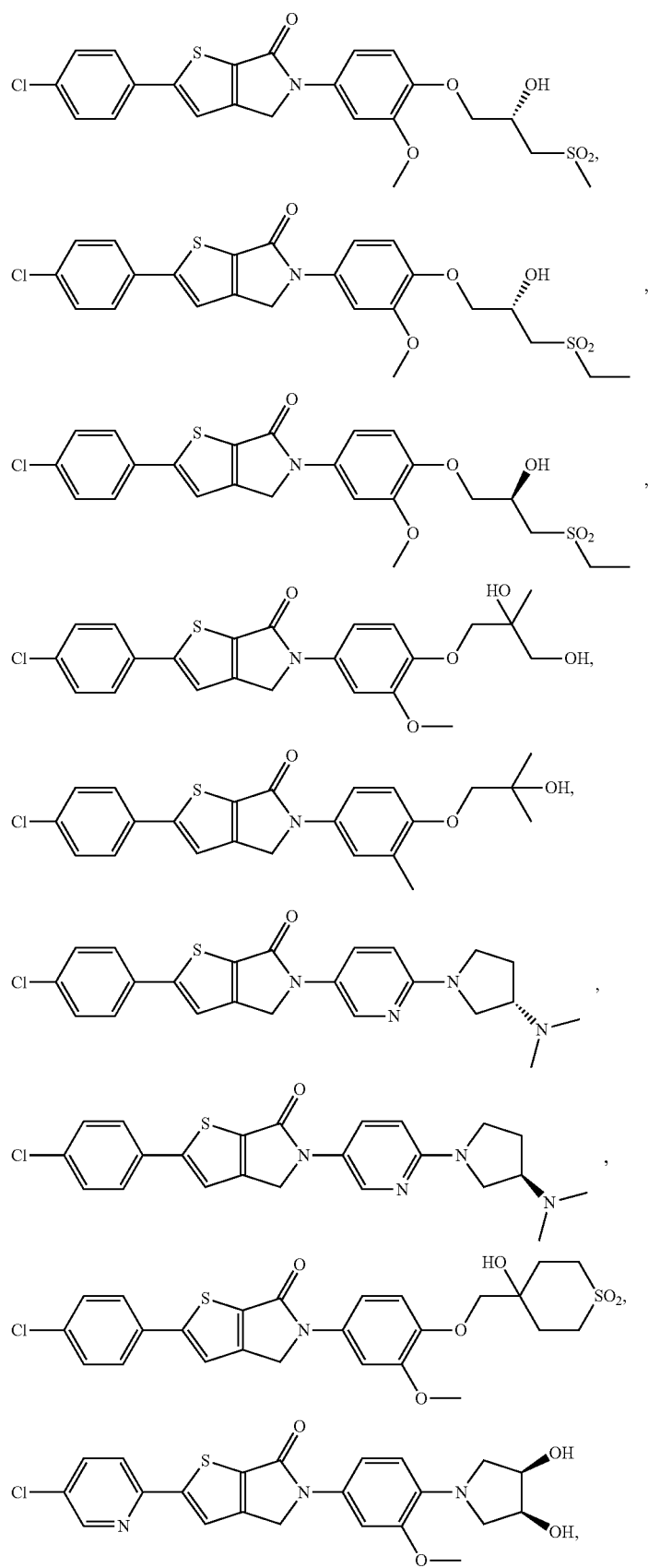

-continued
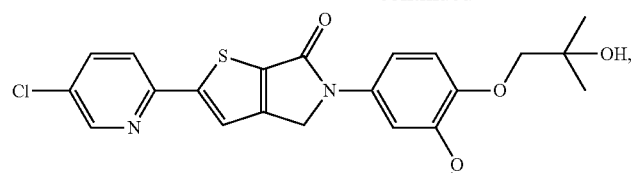
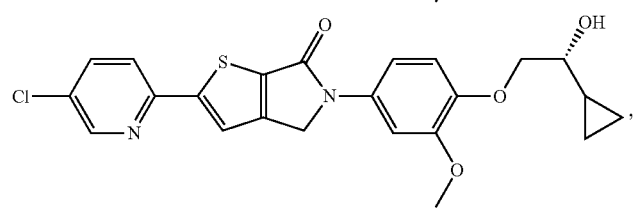
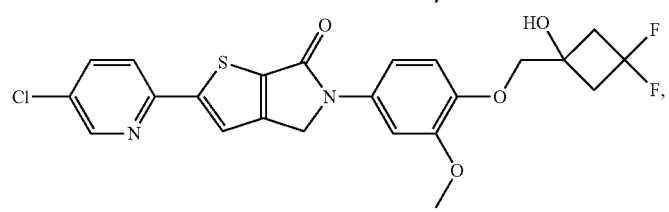
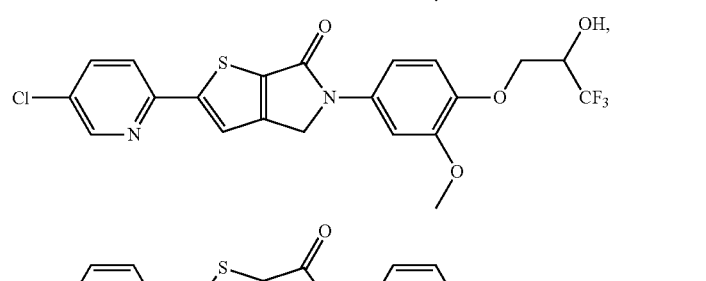
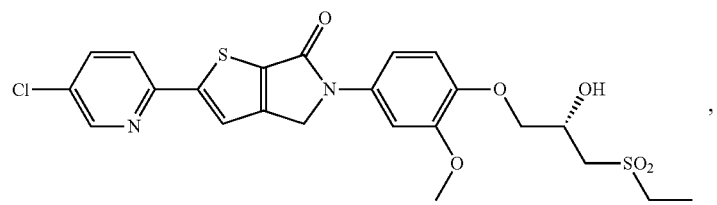
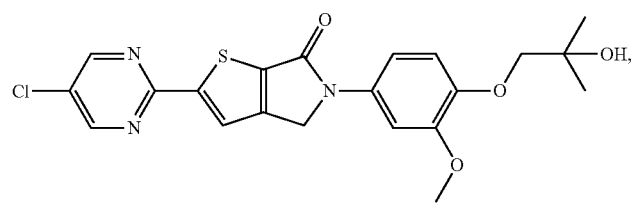
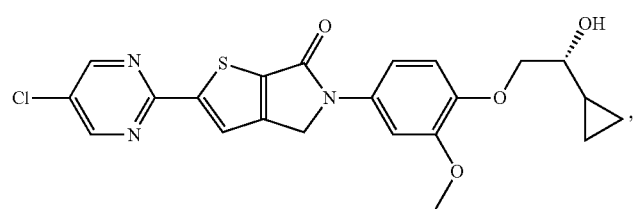
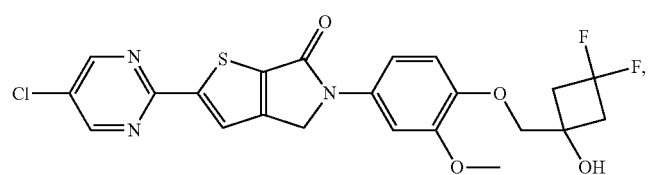

-continued
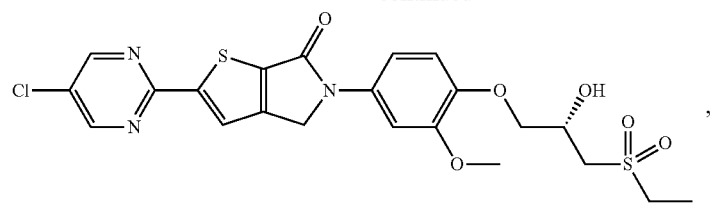
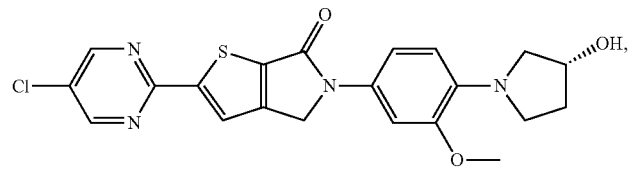
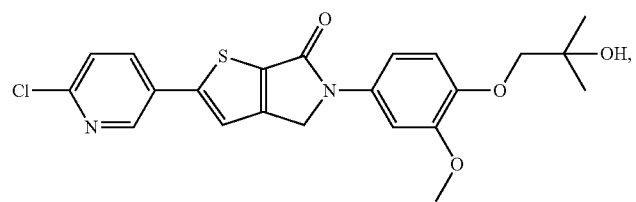
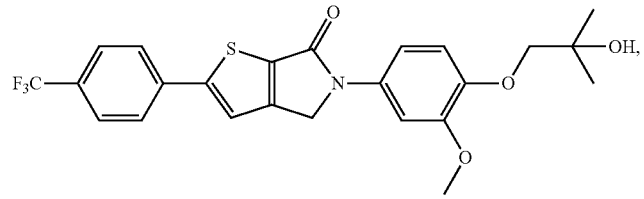
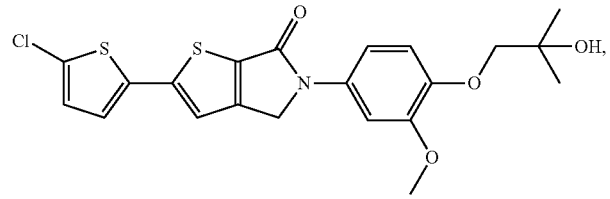
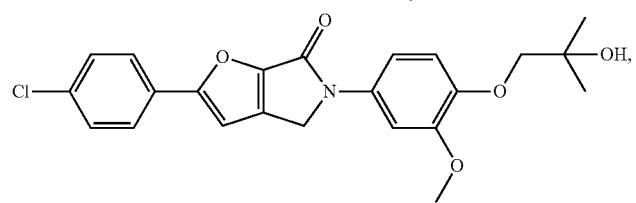
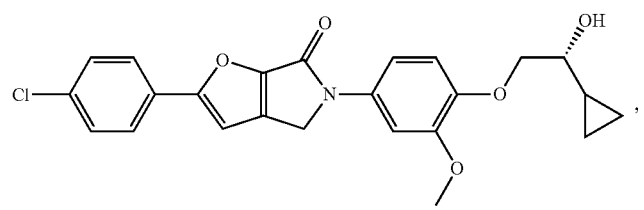
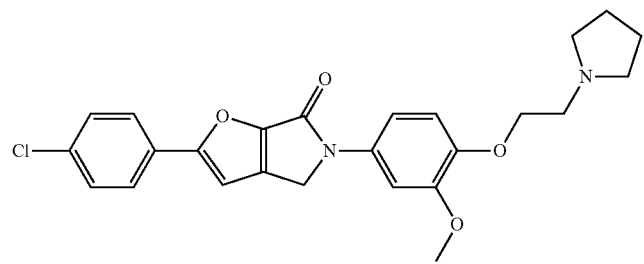

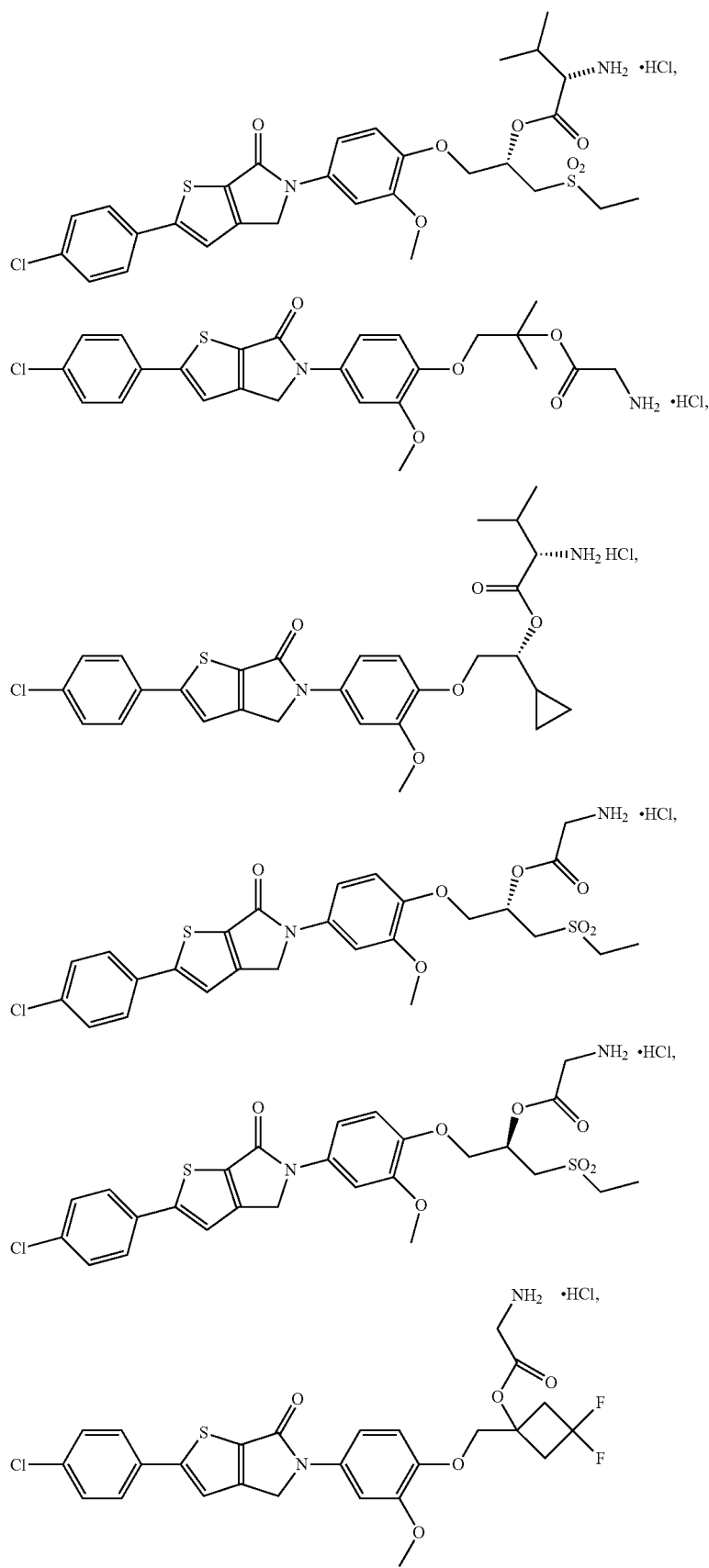

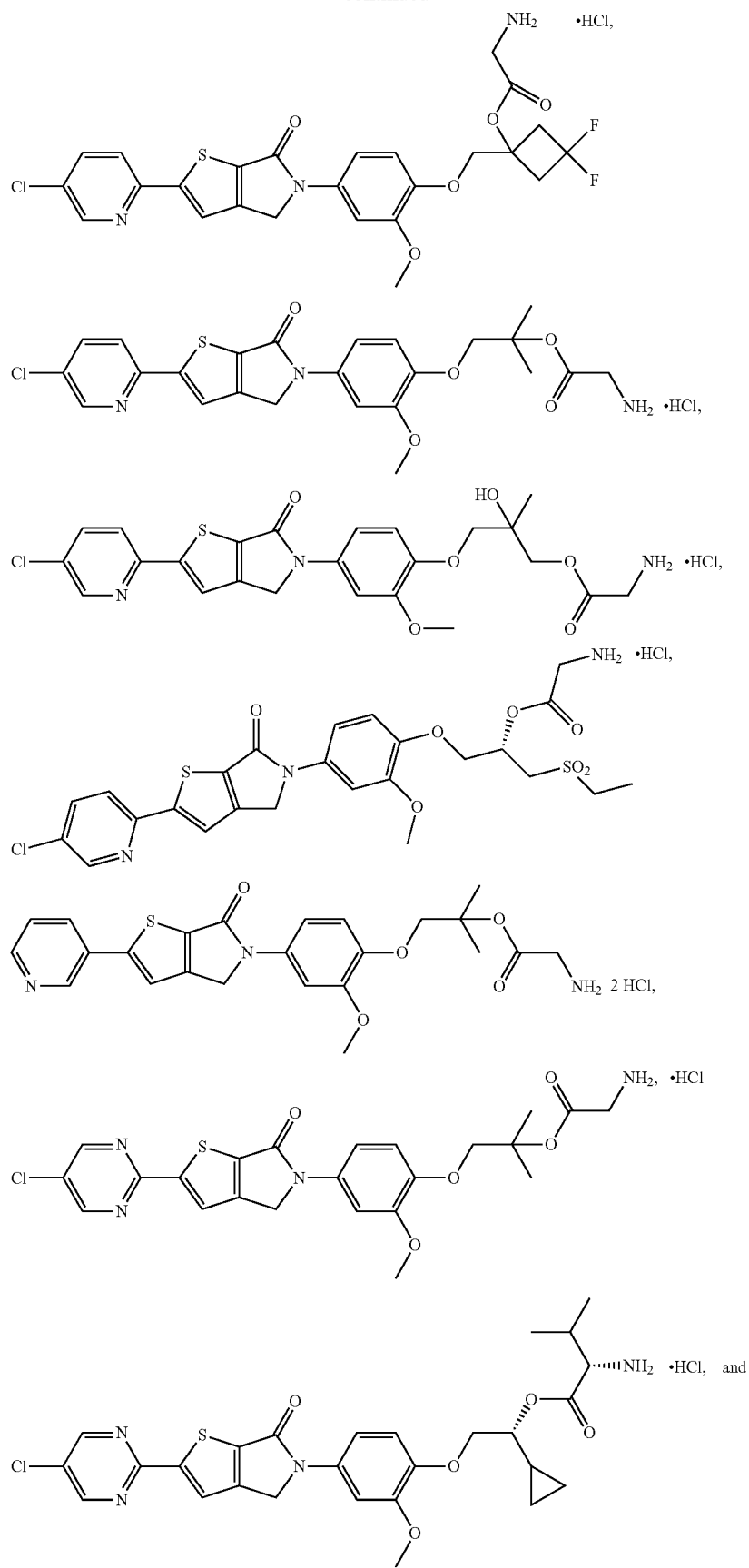

-continued

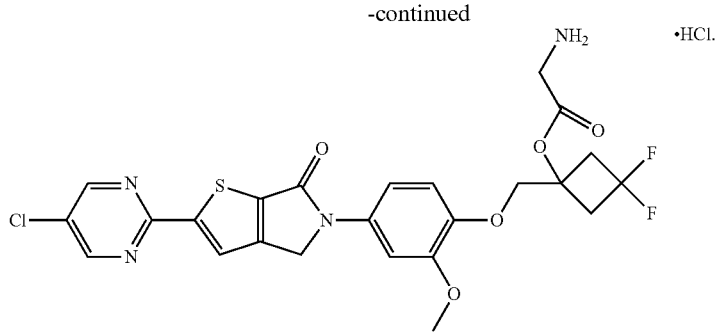

In some embodiments of the present invention, pharmaceutical compositions are provided which include at least one compound having the Formula I, as described above, and at least one pharmaceutically acceptable diluent or carrier.

In some embodiments of the present invention, methods are provided for treating a patient suffering from an MCHR1 modulated disease or disorder such as, for example, obesity, diabetes, depression or anxiety by administration of a therapeutically effective dose of a compound according to Formula I, optionally in combination with other therapeutic agents, such as those described below.

DETAILED DESCRIPTION OF THE INVENTION

Definitions

Unless otherwise indicated, the term "lower alkyl" as employed herein alone or as part of another group includes both straight and branched chain hydrocarbons containing 1 to 8 carbons, preferably 1 to 6 carbons, and the terms "alkyl" and "alk" as employed herein alone or as part of another group includes both straight and branched chain hydrocarbons containing 1 to 20 carbons, preferably 1 to 10 carbons, more preferably 1 to 8 carbons, in the normal chain, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, the various branched chain isomers thereof, and the like as well as such groups, preferably substituted $C_1$-$C_4$ alkyl, including 1 to 4 substituents such as halo, for example F, Br, Cl or I or $CF_3$, alkyl, alkoxy, aryl, aryloxy, aryl(aryl) or diaryl, arylalkyl, arylalkyloxy, alkenyl, alkynyl, cycloalkyl, cycloalkenyl, cycloalkylalkyl, cycloalkylalkyloxy, hydroxy, hydroxyalkyl, acyl, alkanoyl, heteroaryl, heteroaryloxy, cycloheteroalkyl, arylheteroaryl, arylalkoxycarbonyl, heteroarylalkyl, heteroarylalkoxy, aryloxyalkyl, aryloxyaryl, alkylamido, alkanoylamino, arylcarbonylamino, nitro, cyano, thiol, haloalkyl, trihaloalkyl and/or alkylthio.

Unless otherwise indicated, the term "cycloalkyl" or "lower cycloalkyl" as employed herein alone or as part of another group includes saturated or partially unsaturated (containing 1 or 2 double bonds) cyclic hydrocarbon groups containing 1 to 3 rings, any one of which may optionally be a spiro substituted cycloalkyl, including monocyclicalkyl, bicyclicalkyl and trieyclicalkyl, containing a total of 3 to 7 carbons forming the rings, preferably 3 to 10 carbons, forming the ring and which may be fused to 1 or 2 aromatic rings as described for aryl, which include cyclopropyl, cyclobutyl, cyclopentyl, cyclohexyl, cycloheptyl, cyclooctyl, cyclodecyl and cyclododecyl, cyclohexenyl,

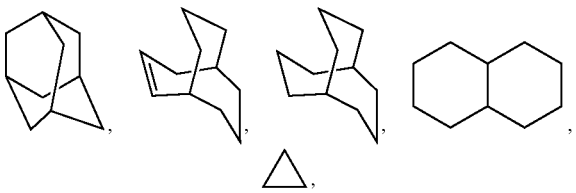

any of which groups (preferably $C_3$-$C_7$ substituted cycloalkyl) may be optionally substituted with 1 to 4 substituents such as halogen, alkyl, alkoxy, hydroxy, aryl, aryloxy, arylalkyl, cycloalkyl, alkylamido, alkanoylamino, oxo, acyl, arylcarbonylamino, nitro, cyano, thiol and/or alkylthio and/or any of the alkyl substituents.

Unless otherwise indicated, the term "cycloalkoxy" or "lower cycloalkoxy" as employed herein alone or as part of another group, represents a 4-, 5- or 6-membered saturated ring containing an oxygen in the ring and includes

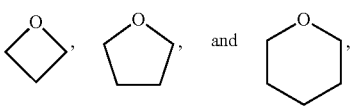

and which may be optionally substituted with 1 or 2 of any of the substituents as set out for cycloalkyl.

Unless otherwise indicated, the term "heterocyclo" "heterocyclyl", or "heterocyclic" as used herein, alone or as part of another group, represents an unsubstituted or substituted stable 4- to 7-membered monocyclic ring system which may be saturated or unsaturated, and which consists of carbon atoms, with one to four heteroatoms selected from nitrogen, oxygen or sulfur, and wherein the nitrogen and sulfur heteroatoms may optionally be oxidized, and the nitrogen heteroatom may optionally be quaternized. The heterocyclic ring may be attached at any heteroatom or carbon atom which results in the creation of a stable structure. Examples of such heterocyclic groups include, but is not limited to, piperidinyl, piperazinyl, oxopiperazinyl, oxopiperidinyl, oxopyrrolidinyl, oxoazepinyl, azepinyl, pyrrolyl, pyrrolidinyl, furanyl, thienyl, pyrazolyl, pyrazolidinyl, imidazolyl, imidazolinyl, imidazolidinyl, pyridyl, pyrazinyl, pyrimidinyl, pyridazinyl, oxazolyl, oxazolidinyl, isooxazolyl, isoxazolidinyl, morpholinyl, thiazolyl, thiazolidinyl, isothiazolyl, thiadiazolyl, tetrahydropyranyl, thiamorpholinyl, thiamorpholinyl sulfoxide, thiamorpholinyl sulfone, oxadiazolyl and other heterocycles described in Katritzky, A. R. et al., eds., *Comprehensive Heterocyclic Chemistry: The Structure, Reactions, Synthesis and Uses of Heterocyclic Compounds*, Pergamon Press, New York, N.Y. (1984); and Katritzky, A. R. et al., eds., *Comprehensive Heterocyclic Chemistry II: A Review of the Literature* 1982-1995, Elsevier Science, Inc., Tarrytown, N.Y. (1996); and references therein. The heterocyclo may optionally be substituted with at least one of F, Br, Cl or I or $CF_3$, alkyl, alkoxy, aryl, aryloxy, aryl(aryl) or diaryl, arylalkyl, arylalkyloxy, alkenyl, alkynyl, cycloalkyl, cycloalkenyl, cycloalkylalkyl, cycloalkylalkyloxy, hydroxy, hydroxyalkyl, acyl, alkanoyl, heteroaryl, heteroaryloxy, cycloheteroalkyl, arylheteroaryl, arylalkoxycarbonyl, heteroarylalkyl, heteroarylalkoxy, aryloxyalkyl, aryloxyaryl, alkylamido, alkanoylamino, arylcarbonylamino, nitro, cyano, thiol, haloalkyl, trihaloalkyl and/or alkylthio.

The term "alkanoyl" as used herein alone or as part of another group refers to alkyl linked to a carbonyl group.

The term "halogen" or "halo" as used herein alone or as part of another group refers to chlorine, bromine, fluorine, and iodine, with chlorine or fluorine being preferred.

The term "metal ion" refers to alkali metal ions such as sodium, potassium or lithium and alkaline earth metal ions such as magnesium and calcium, as well as zinc and aluminum.

The term "aryl" herein alone or as part of another group refers to monocyclic or bicyclic aromatic rings, e.g., phenyl, substituted phenyl and the like, as well as groups which are fused, e.g., naphthyl, phenanthrenyl and the like. An aryl group thus contains at least one ring having at least 6 atoms, with up to five such rings being present, containing up to 22 atoms therein, with alternating (resonating) double bonds between adjacent carbon atoms or suitable heteroatoms. Aryl groups such as phenyl may optionally be substituted with one or more groups including, but not limited to halogen, alkyl, alkenyl, cycloalkyl, heterocycloalkyl, alkoxy, haloalkoxy, haloalkyl, hydroxy, carboxy, carbamoyl, alkyloxycarbonyl, nitro, alkenyloxy, trifluoromethyl, amino, cycloalkyl, aryl, heteroaryl, cyano, alkyl $S(O)_m$ (m=0, 1, 2), or thiol and/or any of the alkyl substituents set out herein.

Unless otherwise indicated, the term "heteroaryl" as used herein alone or as part of another group refers to a 5- or 6-membered aromatic ring which includes 1, 2, 3 or 4 hetero atoms such as nitrogen, oxygen or sulfur. Such rings may be fused to an aryl, cycloalkyl, heteroaryl or heterocyclyl and include possible N-oxides as described in Katritzky, A. R. et al., eds. *Comprehensive Heterocyclic Chemistry: The Structure, Reactions, Synthesis and Uses of Heterocyclic Compounds*, Pergamon Press, New York, N.Y. (1984); and Katritzky, A. R. et al., eds., *Comprehensive Heterocyclic Chemistry II: A Review of the Literature* 1982-1995, Elsevier Science, Inc., Tarrytown, N.Y. (1996); and references therein. Further, "heteroaryl", as defined herein, may optionally be substituted with one or more substituents such as the substituents included above in the definition of "alkyl" and "aryl". Examples of heteroaryl groups include the following:

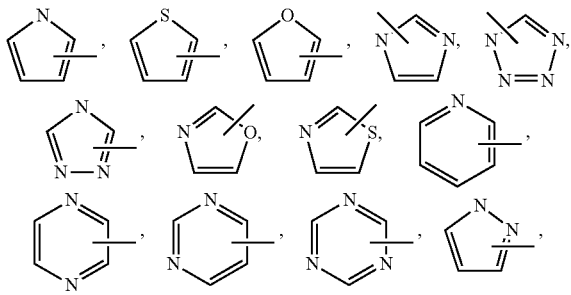

and the like.

Unless otherwise indicated, the term "$C_1$-$C_4$ alkoxy", "alkoxy", "aryloxy" or "aralkoxy" as employed herein alone or as part of another group includes any of the above alkyl, aralkyl or aryl groups linked to an oxygen atom.

Unless otherwise indicated, the term "lower alkylthio", alkylthio", "arylthio" or "aralkylthio" as employed herein alone or as part of another group includes any of the above alkyl, aralkyl or aryl groups linked to a sulfur atom.

The term "polyhaloalkyl" ("polyfluoroalkyl" or "perfluoroalkyl") as used herein refers to an "alkyl" group as defined above which includes from 2 to 9, preferably from 2 to 5, halo substituents, such as F or Cl, preferably F, such as $CF_3CH_2$, $CF_3$ or $CF_3CF_2CH_2$.

The term "polyhaloalkyloxy" ("polyfluoroalkyl" or "perfluoroalkyl") as used herein refers to an "alkoxy" or "alkyloxy" group as defined above which includes from 2 to 9, preferably from 2 to 5, halo substituents, such as F or Cl, preferably F, such as $CF_3CH_2O$, $CF_3O$ or $CF_3CF_2CH_2O$.

The term "polyhaloalkyloxy" as used herein refers to an "alkoxy" or "alkyloxy" group as defined above which includes from 2 to 9, preferably from 2 to 5, halo substituents, such as F or Cl, preferably F, such as $CF_3CH_2O$, $CF_3O$ or $CF_3CF_2CH_2O$.

The term "acyl" as used herein alone or as part of another group refers to a radical linked to a carbonyl (C=O) group which radical can be, for example, $C_1$-$C_4$ alkyl, aryl, heterocyclo, heteroaryl, $C_3$-$C_7$ cycloalkyl, $C_1$-$C_4$ alkoxy or amino.

Pharmaceutical Compositions

According to some embodiments of the present invention, pharmaceutical compositions are provided, comprising at least one compound having Formula I, as described herein, and at least one pharmaceutically acceptable diluent or carrier. The pharmaceutical compositions of the present invention, may optionally include at least one additional therapeutic agent selected from the group consisting of anti-obesity agents; anti-diabetic agents, appetite suppressants; cholesterol/lipid-lowering agents, and HDL-raising agents, as defined herein.

The present invention is also directed to pharmaceutical combinations, comprising at least one compound having the Formula I, and at least one additional therapeutic agent, selected from the group consisting of anti-obesity agents;

anti-diabetic agents, appetite suppressants; cholesterol/lipid-lowering agents, and HDL-raising agents, as defined herein.

According to one embodiment of the present invention, the anti-diabetic agent is selected from the group consisting of insulin secretagogues, insulin sensitizers, glucokinase inhibitors, glucocorticoid antagonist, fructose 1,6-bis phosphatase inhibitors, AMP kinase activators, incretin modulators glucosidase inhibitors, aldose reductase inhibitors PPAR γ agonists, PPAR α agonists, PPAR δ antagonists or agonists, PPAR α/γ dual agonists, 11-β-HSD-1 inhibitors, dipeptidyl peptidase IV (DP4) inhibitors, SGLT2 inhibitors, insulin, glucagon-like peptide-1 (GLP-1), GLP-1 agonists, and PTP-1B inhibitors.

According to one embodiment of the present invention, the additional therapeutic agent is an antiobesity agent selected from group consisting of melanocortin receptor (MC4R) agonists, cannabinoid receptor modulators, growth hormone secretagogue receptor (GHSR) antagonists, galanin receptor modulators, orexin antagonists, CCK agonists, GLP-1 agonists, pre-proglucagon-derived peptides; NPY1 or NPY5 antagonists; NPY2 and NPY4 modulators; orticotropin releasing factor agonists, histamine receptor-3 (H3) modulators, aP2 inhibitors, PPAR gamma modulators, PPAR delta modulators, acetyl-CoA carboxylase (ACC) inhibitors, 11-β-HSD-1 inhibitors, adinopectin receptor modulators; beta 3 adrenergic agonists, thyroid receptor beta modulators, lipase inhibitors, serotonin receptor agonists, monoamine reuptake inhibitors or releasing agents, anorectic agents, CNTF, BDNF, DGAT inhibitors, leptin, leptin receptor modulators, and cannabinoid-1 receptor inverse agonists/neutral antagonists.

Methods of Use

According to one embodiment of the present invention, methods are provided for treating obesity in a patient in need of such treatment, which includes the step of administering a therapeutically effective amount of at least one compound according to Formula I alone or in combination with one or more additional antiobesity agents, wherein the obesity agent is selected from those described herein.

According to one embodiment of the present invention, methods are provided for treating diabetes, especially Type II diabetes, in a patient in need of such treatment, which includes the step of administering a therapeutically effective amount of at least one compound according to Formula I alone or in combination with one or more additional antidiabetic agents, wherein the diabetic agent is described herein.

According to one embodiment of the present invention, methods for treating depression in a patient are provided, comprising administering a therapeutically effective amount of at least one compound according to Formula I.

According to one embodiment of the present invention, methods are provided for treating anxiety in a patient in need of such treatment, comprising administering a therapeutically effective amount of a compound having Formula I.

According to another embodiment of the present invention, methods are provided for treating intestinal inflammatory conditions, such as inflammatory bowel disease (IBD), colitis and Crohn's disease (CD) in a patient in need of such treatment which includes the step of administering a therapeutically effective amount of a compound of Formula I.

The assessment of activity of the compounds of Formula I of the invention in treating intestinal inflammation such as caused by inflammatory bowel disease, colitis and/or Crohn's disease, as described above, may be carried out employing the various assays as disclosed in Kokkotou, E. et al., "Melanin-concentrating hormone as a mediator of intestinal inflammation", *Proc. Natl. Acad. Sci.*, 105(30):10613-10618 (Jul. 29, 2008).

Utility

The compounds of the present invention can be administered to mammals, preferably humans, for the treatment of a variety of conditions and disorders, including, but not limited to metabolic and eating disorders as well as conditions associated with metabolic disorders (e.g., obesity, diabetes, arteriosclerosis, hypertension, polycystic ovary disease, cardiovascular disease, osteoarthritis, dermatological disorders, impaired glucose hemostasis, insulin resistance, hypercholesterolemia, hypertriglyceridemia, cholelithiasis, dislipidemic conditions, bulimia nervosa and compulsive eating disorders); sleep disorders; and psychiatric disorders, such as depression, anxiety, schizophrenia, substance abuse, cognition-enhancement and Parkinson's disease; and inflammatory diseases such as inflammatory bowel disease, colitis and/or Crohn's disease.

The compounds described in the present invention could be used to enhance the effects of cognition-enhancing agents, such as acetylcholinesterase inhibitors (e.g., tacrine), muscarinic receptor-1 agonists (e.g., milameline), nicotinic agonists, glutamic acid receptor (AMPA and NMDA) modulators, and neurotropic agents (e.g., piracetam, levetiracetam). Examples of suitable therapies for treatment of Alzheimer's disease and cognitive disorders for use in combination with the compounds of the present invention include donepezil, tacrine, revastigraine, 5HT6, gamma secretase inhibitors, beta secretase inhibitors, SK channel blockers, Maxi-K blockers, and KCNQs blockers.

The compounds described in the present invention could be used to enhance the effects of agents used in the treatment of Parkinson's Disease. Examples of agents used to treat Parkinson's Disease include: levadopa with or without a COMT inhibitor, antiglutamatergic drugs (amantadine, riluzole), alpha-2 adrenergic antagonists such as idazoxan, opiate antagonists, such as naltrexone, other dopamine agonists or transporter modulators, such as ropinirole, or pramipexole or neurotrophic factors such as glial derived neurotrophic factor (GDNF).

Dosage Forms

The compounds of the present invention can be administered in oral dosage form. The dosage form for said pharmaceutical composition includes such oral dosage foul's as granules, powders, tablets, capsules, syrups, emulsions, suspensions, etc. and such non-oral dosage forms as injections (e.g., subcutaneous, intravenous, intramuscular and intraperitoneal injections), drip infusions, external application forms (e.g., nasal spray preparations, transdermal preparations, ointments, etc.), and suppositories (e.g., rectal and vaginal suppositories).

These dosage forms can be manufactured by the per se known technique conventionally used in pharmaceutical procedures. The specific manufacturing procedures are as follows.

To manufacture an oral dosage form, an excipient (e.g., lactose, sucrose, starch, mannitol, etc.), a disintegrator (e.g., calcium carbonate, carboxymethylcellulose calcium, etc.), a binder (e.g., α-starch, gum arabic, carboxymethylcellulose, polyvinylpyrrolidone, hydroxypropylcellulose, etc.), and a lubricant (e.g., talc, magnesium stearate, polyethylene glycol 6000, etc.), for instance, are added to the active component or components and the resulting composition is compressed. Where necessary, the compressed product is coated, by the per se known technique, for masking the taste or for enteric dissolution or sustained release. The coating material that can be used includes, for instance, ethylcellulose, hydroxymethylcellulose, polyoxyethylene glycol, cellulose acetate phthalate, hydroxypropylmethylcellulose phthalate, and EUDRAGIT® (Rohm & Haas, Germany, methacrylic-acrylic copolymer).

Injections can be manufactured typically by the following procedure. The active component or components are dissolved, suspended or emulsified in an aqueous vehicle (e.g., distilled water, physiological saline, Ringer's solution, etc.) or an oily vehicle (e.g., vegetable oil such as olive oil, sesame oil, cottonseed oil, corn oil, etc. or propylene glycol) together with a dispersant, e.g., Tween 80 (Atlas Powder, U.S.A.), HCO 60 (Nikko Chemicals), polyethylene glycol, carboxymethylcellulose, sodium alginate, etc.), a preservative (e.g., methyl p-hydroxybenzoate, propyl p-hydroxybenzoate, benzyl alcohol, chlorobutanol, phenol, etc.), an isotonizing agent (e.g., sodium chloride, glycerol, sorbitol, glucose, inverted sugar, etc.) and other additives. If desired, a solubilizer (e.g., sodium salicylate, sodium acetate, etc.), a stabilizer (e.g., human serum albumin), a soothing agent (e.g., benzalkonium chloride, procaine hydrochloride, etc.) and other additives can also be added.

A dosage form for external application can be manufactured by processing the active component or components into a solid, semi-solid or liquid composition. To manufacture a solid composition, for instance, the active component or components, either as they are or in admixture with an excipient (e.g., lactose, mannitol, starch, microcrystalline cellulose, sucrose, etc.), a thickener (e.g., natural gums, cellulose derivatives, acrylic polymers, etc.), etc., are processed into powders. The liquid composition can be manufactured in substantially the same manner as the injections mentioned above. The semi-solid composition is preferably provided in a hydrous or oily gel form or an ointment form. These compositions may optionally contain a pH control agent (e.g., carbonic acid, phosphoric acid, citric acid, hydrochloric acid, sodium hydroxide, etc.), and a preservative (e.g., p-hydroxybenzoic acid esters, chlorobutanol, benzalkonium chloride, etc.), among other additives.

Suppositories can be manufactured by processing the active component or components into an oily or aqueous composition, whether solid, semi-solid or liquid. The oleaginous base that can be used includes, for instance, higher fatty acid glycerides [e.g., cacao butter, Witepsols (Dinamit-Nobel), etc.], medium-chain fatty acids [e.g., Migriols (Dinamit-Nobel), etc.], vegetable oils (e.g., sesame oil, soybean oil, cotton-seed oil, etc.), etc. The water-soluble base includes, for instance, polyethylene glycols propylene glycol, etc. The hydrophilic base includes, for instance, natural gums, cellulose derivatives, vinyl polymers, and acrylic polymers, etc.

Dosages

The dosage of the pharmaceutical composition of the present invention may be appropriately determined with reference to the dosages recommended for the respective active components and can be selected appropriately according to the recipient, the recipient's age and body weight, current clinical status, administration time, dosage form, method of administration, and combination of the active components, among other factors. For example, the dosage of the insulin sensitivity enhancer for an adult can be selected from the clinical oral dose range of 0.01 to 10 mg/kg body weight (preferably 0.05 to 10 mg/kg body weight, more preferably 0.05 to 5 mg/kg body weight) or the clinical parenteral dose range of 0.005 to 10 mg/kg body weight (preferably 0.01 to 10 mg/kg body weight, more preferably 0.01 to 1 mg/kg body weight). The other active component or components having different modes of action for use in combination can also be used in dose ranges selected by referring to the respective recommended clinical dose ranges.

The proportions of the active components in the pharmaceutical composition of the present invention can be appropriately selected according to the recipient, the recipient's age and body weight, current clinical status, administration time, dosage form, method of administration, and combination of active components, among other factors.

Pharmaceutical Combinations

The present invention includes within its scope pharmaceutical compositions includes, as an active ingredient, a therapeutically effective amount of at least one of the compounds of Formula I of the invention, alone or in combination with a pharmaceutical carrier or diluent. Optionally, compounds of the present invention can be used alone, in combination with other suitable therapeutic agents useful in the treatment of the aforementioned disorders including: anti-obesity agents; anti-diabetic agents, appetite suppressants; cholesterol/lipid-lowering agents, HDL-raising agents, cognition enhancing agents, agents used to treat neurodegeneration, agents used to treat respiratory conditions, agents used to treat bowel disorders, anti-inflammatory agents; anti-anxiety agents; anti-depressants; anti-hypertensive agents; cardiac glycosides; and anti-tumor agents.

The pharmaceutical combinations of the present invention can be formulated in combination, or separately by mixing the respective active components either together or independently with a physiologically acceptable carrier, excipient, binder, diluent, etc. When the active components are formulated independently, the respective formulations can be extemporaneously admixed using a diluent or the like and administered or can be administered independently of each other, either concurrently or at staggered times to the same subject. So, such other therapeutic agent(s) may be administered prior to, simultaneously with, or following the administration of the melanin-concentrating hormone receptor (MCHR) antagonists in accordance with the invention.

Examples of suitable anti-obesity agents for use in combination with the compounds of the present invention include melanocortin receptor (MC4R) agonists, cannabinoid receptor modulators, growth hormone secretagogue receptor (GHSR) antagonists, galanin receptor modulators, orexin antagonists, CCK agonists, GLP-1 agonists, and other Pre-proglucagon-derived peptides; NPY1 or NPY5 antagonist, NPY2 and NPY4 modulators, corticotropin releasing factor agonists, histamine receptor-3 (H3) modulators, aP2 inhibitors, PPAR gamma modulators, PPAR delta modulators, acetyl-CoA carboxylase (ACC) inhibitors, 11-β-HSD-1 inhibitors, adinopectin receptor modulators; beta 3 adrenergic agonists, such as AJ9677 (TakedaiDainippon), L750355 (Merck), or CP331648 (Pfizer) or other known beta 3 agonists as disclosed in U.S. Pat. Nos. 5,541,204, 5,770,615, 5,491,134, 5,776,983 and 5,488,064, a thyroid receptor beta modulator, such as a thyroid receptor ligand as disclosed in WO 97/21993 (U. Cal SF), WO 99/00353 (KaroBio) and WO 00/039077 (KaroBio), a lipase inhibitor, such as orlistat or ATL-962 (Alizyme), serotonin receptor agonists, (e.g., BVT-933 (Biovitrum)), monoamine reuptake inhibitors or releasing agents, such as fenfluramine, dexfenfluramine, fluvoxamine, fluoxetine, paroxetine, sertraline, chlorphentermine, cloforex, clortermine, picilorex, sibutramine, dexamphetamine, phentermine, phenylpropanolamine or mazindol, anorectic agents such as topiramate (Johnson & Johnson), CNTF (ciliary neurotrophic factor)/AXOKINE® (Regeneron), BDNF (brain-derived neurotrophic factor), leptin and leptin receptor modulators, or cannabinoid-1 receptor inverse agonists/neutral antagonists, such as SR-141716 (Sanofi) or SLV-319 (Solvay) and DGAT inhibitors such as those described in WO 2006/134317 A1 (Astra Zeneca), WO 2006/044775 A2 (Bayer), WO 2006/06019020 A1 (Sankyo), WO 2006/082010 A1 (Roche), WO 2004/047755 A2 (Japan Tobacco, Tularik), and WO 2005/0727401 A2 (Amgen, Japan Tobacco).

Examples of suitable anti-diabetic agents for use in combination with the compounds of the present invention include: insulin secretagogues or insulin sensitizers, which may include biguanides, sulfonyl ureas, glucosidase inhibitors, aldose reductase inhibitors, PPAR γ agonists such as thiazolidinediones, PPAR α agonists (such as fabric acid derivatives), PPAR δ antagonists or agonists, PPAR α/γ dual agonists, 11-β-HSD-1 inhibitors, dipeptidyl peptidase IV (DP4) inhibitors including saxagliptin, vildagliptin and sitagliptin, SGLT2 inhibitors including dapagliflozin and sergiflozin, glycogen phosphorylase inhibitors, and/or meglitinides, as well as insulin, and/or glucagon-like peptide-1 (GLP-1), GLP-1 agonist, and/or a PTP-1B inhibitor (protein tyrosine phosphatase-1B inhibitor).

The antidiabetic agent may be an oral antihyperglycemic agent preferably a biguanide such as metformin or phenformin or salts thereof, preferably metformin HCl. Where the antidiabetic agent is a biguanide, the compounds of the present invention will be employed in a weight ratio to biguanide within the range from about 0.001:1 to about 10:1, preferably from about 0.01:1 to about 5:1.

The antidiabetic agent may also preferably be a sulfonyl urea such as glyburide (also known as glibenclamide), glimepiride (disclosed in U.S. Pat. No. 4,379,785), glipizide, gliclazide or chlorpropamide, other known sulfonylureas or other antihyperglycemic agents which act on the ATP-dependent channel of the beta-cells, with glyburide and glipizide being preferred, which may be administered in the same or in separate oral dosage forms. The oral antidiabetic agent may also be a glucosidase inhibitor such as acarbose (disclosed in U.S. Pat. No. 4,904,769) or miglitol (disclosed in U.S. Pat. No. 4,639,436), which may be administered in the same or in a separate oral dosage forms.

The compounds of the present invention may be employed in combination with a PPAR γ agonist such as a thiazolidinedione oral anti-diabetic agent or other insulin sensitizers (which has an insulin sensitivity effect in NIDDM patients) such as rosiglitazone (SKB), pioglitazone (Takeda), Mitsubishi's MCC-555 (disclosed in U.S. Pat. No. 5,594,016), Glaxo-Wellcome's GL-262570, englitazone (CP-68722, Pfizer) or darglitazone (CP-86325, Pfizer, isaglitazone (MIT/J&J), JTT-501 (JPNT/P&U), L-895645 (Merck), R-119702 (Sankyo/WL), NN-2344 (Dr. Reddy/NN), or YM-440 (Yamanouchi), preferably rosiglitazone and pioglitazone.

The compounds of the present invention may be employed with a PPARα/γ dual agonist such as MK-767/KRP-297 (Merck/Kyorin; as described in Yajima, K. et al., *Am. J. Physiol. Endocrinol. Metab.,* 284:E966-E971 (2003)), AZ-242 (tesaglitazar; Astra-Zeneca; as described in Ljung, B. et al., *J. Lipid Res.,* 43:1855-1863 (2002)); muraglitazar; or the compounds described in U.S. Pat. No. 6,414,002.

The compounds of the present invention may be employed in combination with anti-hyperlipidemia agents, or agents used to treat arteriosclerosis. An example of an hypolipidemic agent would be an HMG CoA reductase inhibitor which includes, but is not limited to, mevastatin and related compounds as disclosed in U.S. Pat. No. 3,983,140, lovastatin (mevinolin) and related compounds as disclosed in U.S. Pat. No. 4,231,938, pravastatin and related compounds such as disclosed in U.S. Pat. No. 4,346,227, simvastatin and related compounds as disclosed in U.S. Pat. Nos. 4,448,784 and 4,450,171. Other HMG CoA reductase inhibitors which may be employed herein include, but are not limited to, fluvastatin, disclosed in U.S. Pat. No. 5,354,772, cerivastatin disclosed in U.S. Pat. Nos. 5,006,530 and 5,177,080, atorvastatin disclosed in U.S. Pat. Nos. 4,681,893, 5,273,995, 5,385,929 and 5,686,104, pitavastatin (Nissan/Sankyo's nisvastatin (NK-104) or itavastatin), disclosed in U.S. Pat. No. 5,011,930, Shionogi-Astra/Zeneca rosuvastatin (visastatin (ZD-4522)) disclosed in U.S. Pat. No. 5,260,440, and related statin compounds disclosed in U.S. Pat. No. 5,753,675, pyrazole analogs of mevalonolactone derivatives as disclosed in U.S. Pat. No. 4,613,610, indene analogs of mevalonolactone derivatives as disclosed in PCT application WO 86/03488, 6-[2-(substituted-pyrrol-1-yl)-alkyl)pyran-2-ones and derivatives thereof as disclosed in U.S. Pat. No. 4,647,576, Searle's SC-45355 (a 3-substituted pentanedioic acid derivative) dichloroacetate, imidazole analogs of mevalonolactone as disclosed in PCT application WO 86/07054, 3-carboxy-2-hydroxy-propane-phosphonic acid derivatives as disclosed in French Patent No. 2,596,393, 2,3-disubstituted pyrrole, furan and thiophene derivatives as disclosed in European Patent Application No. 0221025, naphthyl analogs of mevalonolactone as disclosed in U.S. Pat. No. 4,686,237, octahydronaphthalenes such as disclosed in U.S. Pat. No. 4,499,289, keto analogs of mevinolin (lovastatin) as disclosed in European Patent Application No. 0142146A2, and quinoline and pyridine derivatives disclosed in U.S. Pat. Nos. 5,506,219 and 5,691,322. In addition, phosphinic acid compounds useful in inhibiting HMG CoA reductase suitable for use herein are disclosed in GB 2205837.

The squalene synthetase inhibitors suitable for use herein include, but are not limited to, α-phosphono-sulfonates disclosed in U.S. Pat. No. 5,712,396, those disclosed by Biller et al., *J. Med. Chem.,* 31:1869-1871 (1998) including isoprenoid (phosphinyl-methyl)phosphonates as well as other known squalene synthetase inhibitors, for example, as disclosed in U.S. Pat. Nos. 4,871,721 and 4,924,024 and in Biller, S. A. et al., *Current Pharmaceutical Design,* 2:1-40 (1996).

In addition, other squalene synthetase inhibitors suitable for use herein include the terpenoid pyrophosphates disclosed by Ortiz de Montellano, P. et al., *J. Med. Chem.,* 20:243-249 (1977), the farnesyl diphosphate analog A and presqualene pyrophosphate (PSQ-PP) analogs as disclosed by Corey et al., *J. Am. Chem. Soc.,* 98:1291-1293 (1976), phosphinylphosphonates reported by McClard, R. W. et al., *J. Am. Chem. Soc.,* 109:5544 (1987) and cyclopropanes reported by Capson, T. L., Ph.D. dissertation, June, 1987, Dept. Med. Chem. U. of Utah, Abstract, Table of Contents, pp. 16, 17, 40-43, 48-51, Summary.

Other hypolipidemic agents suitable for use herein include, but are not limited to, fibric acid derivatives, such as fenofibrate, gemfibrozil, clofibrate, bezafibrate, ciprofibrate, clinofibrate and the like, probucol, and related compounds as disclosed in U.S. Pat. No. 3,674,836, probucol and gemfibrozil being preferred, bile acid sequestrants such as cholestyramine, colestipol and DEAF-Sephadex (SEC- HOLEX®, Policexide) and cholestagel (Sankyo/Geltex), as well as LIPOSTABIL® (Rhone-Poulenc), EISAI® E-5050 (an N-substituted ethanolamine derivative), imanixil (HOE-402), tetrahydrolipstatin (THL), istigmastanylphos-phorylcholine (SPC, Roche), aminocyclodextrin (Tanabe Seiyoku), Ajinomoto AJ-814 (azulene derivative), melinamide (Sumitomo), Sandoz 58-035, American Cyanamid CL-277,082 and CL-283,546 (disubstituted urea derivatives), nicotinic acid (niacin), acipimox, acifran, neomycin, p-aminosalicylic acid, aspirin, poly(diallylmethylamine) derivatives such as disclosed in U.S. Pat. No. 4,759,923, quaternary amine poly (diallyldimethylammonium chloride) and ionenes such as disclosed in U.S. Pat. No. 4,027,009, and other known serum cholesterol lowering agents.

The other hypolipidemic agent may be an ACAT inhibitor (which also has anti-atherosclerosis activity) such as disclosed in, *Drugs of the Future*, 24:9-15 (1999) (Avasimibe); Nicolosi et al., "The ACAT inhibitor, C1-1011 is effective in the prevention and regression of aortic fatty streak area in hamsters", *Atherosclerosis* (Shannon, hel.), 137(1):77-85 (1998); Ghiselli, G., "The pharmacological profile of FCE 27677: a novel ACAT inhibitor with potent hypolipidemic activity mediated by selective suppression of the hepatic secretion of ApoB 100-containing lipoprotein", *Cardiovasc. Drug Rev.*, 16(1):16-30 (1998); Smith, C. et al., "RP 73163: a bioavailable alkylsulfinyl-diphenylimidazole ACAT inhibitor", *Bioorg. Med. Chem. Lett.*, 6(1):47-50 (1996); Krause, B. R. et al., Chapter 6: "ACAT Inhibitors: Physiologic Mechanisms for Hypolipidemic and Anti-Atherosclerotic Activities in Experimental Animals", *Inflammation: Mediators and Pathways*, CRC Press, Inc., publ., Ruffolo, Jr., R. R. et al., eds., pp. 173-198 (1995); Sliskovic et al., "ACAT inhibitors: potential anti-atherosclerotic agents", *Curr. Med. Chem.*, 1(3):204-225 (1994); Stout et al., "Inhibitors of acyl-CoA: cholesterol O-acyl transferase (ACAT) as hypocholesterolemic agents. 6. The first water-soluble ACAT inhibitor with lipid-regulating activity. Inhibitors of acyl-CoA:cholesterol acyltransferase (ACAT). 7. Development of a series of substituted N-phenyl-N'-[(1-phenylcyclopentyl)-methyl]ureas with enhanced hypocholesterolemic activity", *Chemtracts: Org. Chem.*, 8(6):359-362 (1995), or TS-962 (Taisho Pharmaceutical Co. Ltd), as well as F-1394, CS-505, F-12511, HL-004, K-10085 and YIC-C8-434.

The hypolipidemic agent may be an upregulator of LDL receptor activity such as MD-700 (Taisho Pharmaceutical Co. Ltd) and LY295427 (Eli Lilly). The hypolipidemic agent may be a cholesterol absorption inhibitor preferably Schering-Plough's SCH48461 (ezetimibe) as well as those disclosed in *Atherosclerosis*, 115:45-63 (1995) and *J. Med. Chem.*, 41:973 (1998).

The other lipid agent or lipid-modulating agent may be a cholesteryl transfer protein inhibitor (CETP) such as Pfizer's CP-529,414 as well as those disclosed in WO/0038722 and in EP 818448 (Bayer) and EP 992496, and Pharmacia's SC-744 and SC-795, as well as CETi-1 and JTT-705.

The hypolipidemic agent may be an ileal $Na^+$/bile acid cotransporter inhibitor such as disclosed in *Drugs of the Future*, 24:425-430 (1999). The ATP citrate lyase inhibitor which may be employed in the combination of the invention may include, for example, those disclosed in U.S. Pat. No. 5,447,954.

The other lipid agent also includes a phytoestrogen compound such as disclosed in WO 00/30665 including isolated soy bean protein, soy protein concentrate or soy flour as well as an isoflavone such as genistein, daidzein, glycitein or equol, or phytosterols, phytostanol or tocotrienol as disclosed in WO 2000/015201; a beta-lactam cholesterol absorption inhibitor such as disclosed in EP 675714; an HDL upregulator such as an LXR agonist, a PPAR α-agonist and/or an FXR agonist; an LDL catabolism promoter such as disclosed in EP 1022272; a sodium-proton exchange inhibitor such as disclosed in DE 19622222; an LDL-receptor inducer or a steroidal glycoside such as disclosed in U.S. Pat. No. 5,698,527 and GB 2304106; an anti-oxidant such as beta-carotene, ascorbic acid, α-tocopherol or retinol as disclosed in WO 94/15592 as well as Vitamin C and an antihomocysteine agent such as folic acid, a folate, Vitamin B6, Vitamin B12 and Vitamin E; isoniazid as disclosed in WO 97/35576; a cholesterol absorption inhibitor, an HMG-CoA synthase inhibitor, or a lanosterol demethylase inhibitor as disclosed in WO 97/48701; a PPAR δ agonist for treating dyslipidernia; or a sterol regulating element binding protein-1 (SREBP-1) as disclosed in WO 2000/050574, for example, a sphingolipid, such as ceramide, or neutral sphingomyelenase (N-SMase) or fragment thereof. Preferred hypolipidemic agents are pravastatin, lovastatin, simvastatin, atorvastatin, fluvastatin, pitavastatin, rosuvastatin, and ezetimibe as well as niacin and/or cholestagel.

The compounds of the present invention may be employed in combination with anti-hypertensive agents. Examples of suitable anti-hypertensive agents for use in combination with the compounds of the present invention include beta adrenergic blockers, calcium channel blockers (L-type and/or T-type; e.g., diltiazem, verapamil, nifedipine, amlodipine and mybefradil), diuretics (e.g., chlorothiazide, hydrochlorothiazide, flumethiazide, hydroflumethiazide, bendroflumethiazide, methylchlorothiazide, trichloromethiazide, polythiazide, benzthiazide, ethacrynic acid tricrynafen, chlorthalidone, furosemide, musolimine, bumetanide, triamtrenene, amiloride, spironolactone), renin inhibitors, ACE inhibitors (e.g., captopril, zofenopril, fosinopril, enalapril, ceranopril, cilazopril, delapril, pentopril, quinapril, ramipril, lisinopril), AT-1 receptor antagonists (e.g., losartan, irbesartan, valsartan), ET receptor antagonists (e.g., sitaxsentan, atrsentan and compounds disclosed in U.S. Pat. Nos. 5,612,359 and 6,043, 265), Dual ET/AII antagonist (e.g., compounds disclosed in WO 00/01389), neutral endopeptidase (NEP) inhibitors, vasopepsidase inhibitors (dual NEP-ACE inhibitors) (e.g., omapatrilat and gemopatrilat), and nitrates.

MCHR1 antagonists could be useful in treating other diseases associated with obesity, including sleep disorders. Therefore, the compounds described in accordance with the present invention could be used in combination with therapeutics for treating sleep disorders. Examples of suitable therapies for treatment of sleeping disorders for use in combination with the compounds of the present invention include melatonin analogs, melatonin receptor antagonists, ML 1B agonists, GABA receptor modulators; NMDA receptor modulators, histamine-3 (H3) receptor modulators, dopamine agonists and orexin receptor modulators.

MCHR1 antagonists may reduce or ameliorate substance abuse or addictive disorders. Therefore, combination of cannabinoid receptor modulators with agents used to treat addictive disorders may reduce the dose requirement or improve the efficacy of current addictive disorder therapeutics. Examples of agents used to treat substance abuse or addictive disorders are: selective serotonin reuptake inhibitors (SSRI), methadone, buprenorphine, nicotine and bupropion.

MCHR1 antagonists may reduce anxiety or depression; therefore, the compounds described in accordance with the present invention may be used in combination with anti-anxiety agents or antidepressants. Examples of suitable anti-anxiety agents for use in combination with the compounds of the present invention include benzodiazepines (e.g., diazepam, lorazepam, oxazepam, alprazolam, chlordiazepoxide, clonazepam, chlorazepate, halazepam and prazepam), 5HT1A receptor agonists (e.g., buspirone, flesinoxan, gepirone and ipsapirone), and corticotropin releasing factor (CRF) antagonists.

Examples of suitable classes of anti-depressants for use in combination with the compounds of the present invention include norepinephrine reuptake inhibitors (tertiary and secondary amine tricyclics), selective serotonin reuptake inhibitors (SSRIs) (fluoxetine, fluvoxamine, paroxetine and sertraline), monoamine oxidase inhibitors (MAOIs) (isocarboxazid, phenelzine, tranylcypromine, selegiline), reversible inhibitors of monoamine oxidase (RIMAs) (moclobemide), serotonin and norepinephrine reuptake inhibitors (SNRIs) (venlafaxine), corticotropin releasing factor (CRF) receptor antagonists, alpha-adrenoreceptor antagonists, and atypical antidepressants (bupropion, lithium, nefazodone, trazodone and viloxazine).

The combination of a conventional antipsychotic drug with a MCHR1 antagonist could also enhance symptom reduction in the treatment of psychosis or mania. Further, such a combination could enable rapid symptom reduction, reducing the need for chronic treatment with antipsychotic agents. Such a combination could also reduce the effective antipsychotic dose requirement, resulting in reduced probability of developing the motor dysfunction typical of chronic antipsychotic treatment.

Examples of suitable antipsychotic agents for use in combination with the compounds of the present invention include the phenothiazine (chlorpromazine, mesoridazine, thioridazine, acetophenazine, fluphenazine, perphenazine and trifluoperazine), thioxanthine (chlorprothixene, thiothixene), heterocyclic dibenzazepine (clozapine, olanzepine and aripiprazole), butyrophenone (haloperidol), diphenylbutylpiperidine (pimozide) and indolone (molindolone) classes of antipsychotic agents. Other antipsychotic agents with potential therapeutic value in combination with the compounds in the present invention include loxapine, sulpiride and risperidone.

Combination of the compounds in the present invention with conventional antipsychotic drugs could also provide an enhanced therapeutic effect for the treatment of schizophrenic disorders, as described above for manic disorders. As used here, schizophrenic disorders include paranoid, disorganized, catatonic, undifferentiated and residual schizophrenia, schizophreniform disorder, schizoaffective disorder, delusional disorder, brief psychotic disorder and psychotic disorder not specified. Examples of suitable antipsychotic drugs for combination with the compounds in the present invention include the antipsychotics mentioned above, as well as dopamine receptor antagonists, muscarinic receptor agonists, 5HT2A receptor antagonists and 5HT2A/dopamine receptor antagonists or partial agonists (e.g., olanzepine, aripiprazole, risperidone, ziprasidone).

Methods of Preparation

The compounds of the present invention can be prepared in a number of ways well known to one skilled in the art of organic synthesis using the methods described below, together with synthetic methods known in the art of synthetic organic chemistry, or variations thereon as appreciated by those skilled in the art. Preferred methods include, but are not limited to, those described below. All references cited herein are hereby incorporated in their entirety by reference.

The novel compounds of Formula I may be prepared using the reactions and techniques described in this section. The reactions are performed in solvents appropriate to the reagents and materials employed and are suitable for the transformations being effected. Also, in the description of the synthetic methods described below, it is to be understood that all proposed reaction conditions, including solvent, reaction atmosphere, reaction temperature, duration of the experiment and workup procedures, are chosen to be the conditions standard for that reaction, which should be readily recognized by one skilled in the art. One skilled in the art of organic synthesis understands that the functionality present on various portions of the edict molecule must be compatible with the reagents and reactions proposed. Not all compounds of Formula I falling into a given class may be compatible with some of the reaction conditions required in some of the methods described. Such restrictions to the substituents, which are compatible with the reaction conditions, will be readily apparent to one skilled in the art and alternate methods must be used.

As summarized in Scheme 1, compounds of Formula I may be prepared by either of two general routes. The first approach (equation (1)) entails either alkylation or acylation of compounds of formula I (X=halogen, TsO, MsO, OH, or, alkoxy (for esters)) to generate the central bicyclic core of Formula I. Equation (2) represents an alternative approach entailing arylation of compounds of formula 2 containing a preformed central bicyclic core with arylating agents of formula 3 (L=B(OH)$_2$, halogen, or OTf). Depending on the particular molecule of Formula I being prepared, $R^1$, $R^{2a}$, $R^{2b}$, $R^{2c}$, $R^3$, $R^{3a}$ and in particular the substituent

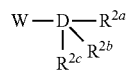

can either be fully completed prior to or elaborated after assemblage of the core structure of Formula I.

Scheme 1

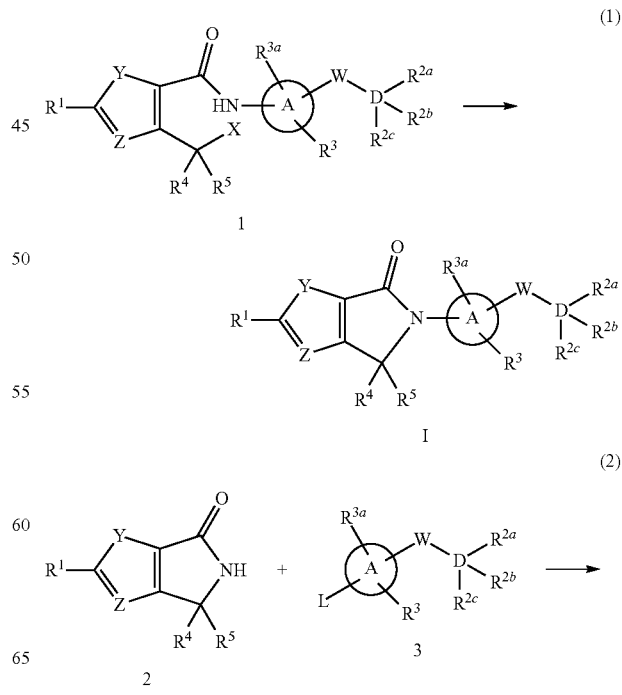

-continued

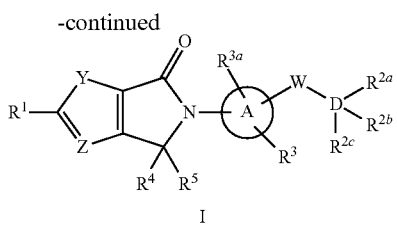

I

Syntheses of compounds of Formula I via equation (1) of Scheme 1 are specifically illustrated by the methods described in Schemes 2, 3, 4 and 5. As shown in Scheme 2, the aryl or heteroaryl amines (formula 8) forming the right-hand portion of compounds of Formula I may be synthesized by reduction of nitro aromatics of formula 7 either by catalytic hydrogenation using a catalyst such as Pd/C in a solvent such as EtOH or by reduction with $SnCl_2$ in a solvent such as EtOAe. Compounds of formula 7 where W is O or $N(R^6)$ can be prepared by alkylation of the corresponding phenols or anilines of formula 4 with an appropriate alkylating agent of formula 9 in the presence of a base such as $Cs_2CO_3$, $K_2CO_3$, NaH or LDA, in a solvent such as DMF or THF by employing procedures readily known to those skilled in the art. Alternatively compounds of formula 7 where W is O or $N(R^6)$ can be prepared by heating compounds of formula 5 either with preformed sodium salts of compounds of formula 10 where W is O or with the neat compounds of formula 10 where W is $N(R^6)$ in a solvent such as DMF. Compounds of formula 7 where W is a bond and

is linked to the nitrogen of a cyclic or bicyclic amine can be prepared by heating compounds of formula 5 with compounds of formula 10a in a solvent such as DMF.

Scheme 2

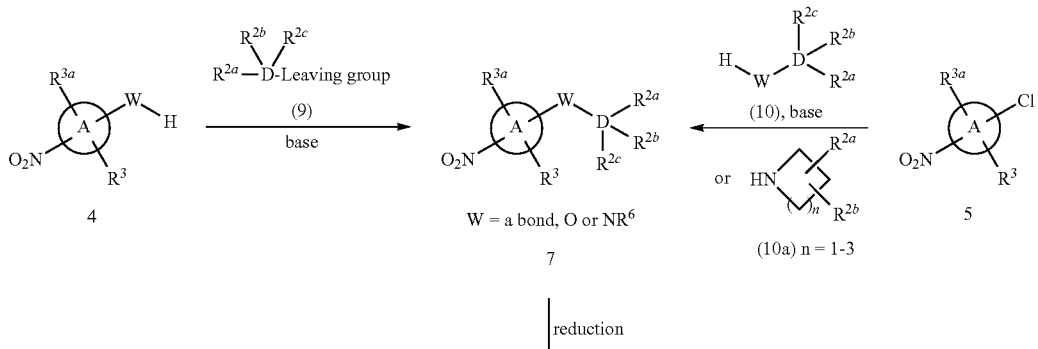

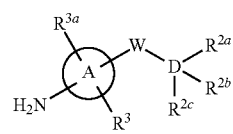

Scheme 3 describes the synthesis of the carboxylic acids (formula 1) comprising the left-hand portion of compounds of Formula I. The carboxylic acids of formula 17, where $X^a$ is Br or Cl, can be synthesized from the corresponding carboxylic acids of formula 17, where X is H, by esterification with are commercially available or can be generated from commercially available compounds of formula 12 (R=$C_1$-$C_4$alkyl such as $CH_3$ or $C_2H_5$) by direct bromination or from commercially available compounds of formula 13 by Sandmeyer reaction.

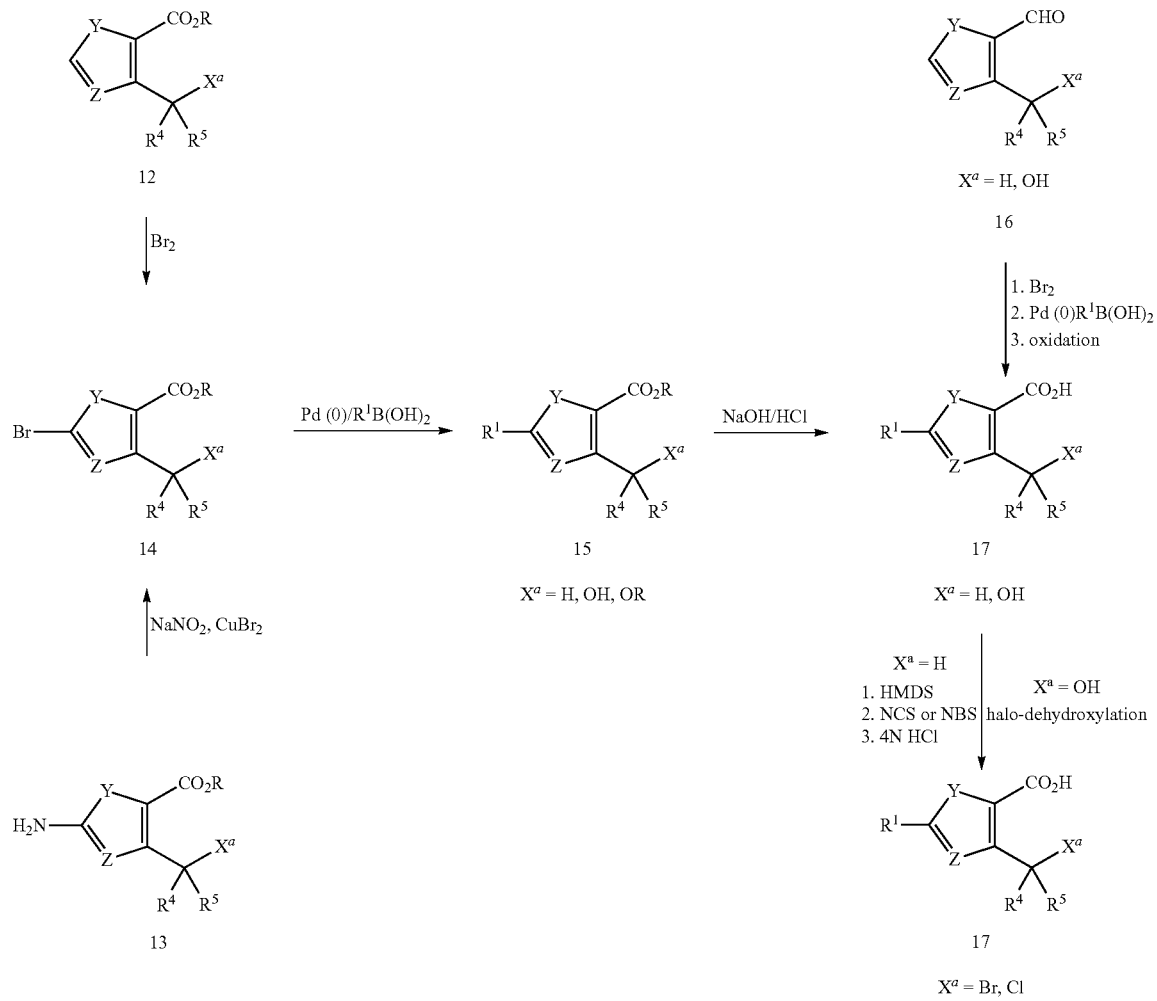

HMDS followed by halogenation with NBS or NCS initiated by AIBN, $(PhCO_2)_2$ or light and then hydrolysis with 4 N HCl. Alternatively, the carboxylic acids of formula 17, where $X^a$ is Br or Cl, can be prepared from the corresponding carboxylic acids of formula 17, where $X^a$ is OH, by halo-dehydroxylation with a reagent such as $SOCl_2$, $PCl_5$, $PCl_5$, $POCl_3$, $PBr_3$, $Ph_3PBr_2$, $Ph_3/Cl_2$, HCl, or HBr. The carboxylic acids of formula 17, where $X^a$ is H or OH, are commercially available or can be made by treating commercially available aldehydes of formula 16 with bromine followed by a Suzuki coupling with boronic acids and conventional oxidation with an oxidant such as potassium permanganate, sodium chlorite, Jones reagent, silver oxide etc. Alternatively, the carboxylic acids of formula 17, where $X^a$ is H or OH, can be formed by saponification of esters of formula 15 with a base such as NaOH or KOH, in solvent such as EtOH or MeOH, followed by acidification with HCl or $H_2SO_4$. Esters of formula 15 are commercially available or can be synthesized from compounds of formula 14 via Suzuki reaction. Compounds of formula 14

Alternatively, esters of formula 15 can be made by cyclization to form 5-membered heterocycles with existing $R^1$ using synthetic transformations known to those skilled in the art, exemplified in Scheme 4. Oxazole esters of formula 15, where Y is O and Z is N and r is H, OH, or alkoxy (for esters), can be prepared by reaction of acyl amino acids with oxalyl chloride followed by addition of alcohols (Crooks et al., *J. Chem. Soc., Chem. Commun.*, 2335 (1995)).

Scheme 4

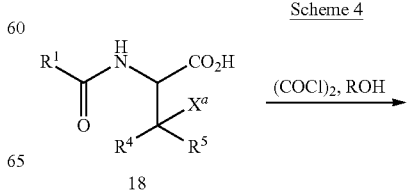

51
-continued

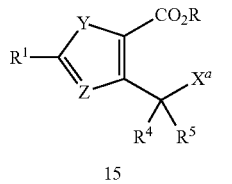

15

Y = O, Z = N

52
-continued

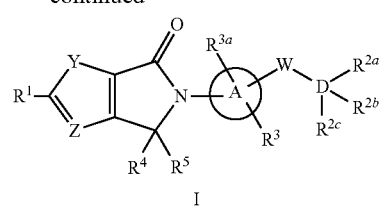

I

Scheme 5 shows both the amide bond formation between the aromatic amines of formula 8 with the carboxylic acids of formula 17 to generate compounds of formula 1 using one of the variety procedures conducive to amide formation known to those skilled in the arts, including but not limited to EDC, DIC, PyBop, or BOP-Cl, and the subsequent conversion of compounds of formula 1 to compounds of Formula I. Compounds of Formula I may be prepared by either intramolecular alkylation, or acylation of compounds of formula 1. Suitable reaction conditions comprise stirring 1 in the presence of a base such as NaH, KOtBu, $K_2CO_3$, $Na_2CO_3$, KF, $K_3PO_4$, $Et_3N$, $iPr_2Net$ and $NaOH/Bu_4NBr$, where $X^a$=halogen, OTs, OMs, alkoxy (for esters), by using coupling condition, such as EDC or PyBop, or by employing Mitsunobu condition where X=OH. Additionally, interconversion of X groups between halogen, OTs, OMs, alkoxy (for esters), and OH can achieved by one of the variety procedures known to those skilled in the arts.

Scheme 6 outlines the synthesis of compounds of Formula I by the alternative approach 2 of Scheme 1. Compounds of Formula I may be prepared by arylation of compounds of formula 2 either with an aryl boronic acid of formula 3 (L=B(OH)$_2$) in the presence of Cu(OAc)$_2$ in a solvent such as $CH_2Cl_2$ containing molecular sieves or alternatively with aryl halides of formula 3a (L=halogen, OTf) catalyzed by CuI or Pd complex with suitable ligands. Compounds of formula 2 can be generated by following the procedure described in Scheme 4 via amide formation of acids of formula 17 ($X^a$ is halogen, OTs, OMs, OH, or alkoxy (for esters)) with ammonia and the subsequent intermolecular alkylation or acylation. Aryl boronic acids of formula 3 (L=B(OH)$_2$) are commercially available or can be formed by either treating commercially available compounds of formula 3a (L=halogen) with n-BuLi in a solvent such as THF followed by sequential addition of B(OMe)$_3$ and then hydrolysis with hydrochloric acid or alternatively stirring 3a (L=halogen, OTf) with diborate 24 in the presence of a Pd catalyst followed by transesterification with benzaldehyde in the presence of hydrochloric acid. It should be noted the synthesis of compounds of Formula I via this approach can be greatly facilitated if the substituent

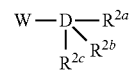

of compound of formula 3 is replaced with W capped with a protecting group which, after transformation of 3 to compounds of Formula I, is sequentially deprotected and alkylated to generate the fully elaborated appendage

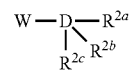

using methods known to those skilled in the arts.

Scheme 5

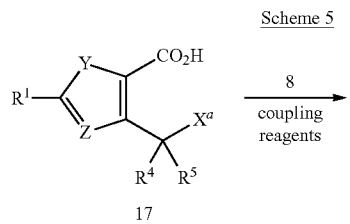

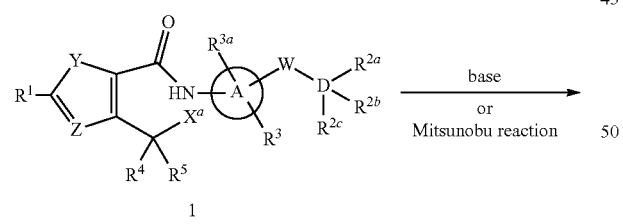

Scheme 6

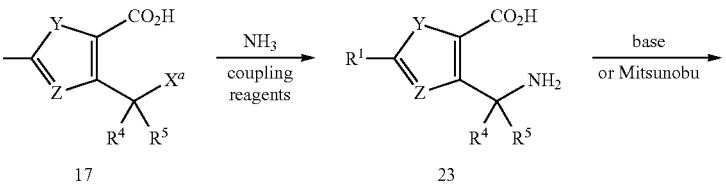

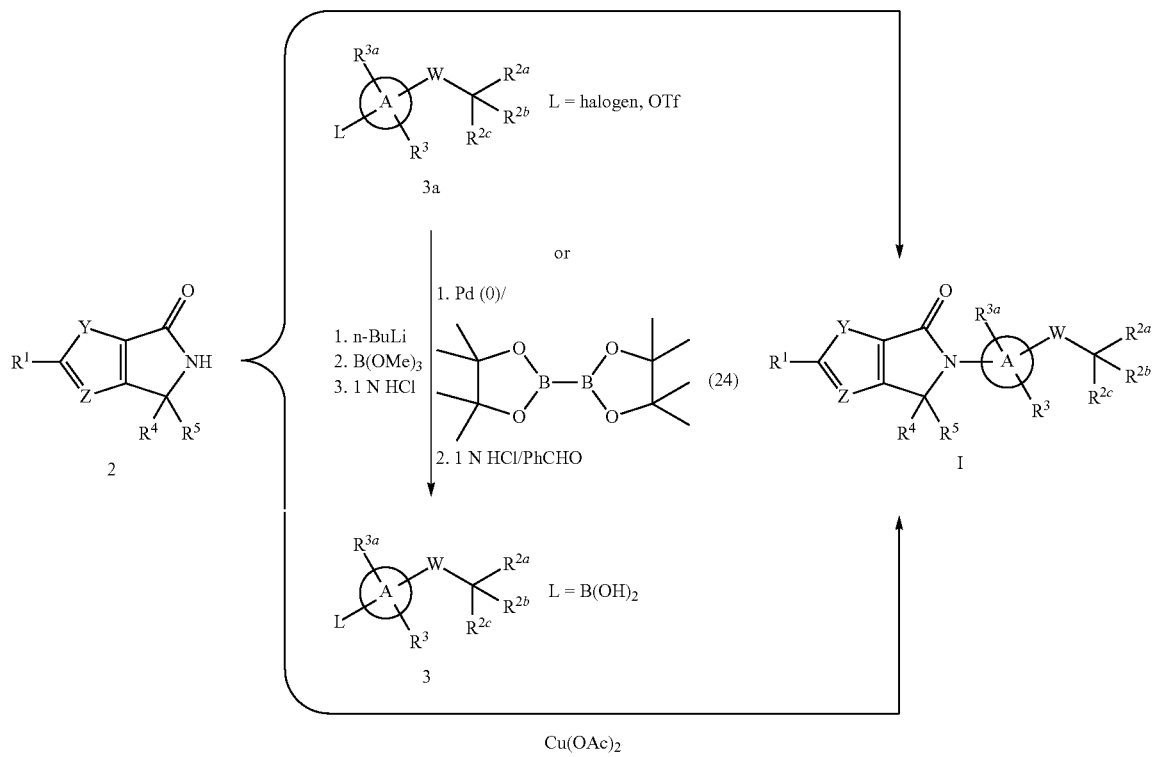

Prodrugs, Salts, Stereoisomers and Isotopes

The term "prodrug" encompasses both the term "prodrug esters" and the term "prodrug ethers". The term in "prodrug esters" as employed herein includes esters and carbonates formed by reacting one or more hydroxyls of compounds of Formula I with either alkyl, alkoxy, or aryl substituted acylating agents or phosphorylating agent employing procedures known to those skilled in the art to generate acetates, pivalates, methylcarbonates, benzoates, amino acid esters, phosphates and the like.

Examples of such prodrug esters include

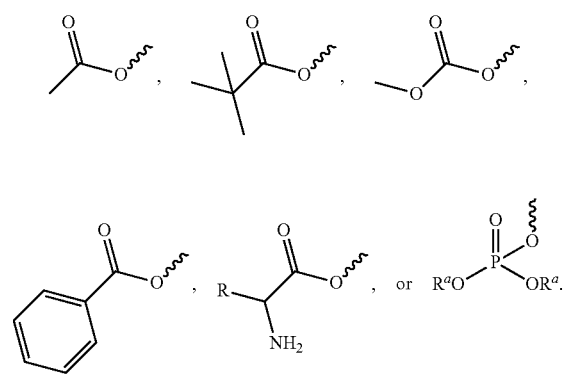

The term "prodrug ethers" include both phosphate acetals and O-glucosides. Representative examples of such prodrug ethers include In the above formulae, R is alkyl or H and $R^a$ is H, alkyl, or benzyl.

The compounds of Formula I can be present as salts, which are also within the scope of this invention. Pharmaceutically acceptable (i.e., non-toxic, physiologically acceptable) salts are preferred. If the compounds of Formula I have, for example, at least one basic center, they can form acid addition salts. These are formed, for example, with strong inorganic acids, such as mineral acids, for example sulfuric acid, phosphoric acid or a hydrohalic acid, with organic carboxylic acids, such as alkanecarboxylic acids of 1 to 4 carbon atoms, for example acetic acid, which are unsubstituted or substituted, for example, by halogen as chloroacetic acid, such as saturated or unsaturated dicarboxylic acids, for example oxalic, malonic, succinic, maleic, fumaric, phthalic or terephthalic acid, such as hydroxycarboxylic acids, for example ascorbic, glycolic, lactic, malic, tartaric or citric acid, such as amino acids, (for example aspartic or glutamic acid or lysine or arginine), or benzoic acid, or with organic sulfonic acids, such as ($C_1$-$C_4$) alkyl or arylsulfonic acids which are unsubstituted or substituted, for example by halogen, for example methyl- or p-toluene-sulfonic acid. Corresponding acid addition salts can also be formed having, if desired, an additionally present basic center. The compounds of Formula I having at least one acid group (for example COOH) can also form salts with bases. Suitable salts with bases are, for example, metal salts, such as alkali metal or alkaline earth metal salts, for example sodium, potassium or magnesium salts, or salts with ammonia or an organic amine, such as morpholine, thiomorpholine, piperidine, pyrrolidine, a mono, di or tri-lower alkylamine, for example ethyl, tert-butyl, diethyl, diisopropyl, triethyl, tributyl or dimethyl-propylamine, or a mono, di or trihydroxy lower alkylamine, for example mono, di or triethanolamine. Corresponding internal salts may furthermore be formed. Salts which are unsuitable for pharmaceutical uses but which can be employed, for example, for the isolation or purification of free compounds of Formula I or their pharmaceutically acceptable salts, are also included.

Preferred salts of the compounds of Formula I which contain a basic group include monohydrochloride, hydrogensulfate, methanesulfonate, phosphate, nitrate or acetate.

Preferred salts of the compounds of Formula I which contain an acid group include sodium, potassium and magnesium salts and pharmaceutically acceptable organic amines.

All stereoisomers of the compound of the instant application are contemplated, either in admixture or in pure or substantially pure form. The compound of the present application can have asymmetric centers at any of the carbon atoms including any one of the R substituents. Consequently, compound of Formula I can exist in enantiomeric or diastereomeric forms or in mixtures thereof. The processes for preparation can utilize racemates, enantiomers or diastereomers as starting materials. When diastereomeric or enantiomeric products are prepared, they can be separated by conventional methods for example, chromatographic or fractional crystallization.

The present invention is intended to include all isotopes of atoms occurring in the present compounds of the invention. Isotopes include those atoms having the same atomic number but different mass numbers. By way of general example and without limitation, isotopes of hydrogen include deuterium and tritium. Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed.

Abbreviations

The following abbreviations are employed herein:

| | |
|---|---|
| Ph = | phenyl |
| Bn = | benzyl |
| t-Bu = | tertiary butyl |
| Me = | methyl |
| NBS = | N-bromosuccinimide |
| NCS = | N-chlorosuccinimide |
| EDC = | 1-(3-dimethylaminopropyl)-3-ethylcarbodiimide HCl |
| DIC = | 2-dimethylaminoisopropyl chloride HCl |
| PyBop = | purum |
| BOP-Cl = | bis(2-oxo-3-oxazolidinyl)-phosphinic chloride |
| MCPBA = | |
| OTs = | Otosyl |
| OMs = | Omesyl |
| Tf = | triflate |
| AIBN = | 2,2'-azobisisobutyronitrile |
| Et = | ethyl |
| TMS = | trimethylsilyl |
| TBS = | tert-butyldimethylsilyl |
| THF = | tetrahydrofuran |
| $Et_2O$ = | diethyl ether |
| EtOAc = | ethyl acetate |
| DMF = | dimethyl formamide |
| MeOH = | methanol |
| EtOH = | ethanol |
| i-PrOH = | isopropanol |
| HOAc or AcOH = | acetic acid |
| TFA = | trifluoroacetic acid |
| i-$Pr_2$NEt = | diisopropylethylamine |
| $Et_3N$ = | triethylamine |
| DMAP = | 4-dimethylaminopyridine |
| $NaBH_4$ = | sodium borohydride |
| n-BuLi = | n-butyllithium |
| Pd/C = | palladium on carbon |
| KOH = | potassium hydroxide |
| NaOH = | sodium hydroxide |
| LiOH = | lithium hydroxide |
| $K_2CO_3$ = | potassium carbonate |
| $NaHCO_3$ = | sodium bicarbonate |
| Ar = | argon |
| $N_2$ = | nitrogen |
| min = | minute(s) |
| h or hr = | hour(s) |
| L = | liter |
| mL = | milliliter |
| μL = | microliter |
| g = | gram(s) |
| mg = | milligram(s) |
| mol = | moles |
| mmol = | millimole(s) |
| meq = | milliequivalent |
| RT = | room temperature |
| sat or sat'd = | saturated |
| aq. = | aqueous |
| TLC = | thin layer chromatography |
| HPLC = | high performance liquid chromatography |
| LC/MS = | high performance liquid chromatography/mass spectrometry |
| MS or Mass Spec = | mass spectrometry |
| NMR = | nuclear magnetic resonance |
| mp = | melting point |
| B = | boron |

EXAMPLES

The following Examples serve to better illustrate, but not limit, some of the preferred embodiments of the application.

Except as indicated, the following analytical HPLC method was utilized: PHENOMENEX® Luna C18 S5 column 5μ, 4.6×50 mm, 4 min gradient at 4 mL/rain, 10% MeOH/90% $H_2O$/0.2% $H_3PO_4$ to 90% MeOH/10% $H_2O$/ 0.2% $H_3PO_4$ with 1 min hold at the end of the gradient, UV detection at 220 nM.

Preparative HPLC conditions employed PHENOMENEX® Luna Axia columns using gradient elutions with appropriate mixtures of 10% MeOH/90% $H_2O$/0.1% TFA to 90% MeOH/10% $H_2O$/0.1% TFA. On occasion, mixtures of 10% MeCN/90% $H_2O$/0.1% TFA and 90% MeCN/10% $H_2O$/ 0.1% TFA were employed. If the molecule contained an acid sensitive component, the TFA was omitted.

Mass spectral data were obtained using a Waters ZMD single quadrapole mass spectrometer. Typical conditions were PHENOMENEX® reverse phase C18 column 4.6×50 min, 4 min gradient, 10% MeOH/90% H₂O/0.1% TFA to 90% MeOH/10% H₂O/0.1% TFA, 1 min hold; 4 mL/min, UV detection at 220 nm.

Example 1

2-(4-Chlorophenyl)-5-(4-(2-hydroxy-2-methylpropoxy)-3-methoxyphenyl)-4H-thieno[3,2-c]pyrrol-6(5H)-one

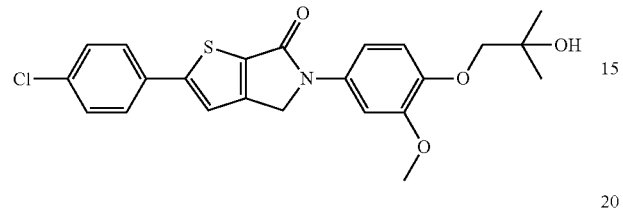

Part A. 5-Bromo-3-methylthiophene-2-carbaldehyde

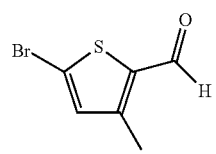

Following the preparation as described in U.S. Publication No. 2006/0199836, Br₂ (3.67 mL, 71.3 mmol) was added to a solution of 3-methylthiophene-2-carbaldehyde (8.55 mL, 71.3 mmol) in chloroform (59.4 mL) dropwise at 0° C. over a period of 20 min. The reaction was allowed to slowly warm to room temperature and stir for 2 h. The brown/red solution was diluted with 150 mL of CH₂Cl₂ and washed with water, 1.5 M K₂HPO₄ and brine. The organic layer was dried over anhydrous Na₂SO₄ and concentrated. The residue was purified by flash chromatography (silica gel, hexanes:EtOAc, 100:0 to 50:50) to afford 13.9 g (72% yield) of the title compound as a brown solid: ¹H NMR (400 MHz, CDCl₃) δ 9.91 (s, 1H), 6.97 (s, 1H), 2.54 (s, 3H); HPLC retention time: 2.718 min., LCMS (ES): m/z 207 [M+H]⁺.

Part B. 5-(4-Chlorophenyl)-3-methylthiophene-2-carbaldehyde

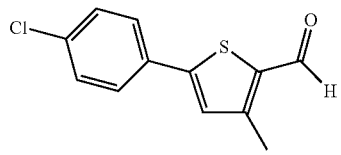

A solution of Pd(PPh₃)₄ (0.563 g, 0.488 mmol) in degassed DME (30.0 mL) and a 2.0 M solution of Na₂CO₃ (19.51 mL, 39.0 mmol) was sequentially added to Part A compound (5.000 g, 19.51 mmol). After stirring at RT for 5 min, a solution of 4-chlorophenylboronic acid (3.81 g, 24.38 mmol) in degassed EtOH (30.0 mL) was added; the flask purged with argon and heated at 90° C. for 3 h. Upon cooling, the reaction mixture was filtered through a pad of CELITE®. The organic layer was separated, dried over anhydrous Na₂SO₄, and concentrated. The residue was purified by flash chromatography (silica gel, hexanes:EtOAc, 100:0 to 25:75) to afford 3.65 g (75% yield) of the title compound as a yellow solid: ¹H NMR (500 MHz, CDCl₃) δ 9.95 (1H, s), 7.50 (2H, d, J=8.3 Hz), 7.32 (2H, d, J=8.3 Hz), 7.09 (1H, s), 2.52 (3H, s); HPLC retention time: 3.631 min.; LCMS (ES): m/z 237 [M+H]⁺.

Part C.
5-(4-Chlorophenyl)-3-methylthiophene-2-carboxylic acid

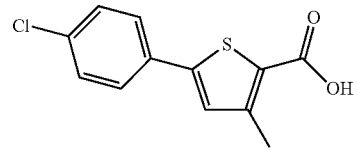 [SMILES: Cc1cc(-c2ccc(Cl)cc2)sc1C(=O)O]

To a 0° C. mixture of Part B compound (3.500 g, 14.79 mmol), sodium dihydrogen phosphate (6.09 mL, 15.23 mmol) and 30% H₂O₂ (1.586 mL, 15.52 mmol) in MeCN (148 mL) was added a solution of sodium chlorite (2.257 g, 19.96 mmol) in 20.3 mL water dropwise over a period of 2 h. The reaction was allowed to slowly warm to RT and stir for 7 h. Sodium sulfite (0.186 g, 1.479 mmol) was added and the mixture stirred at RT for 15 min whereupon it was acidified to pH=2 with 1 N HCl. The solid formed was filtered, washed well with water and air dried under vacuum to afford 3.60 g (91% yield) of the title compound as a light yellow solid that was carried forward without further purification: ¹H NMR (400 MHz, DMSO-d₆) δ 13.04 (1H, s), 7.73 (2H, d, J=8.4 Hz), 7.45-7.56 (3H, m), 2.48 (3H, s); HPLC retention time: 3.471 min.; LCMS (ES): m/z 253 [M+H]⁺.

Part D. 3-(Bromomethyl)-5-(4-chlorophenyl) thiophene-2-carboxylic acid

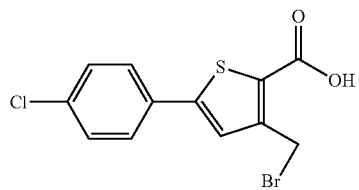 [SMILES: O=C(O)c1sc(-c2ccc(Cl)cc2)cc1CBr]

To a suspension of Part C product (1.000 g, 3.96 mmol) in CCl₄ (3.41 mL) was added 1,1,1,3,3,3-Hexamethyldisilazane (0.504 mL, 2.374 mmol) and the reaction was allowed to reflux for 1 h. Upon cooling, the solvent was removed in vacuo and the residue was dissolved in CCl₄ (3.41 mL). NBS (0.704 g, 3.96 mmol) and AIBN (0.032 g, 0.198 mmol) were added and the reaction was allowed to reflux. After one hour, an additional 0.176 g (0.99 mmol) of NBS and 1 mg (0.050 mmol) of AIBN were added and the reaction refluxed for an additional 1 h. The reaction was cooled, filtered, and concentrated. The residue was taken up in a mixture of THF (4.0 mL) and 4 N HCl (1.0 mL) and allowed to reflux for 10 min. After cooling to RT, the solvent was removed and the resulting orange oil was triturated with ether (3×25 mL) to afford 805 mg (61% yield) of the title compound as a light yellow solid upon air drying under vacuum. This material was carried forward without further purification: ¹H NMR (400 MHz, DMSO-d₆) δ 7.77 (2H, d, J=8.8 Hz), 7.73 (1H, s), 7.54 (2H, d, J=8.4 Hz), 4.97 (2H, s); HPLC retention time: 3.910 min.; LC MS (ES): m/z 251 [M–HBr+H]⁺.

Part E. 3-(Chloromethyl)-5-(4-chlorophenyl)-N-(4-(2-hydroxy-2-methylpropoxy)-3-methoxyphenyl)thiophene-2-carboxamide

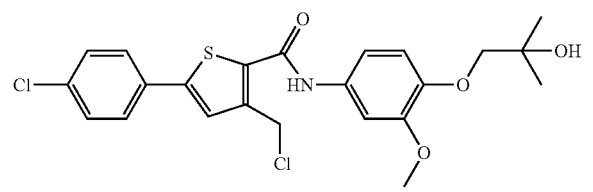

A solution of Part D product (2.00 g, 6.03 mmol), 1-(4-amino-2-methoxyphenoxy)-2-methylpropan-2-ol (1.34 mg, 6.33 mmol) (prepared as described in U.S. Publication No. 2007/0093509 A1) and EDC (1.16 g, 6.03 mmol) in DMF (30.2 mL) was allowed to stir at RT for 16 h. The reaction mixture was diluted with water (100 mL) and extracted with EtOAc (3×75 mL). The combined organic layers were washed with water, brine, dried over anhydrous Na₂SO₄, and concentrated under vacuum to afford 2.7 g of the title compound as a crude brown solid which was carried forward without further purification (It can be purified by flash chromatography if necessary): HPLC retention time: 3.910 min.; LCMS (ES): m/z 480 [M+H]⁺.

Part F. 2-(4-Chlorophenyl)-5-(4-(2-hydroxy-2-methylpropoxy)-3-methoxyphenyl)-4H-thieno[3,2-c]pyrrol-6(5H)-one

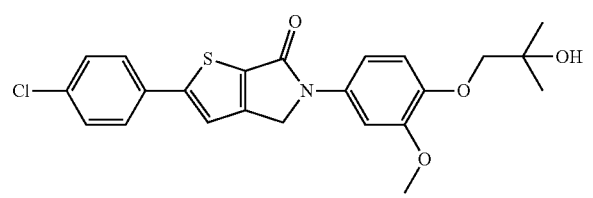 [SMILES: COc1cc(N2Cc3cc(-c4ccc(Cl)cc4)sc3C2=O)ccc1OCC(C)(C)O]

A solution of Part E product (2.70 g, 5.63 mmol) and K₂CO₃ (0.834 g, 6.03 mmol) in DMF (225 mL) was allowed to stir at RT for 2 h. Upon completion, the reaction mixture was diluted water (500 mL) and the solid formed was collected by vacuum filtration. The resulting yellow solid was triturated with MeOH (5×25 mL) followed by ether (2×25 mL) then air dried under vacuum to afford 1.53 g (56% yield) of the title compound as a yellow solid which was not purified further: ¹H NMR (500 MHz, CD₂Cl₂) δ 7.50-7.57 (m, 3H), 7.24 (s, 1H) 7.35 (d, J=8.3 Hz, 2H), 6.97 (dd, J=8.8, 2.2 Hz, 1H), 6.86 (d, 8.8 Hz, 1H), 4.69 (s, 2H), 3.81 (s, 3H), 3.73 (s, 2H), 1.23 (s, 6H). HPLC retention time: 3.893 min.; LCMS (ES): m/z 444 [M+H]⁺.

Examples 2 to 18

The following examples were prepared following the method described in Example 1. Except as indicated in the table or shown in the following methods, NH₂Ar (8) or NH₂ heteroaryl (8) was prepared as described in U.S. Publication No. 2007/0093509 A1.

Aniline 1

(R)-2-(4-Amino-2-methoxyphenoxy)-1-cyclopropylethanol

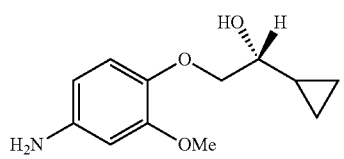 [SMILES: COc1cc(N)ccc1OC[C@H](O)C1CC1]

Part A. 2-Bromo-1-cyclopropylethanone

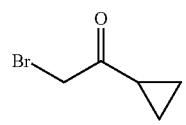

Following the procedure described by Calverley, M. J. et al., Tetrahedron Lett., 43:4609 (1987), Br₂ (21.72 mL, 422 mmol) was added over 5 min to a solution of 1-cyclopropylethanone (35.44 g, 421 mmol) in MeOH (250 mL) at 0° C. Decolorization occurred as the resulting dark orange solution was stirred at <10° C. for 50 min. After removal of the ice bath, the mixture was stirred at 20° C. for another 0.5 h; whereupon, 30 ml of water was added. After stifling an additional 15 min, the reaction was diluted with 90 ml water prior to extraction with 200 mL of Et₂O (4×). The combined organic layers were sequentially washed with 1M Na₂CO₃ (150 ml) and brine (100 ml) before drying over anhy. MgSO₄. After filtration and concentration using a rotary evaporator, the crude product was obtained as colorless oil. Subsequent distillation at 13 mm Hg yielded 40.9 g of 2-bromo-1-cyclopropylethanone as a colorless oil by 58-62° C. ¹H NMR (500 MHz, CDCl₃) δ 0.95-1.03 (m, 2H), 1.08-1.15 (m, 2H), 2.13-2.21 (m, 1H), 4.00 (s, 2H).

Part B.
1-Cyclopropyl-2-(2-methoxy-4-nitrophenoxy)ethanone

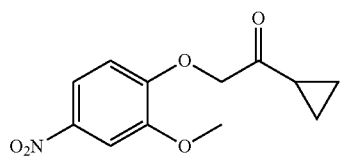 [SMILES: COc1cc([N+](=O)[O-])ccc1OCC(=O)C1CC1]

An orange suspension of 4-nitroguaiacol potassium salt hydrate (31.7 g, 153 mmol) and 2-bromo-1-cyclopropylethanone (29.4 g, 180 mmol), prepared in part A, in DMF (310 mL) was heated at 80° C. for 1 h. LC-MS analysis revealed the conversion to product was complete. The resulting yellow reaction mixture was diluted with water (932 ml) and stirred for 4 hr as the mixture cooled to 20° C. Subsequent filtration yielded a yellow filter cake which after washing 3× with 150 mL of H$_2$O and air drying yielded 34.6 g of 1-cyclopropyl-2-(2-methoxy-4-nitrophenoxy)ethanone as a light yellow solid. M.P. 112-113° C. $^1$H NMR (400 MHz, CDCl$_3$): δ 0.95-1.03 (m, 2H), 1.13-1.18 (m, 2H), 2.15-2.23 (m, 1H), 3.95 (s, 3H), 4.86 (s, 2H), 6.73 (d, J=8.7 Hz, 1H), 7.75 (d, J=2.7 Hz, 1H), 7.82 (dd, J=8.7, 2.7 Hz, 1H). $^{13}$C NMR (100 MHz, CDCl$_3$) δ ppm 205.2, 152.7, 149.1, 117.3, 111.6, 106.9, 73.5, 56.3, 17.1, 12.0. HPLC: 5.8 min retention time, 98.7% API; ZORBAX® column SB C18 4.6×75 mm; flow rate 2.5 ml/min; Gradient solvent system: from 100% A:0% B to 0% A:100% B for 8 min (Solvent A: 10% MeOH−90% H$_2$O=0.2% H$_3$PO$_4$; Solvent B: 90% MeOH−10% H$_2$O+0.2% H$_3$PO$_4$) Detection at 220 nm. LC/MS: m/e 252.3 (M+H); 4 min gradient; 2.35 min retention.

Part C. (R)-1-Cyclopropyl-2-(2-methoxy-4-nitrophenoxy)ethanol (Part C (R)-Alcohol)

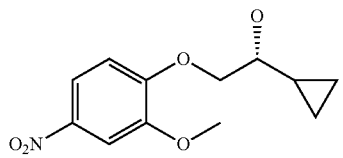

Part C. Preparation (1)

To a yellow suspension of 1-cyclopropyl-2-(2-methoxy-4-nitrophenoxy)ethanone (34.6 g, 138 mmol), prepared in Part B, in EtOH (356 mL) at 0° C. was added NaBH$_4$ (3.1 g, 82 mmol) over 15 min. After removal of the ice bath, the temperature was not allowed to exceed 20° C. while the reaction stirred for 35 additional min. During this period the color progressively became a deeper yellow hue. The stirred reaction was cooled to ~10° C. using an ice bath prior to cautious slow addition of HOAc (12 mL, 210 mmol) to minimize the rate of evolution of H$_2$ gas. After stirring for 0.5 h following cessation of gas evolution, the yellow suspension was concentrated under vacuum using a rotary evaporator to remove ~300 mL of EtOH. Filtration yielded a light yellow solid (28.7 g) after washing with H$_2$O and air drying. Subsequent further concentration of the filtrate to remove most of the EtOH resulted in more precipitate forming which, after filtration as described previously, corresponded to an additional 4.9 g of desired product. The two fractions were combined to yield 33.6 g of racemic 1-cyclopropyl-2-(2-methoxy-4-nitrophenoxy)ethanol.

Racemic 1-cyclopropyl-2-(2-methoxy-4-nitrophenoxy)ethanol (45.1 g, mmol) in 2/1 MeCN/i-PrOH (451 mL) was resolved by chiral chromatography resolution using a CHIRALPAK® AD-H (3×25 cm, 5 µm) column under the Chiral-SFC conditions. The chromatographic conditions employed an 85/15 mixture of CO$_2$/i-PrOH as the mobile solvent with a flow rate of 130 mL/min at 35° C. with the BPR pressure maintained at 100 bar and detector wavelength at 234 nM. Each 0.7 mL injection required a run time of 7 min. The chiral purity of the R enantiomer was determined to be greater than 99.9% at 234 nm based on SFC/UV area % using analytical SFC conditions. Concentration of the resultant eluant under vacuum using a rotary evaporator yielded (R)-1-cyclopropyl-2-(2-methoxy-4-nitrophenoxy)ethanol as yellow oil. Subsequent dissolution in 150 ml EtOH and reconcentration yielded the title compound in the form of a yellow oil which solidified to form a light yellow solid (20.9 g) upon drying under high vacuum overnight. M.P. 77° C. $^1$H NMR (400 MHz, CDCl$_3$): δ 0.30-0.37 (m, 1H), 0.42-0.50 (m, 1H), 0.55-0.69 (m, 2H), 0.97-1.08 (m, 1H), 2.40-2.70 (bs, 1H), 3.41 (ddd, J=8.3, 8.3, 2.7 Hz, 1H), 3.93 (s, 3H), 4.10 (dd, J=9.3, 8.0 Hz, 1H), 4.23 (dd, J=9.3, 2.7 Hz, 1H), 6.95 (d, J=8.8 Hz, 1H), 7.74 (d, J=2.2 Hz, 1H), 7.89 (dd, J=8.8, 2.2 Hz, 1H). $^{13}$C NMR (100 MHz, CDCl$_3$) δ 153.7, 149.2, 141.7, 117.6, 111.5, 106.7, 74.4, 73.5, 56.2, 13.4, 2.7, 2.0. HPLC: 6.26 min retention time, 98.7% API; ZORBAX® column SB C18 4.6×75 mm; flow rate 2.5 ml/min; Gradient solvent system: from 100% A:0% B to 0% A:100% B for 8 min (Solvent A: 10% MeOH 90% H$_2$O=0.2% H$_3$PO$_4$; Solvent B: 90% MeOH−10% H$_2$O+0.2% H$_3$PO$_4$) Detection at 220 run. LC/MS: m/e=254.3 (M+H).

Chiral HPLC: Optical purity was assessed by HPLC chromatography at 35° C. using a CHIRALPAK® AD-H, 25×4.6 mm ID; 5 µm column for which the mobile phase was an 80/20 mixture of CO$_2$/isopropanol at 100 bars with a flow rate of 2 mL/min. Under these conditions the desired R enantiomer eluted in 7 minutes followed by the S enantiomer at 8.5 min.

Part C. Preparation (2)

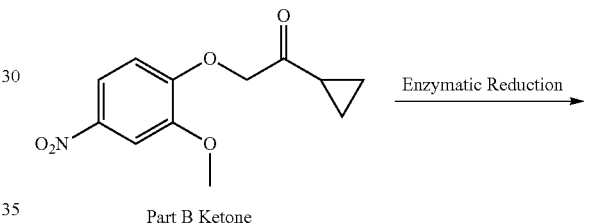

Part B Ketone

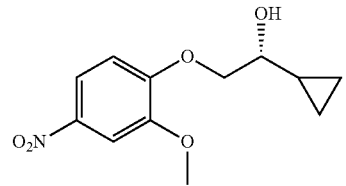

Part C (R)-Alcohol
(R)-1-Cyclopropyl-2-(2-methoxy-4-nitrophenoxy)ethanol

Two commercially available ketoreductases from Biocatalytics, Inc., namely KRED-112 and KRED-113, were employed for the reduction of Part B ketone to corresponding Part C (R)-alcohol. The reactions were carried out at 30° C. in 100 mM phosphate buffer, pH 7.5 with substrate input of 4-10 mg/mL and enzyme input of 2-5 mg/mL. Isopropanol and NADP were used to regenerate cofactor NADPH required for the reduction process. Glucose dehydrogenase, NADP and glucose were also used to regenerate cofactor NADPH required for this reduction. Both reversed phase and chiral HPLC methods were established for determination of substrate and product concentrations and the enantiomeric excess of product.

Two ketoreductases, KRED 112 and KRED 113, gave 97-99% yields and 99.5% enantiomeric excess for the desired Part C (R)-alcohol. Results are as shown in the table below:

Reduction of Part B Ketone to Part C (R)-Alcohol (IPA-200 mL, pH 7.5, 30° C.)

| Entry | Part B Ketone in DMSO (0.2 mg/μL) | Enzyme Solution (20 mg/mL) | Buffer | % Conversion (% ee of Part C (R)-alcohol) | | |
|---|---|---|---|---|---|---|
| | | | | 24 h | 48 h | 66 h |
| KRED-113 | 4 mg/20 μL | 2 mg/100 μL | 700 μL | 95.8 | 99.1 (ee 99.6%) | 99.7 (ee 99.6%) |
| KRED-113 | 10 mg/50 μL | 5 mg/250 μL | 550 μL | 69.3 | 88.4 (ee 99.4%) | 97.4 (ee 99.5%) |
| KRED-112 | 4 mg/20 μL | 2 mg/100 μL | 750 μL | 68 | 84 (99.4%) | 97% (ee 99.6%) |

Employing the above procedure, two ketoreductases from Julich Enzyme Inc., namely ADH kit part 5/9 and ADH kit part 6/9, gave 44-48% yields and 100% enantiomeric excess for the (S)-alcohol.

HPLC Method

Reversed phase Chiral HPLC for determination of enantiomeric excess:

Column: CHIRALPAK® IC 5 μm, 250×4.6 mm

Solvent: Gradient of solvent A and B

A: 0.05% TFA in Water Methanol (80:20)

B: 0.05% TFA in Acetonitrile—Methanol (80:20)

Start 30% B, 25 min 55% B, 30 min 100% B, 40 min 100% B

Total Time 40 min, Flow Rate: 0.5 ml/min, Room Temperature

UV detection 240 and 340 nm. 02.22

The retention times are:

(S)-Alcohol Retention time: 26.74 min (R)-Alcohol Retention time: 24.9 min

Part B Ketone peak at 32.74 min

Part C. Preparation (3): Selective Enzymatic Reduction Process

Use of *Candida sonorensis* (SC16117) for the Reduction of Part 13 Ketone: *Candida sonorensis* (SC16117) (ATCC #56511) was used for the reduction of Part B ketone to the corresponding Part C (R)-alcohol. Cultures were grown for 48 hours at 28° C. on a medium containing 2% glucose, 2% malt extract, 1% yeast extract, and 0.5% peptone. Cells were harvested by centrifugation and cells were suspended in 50 mM potassium phosphate buffer, pH 7.0 at 10% (w/v) cell concentrations. Cells were supplemented with 5 mg/mL of substrate, 50 mg/mL glucose, 5 mg/mL NADP and 5 units glucose dehydrogenase to regenerate NADPH required for this reduction. Reactions were carried out at 28° C. for 24 hours. Product concentrations and enantiomeric excess of product was determined by HPLC.

*Candida sonorensis* SC16117 (ATCC #56511) produced the desired (R)-alcohol in 67% yield with 97% enantiomeric excess. Ketoreductase enzyme from *Candida sonorensis* SC16117 was purified to homogeneity from cell extracts. The purified protein reduced Part B ketone to corresponding Part C (R)-alcohol with 100% enantiomeric excess. Glucose, glucose dehydrogenase and NADP were used to regenerate cofactor NADPH required for reduction process.

Part D. (R)-2-(4-Amino-2-methoxyphenoxy)-1-cyclopropylethanol

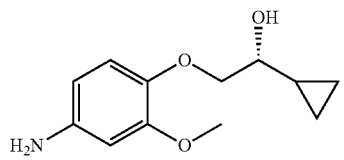

To a solution of (R)-1-cyclopropyl-2-(2-methoxy-4-nitrophenoxy)ethanol (20.90 g, 83 mmol), prepared in Part C, in EtOH (546 ml) was added 5% Pd/C, dry basis, Degussa type 50% water content (3.0 g, 0.705 mmol). The suspension was hydrogenated (1 atm. $H_2$, balloon) at 20° C. for 2.5 h; whereupon, LC/MS analysis revealed the reaction to be complete. After filtration of the reaction mixture through CELITE® pad and subsequent washing of the cake with EtOH, the filtrate was concentrated under vacuum using a rotary evaporator to yield (R)-2-(4-amino-2-methoxyphenoxy)-1-cyclopropylethanol as a brown solid. M.P. 71° C. (18.34 g, 100%). $^1$H NMR (400 MHz, $CDCl_3$): δ 0.18-0.27 (m, 1H), 0.38-0.43 (m, 1H), 0.45-0.61 (m, 2H), 0.82-0.92 (m, 1H), 3.21 (ddd, J=8.8, 8.8, 2.6 Hz, 1H), 3.80 (s, 3H), 3.86 (dd, J=10.1, 8.8 Hz, 1H), 4.09 (dd, J=10.1, 2.6 Hz, 1H), 6.21 (dd, J=8.3, 2.7 Hz, 1H), 6.29 (d, J=2.7 Hz, 1H), 6.78 (d, J=8.3 Hz, 1H). $^{13}$C NMR (100 MHz, $CDCl_3$) δ 151.2, 142.1, 140.8, 118.7, 106.9, 100.5, 76.5, 74.4, 55.7, 12.9, 2.5, 1.6. HPLC: 6.28 min retention time, 98.5% API; ZORBAX® column SB C18 4.6×75 mm; flow rate 2.5 ml/min; Gradient solvent system: from 100% A:0% B to 0% A:100% B for 8 min (Solvent A: 10% MeOH 90% $H_2O$=0.2% $H_3PO_4$; Solvent B: 90% MeOH–10% $H_2O$+ 0.2% $H_3PO_4$) Detection at 220 nm. LC/MS: m/e 224.5 (M+H); 4 min gradient.

Aniline 2

1-((4-Amino-2-methoxyphenoxy)methyl)-3,3-difluorocyclobutanol

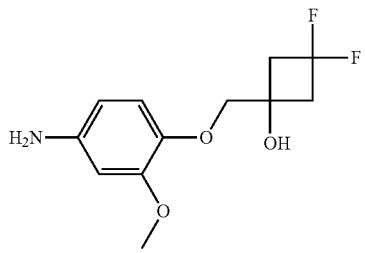

Part A.
3,3-Difluoro-N,N-dimethylcyclobutanecarboxamide

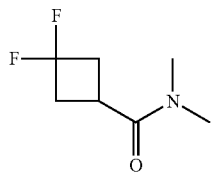

Oxalyl chloride (21.74 mL, 248 mmol) was added dropwise to a stirred solution of 3,3-difluorocyclobutanecarboxylic acid (26 g, 191 mmol; prepared as described in *Syn. Comm.*, 35:657 (2005) (Elend, D. et al.) in $CH_2Cl_2$ (500 mL) and DMF (0.5 mL) at 0° C. The reaction mixture was allowed to come to RT and stirred at RT for 1 h prior to being concentrated at RT using a rotary evaporator at ca. 50 mm Hg vacuum. After adding THF (300 mL) to the resulting residue, the stirred solution was cooled 0° C. prior to addition of a 2M solution of $Me_2NH$ (478 mL, 955 mmol) in THF. After stirring the reaction mixture at RT for 0.5 h, the mixture was partitioned between ether and 5% aq. $Na_2CO_3$. The organic layer was dried over $MgSO_4$ and concentrated in vacuo at RT. After portioning the residue between $CH_2Cl_2$ and water, the organic layer was dried over $MgSO_4$ and concentrated in vacuo at RT to give 3,3-difluoro-N,N-dimethylcyclobutanecarboxamide (24 g, 147 mmol, 77% yield) as a brown semi solid, used as such in the next step. $^1$H NMR (400 MHz, $CDCl_3$) δ 2.82-3.13 (9H, m), 2.62-2.79 (2H, m).

Part B.
1-(3,3-Difluorocyclobutyl)-N,N-dimethylmethanamine

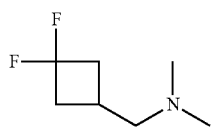

A solution of 3,3-difluoro-N,N-dimethylcyclobutanecarboxamide (24 g, 147 mmol) prepared in Part A in THF (500 mL) was added to a stirred suspension of lithium aluminum hydride (7.5 g, 198 mmol) in 500 mL THF at 0° C. The mixture was allowed to come to RT. After stirring the reaction mixture at RT for 18 h, it was quenched by slowly adding 10 mL 6 N NaOH and 5 mL water at 5° C. with stirring. The mixture was stirred at RT for 0.5 h, dried over $Na_2SO_4$ and filtered. The filtrate was concentrated to ca. 30 mL by a careful distillation of most of the THF using a Vigreux column. The remaining material was distilled under slightly reduced pressure (ca. 100-200 mm Hg); the fraction (20 mL, by 70-90° C.) contained the title compound contaminated with THF. The residual THF was carefully purged with a gentle stream of nitrogen to yield 1-(3,3-difluorocyclobutyl)-N,N-dimethylmethanamine (12 g, 80 mmol, 54.7% yield). $^1$H NMR (400 MHz, $CDCl_3$) δ 2.46-2.94 (2H, m), 2.38 (2H, d, J=6.55 Hz), 2.16-2.28 (9H, m).

Part C.
1-(3,3-Difluorocyclobutyl)-N,N-dimethylmethanamine oxide hydrate

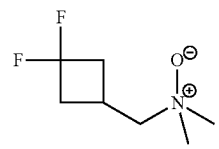

The tile compound was prepared as described in *Org. Syn. Coll.*, IV:612-615 (Cope, A. C. et al.) and *J. Am. Chem. Soc.*, 89(17):4534 (1967) (Doering et al.).

30% Aqueous $H_2O_2$ (18 mL) was added dropwise to a stirred solution of 1-(3,3-difluorocyclobutyl)-N,N-dimethylmethanamine (12 g, 80 mmol) prepared in Part B in methanol (100 mL) at 5 to 22° C. over 2 h. After stirring at RT for 20 h, additional 30% $H_2O_2$ (18 mL) was added. After 3 h, Pd black slurry (150 mg) in water (3 mL) was added to the stirred reaction mixture in small portions such that the temperature could be maintained between 5 to 25° C. with a cooling bath. The reaction mixture was stirred at RT for 1 h until the $O_2$ evolution ceased. After filtration, the filtrate was concentrated in vacuo to give 1-(3,3-difluorocyclobutyl)-N,N-dimethylmethanamine oxide hydrate as a thick colorless oil (15 g, semisolid). $^1$H NMR (400 MHz, $CD_3OD$) δ 3.47 (2H, d, J=5.29 Hz), 3.16 (6H, s), 2.75-2.92 (3H, m), 2.42-2.58 (2H, m).

Part D. 1,1-Difluoro-3-methylenecyclobutane

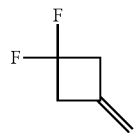

In order to remove most of the water from the sample, 1-(3,3-difluorocyclobutyl)-N,N-dimethylmethanamine oxide hydrate (15 g, 91 mmol) prepared in Part C was heated under vacuum (10 mm) at 100° C. using a distillation setup with the receiving flask cooled to −78° C. Once the water had been removed, the temperature was gradually increased to 165° C. After ca. 1 h most of the starting material had been pyrolized (a small amount of dark brown material remained in the distillation flask). Contents of the receiving flask were then washed sequentially with 5% aq. HCl (3×3 mL) and sat. $NaHCO_3$ (5 mL). The organic layer (olefin) was filtered through $Na_2SO_4$ giving 1,1-difluoro-3-methylenecyclobutane (5.5 g, 52.8 mmol, 58.2% yield) as a colorless oil. $^1$H NMR (400 MHz, CDCl$_3$) δ ppm 5.10 (2H, quin, J=2.52 Hz), 2.77-3.57 (4H, m).

Part E. 5,5-Difluoro-1-oxaspiro[2.3]hexane

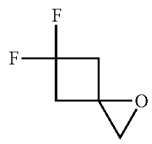

Meta chloroperbenzoic acid (74.6 g, 303 mmol) was added in small portions to a stirred solution of 1,1-difluoro-3-methylenecyclobutane (21.0 g, 202 mmol) prepared in Part D in CH$_2$Cl$_2$ (600 mL) at RT. The reaction mixture cooled with a water bath during the addition. After ca. 1 h the onset of a slight exotherm prompted further cooling using ice-water mixture. The reaction mixture was allowed to come to RT over 3 h. After stirring at RT for 16 h, additional m-CPBA (10 g) was added. The reaction mixture was stirred at RT for 24 h prior to being stored overnight in a refrigerator at 4° C. to precipitate out some of the acids. After filtration, the filtrate was washed with 10% Na$_2$CO$_3$. The organic layer was dried (Na$_2$SO$_4$), concentrated to ca. 170 mL using a Vigreux column. This material was flash distilled at ca. 10 mm to −78° C. traps (two traps in series were employed to minimize loss). The distillate was concentrated using a Vigreux column to a volume of approximately 50 mL affording a 3:1 mixture of CH$_2$Cl$_2$ and 5,5-difluoro-1-oxaspiro[2.3]hexane (80 g, 200 mmol, 99% yield) by NMR. This material was used without further purification in the next step. $^1$H NMR (400 MHz, CDCl$_3$ δ 2.91-3.16 (4H, m), 2.88 (2H, s).

Part F. 3,3-Difluoro-1-((2-methoxy-4-nitrophenoxy)methyl)cyclobutanol

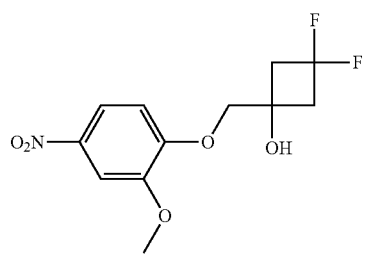 [SMILES: COc1cc([N+](=O)[O-])ccc1OCC1(O)CC(F)(F)C1]

A mixture of Part E compound (22.52 g, 0.06 mol), potassium 2-methoxy-4-nitrophenolate (12.43 g, 0.060 mol) prepared in Part E and NaH$_2$PO$_4$·H$_2$O (7.45 g, 0.054 mol) in 50 mL MeCN-water (85:15) was heated at 130° C. in a steel bomb for 3.5 h. The reaction mixture was diluted with EtOAc, washed with 5% Na$_2$CO$_3$, dried (MgSO$_4$) and concentrated. The crude product was recrystallized from ca. 150 mL MTBE giving 3,3-difluoro-1-((2-methoxy-4-nitrophenoxy)methyp-cyclobutanol (11.2 g, 0.039 mol, 64.5% yield) as a light yellow solid. An additional 1.2 g of a slightly less pure desired product was obtained upon concentration of the mother liquor to ca. 50 mL. $^1$H NMR (400 MHz, CDCl$_3$) δ 7.89 (1H, dd, J=8.94, 2.64 Hz), 7.76 (1H, d, J=2.77 Hz), 6.95 (1H, d, J=9.06 Hz), 4.16 (2H, s), 3.94 (3H, s), 3.36 (1H, s), 2.73-2.92 (4H, m).

Part G. 1-((4(4-Amino-2-methoxyphenoxy)methyl)-3,3-difluorocyclobutanol

A mixture of 3,3-difluoro-1-((2-methoxy-4-nitrophenoxy)methyl)cyclobutanol (32.0 g, 111 mmol) prepared in Part F and 10% Pd/C (2.0 g, 1.879 mmol) in 700 mL MeOH was stirred under H$_2$ at 50 psi for 1.5 h. After filtration, the filtrate was concentrated to give 1-((4-amino-2-methoxyphenoxy)methyl)-3,3-difluorocyclobutanol (28.9 g, 111 mmol, quantitative yield) as a light purple solid. $^1$H NMR (400 MHz, CD$_3$OD) δ 6.68 (1H, d, J=8.56 Hz), 6.35 (1H, d, J=2.52 Hz), 6.16 (1H, dd, J=8.31, 2.52 Hz), 4.77 (3H, br. s.), 3.78 (2H, s), 3.68 (3H, s), 2.68-2.82 (2H, m), 2.38-2.56 (2H, m).

| Ex. No. | Structure | HPLC retention (min) | LCMS (ES): m/z [M + H]+ | 1H-HMR | Synthetic Comments |
|---|---|---|---|---|---|
| 2 | 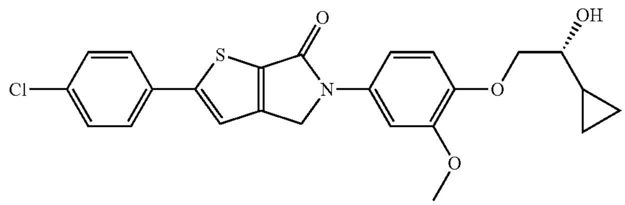 | 3.866 | 456 | 1H NMR (400 MHz, CD2Cl2) δ 7.54 (3 H, dd, J = 5.7, 3.1 Hz), 7.35 (2 H, d, J = 8.8 Hz), 7.25 (1 H, s), 6.93-7.02 (1 H, m), 6.85-6.92 (1 H, m), 4.70 (2 H, s), 4.08 (1 H, dd, J = 9.9, 2.9 Hz), 3.84-3.91 (1 H, m), 3.81 (3 H, s), 3.20 (1 H, td, J = 8.4, 2.6 Hz), 1.18 (1 H, s), 0.77-0.94 (1 H, m), 0.39-0.54 (2 H, m), 0.28-0.38 (1 H, m), 0.15-0.26 (1 H, m). | |
| 3 | 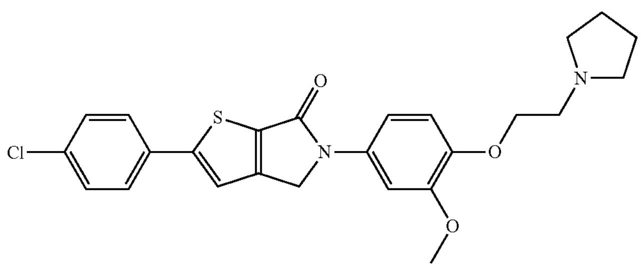 [SMILES: COc1cc(N2Cc3cc(-c4ccc(Cl)cc4)sc3C2=O)ccc1OCCN1CCCC1] | 2.940 | 469 | 1H NMR (400 MHz, CDCl3) δ 7.62 (1 H, s), 7.50 (2 H, d, J = 8.4 Hz), 7.33 (2 H, d, J = 8.4 Hz), 7.19 (1 H, s), 6.86 (2 H, s), 4.69 (2 H, s), 4.10 (2 H, t, J = 6.6 Hz), 3.84 (3 H, s), 2.88 (2 H, t, J = 6.4 Hz), 2.57 (4 H, br, s), 1.66-1.83 (4 H, m) | |
| 4 | 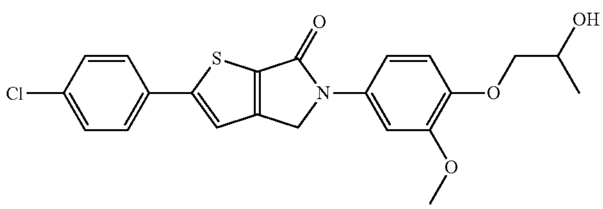 [SMILES: COc1cc(N2Cc3cc(-c4ccc(Cl)cc4)sc3C2=O)ccc1OCC(C)O] | 3.080 | 430 | 1H NMR (500 MHz, CD2Cl2) δ 7.52-7.56 (3 H, m), 7.35 (2 H, d, J = 8.8 Hz), 7.24 (1 H, s), 6.96 (1 H, dd, J = 8.8, 2.2 Hz), 6.87 (1 H, d, J = 8.8 Hz), 4.69 (2 H, s), 3.99-4.09 (1 H, m), 3.91 (1 H, dd, J = 9.6, 3.0 Hz), 3.81 (3 H, s), 3.65-3.72 (1 H, m), 2.64 (1 H, br. s.), 1.13 (3 H, d, J = 6.6 Hz). | |
| 5 | 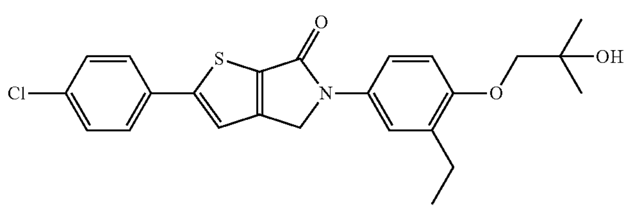 [SMILES: CCc1cc(N2Cc3cc(-c4ccc(Cl)cc4)sc3C2=O)ccc1OCC(C)(C)O] | 3.601 | 442 | 1H NMR (500 MHz, CD2Cl2) δ 7.53 (2 H, d, J = 8.3 Hz), 7.39-7.43 (2 H, m), 7.34 (2 H, d, J = 8.8 Hz), 7.24 (1 H, s), 6.79 (1 H, d, J = 9.4 Hz), 4.68 (2 H, s), 3.73 (2 H, s), 2.64 (2 H, q, J = 7.7 Hz), 1.27 (6 H, s), 1.16 (3 H, t, J = 7.7 Hz). | |
| 6 | 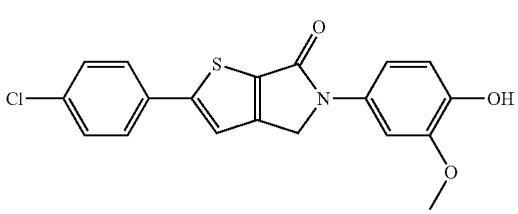 [SMILES: COc1cc(N2Cc3cc(-c4ccc(Cl)cc4)sc3C2=O)ccc1O] | 3.601 | 3.72 | 1H NMR (400 MHz, DMSO-d6) δ 8.97 (1 H, s), 7.82 (2 H, d, J = 8.4 Hz), 7.75 (1 H, s), 7.55 (2 H, d, J = 8.4 Hz), 7.46 (1 H, d, J = 2.2 Hz), 7.10 (1 H, dd, J = 8.6, 2.4 Hz), 6.80 (1 H, d, J = 8.4 Hz), 4.95 (2 H, s), 3.80 (3 H, s). | NH2Ar was commercially available. |

| Ex. No. | Structure | HPLC retention (min) | LCMS (ES): m/z [M + H]⁺ | ¹H-HMR | Synthetic Comments |
|---|---|---|---|---|---|
| 7 | 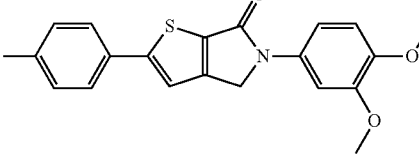 | 3.890 | 492 | ¹H NMR (400 MHz, DMSO-d₆) δ 7.83 (2 H, d, J = 8.4 Hz), 7.77 (1 H, s), 7.52-7.61 (3 H, m), 7.24 (1 H, dd, J = 8.8, 2.6 Hz), 7.07 (1 H, d, J = 8.8 Hz), 5.81 (1 H, s), 5.01 (2 H, s), 3.93 (2 H, s), 3.81 (3 H, s), 2.79-2.97 (2 H, m), 2.52-2.71 (2 H, m). | |
| 8 | 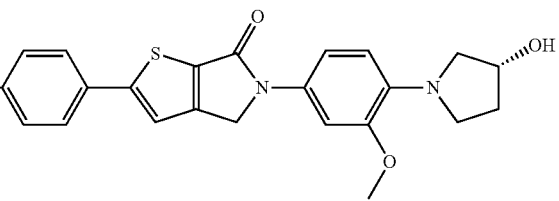 | 2.998 | 441 | ¹H NMR (500 MHz, CDCl₃) δ 8.37 (d, J = 2.2 Hz, 1 H), 7.76 (d, J = 8.8 Hz, 1 H), 7.58 (d, J = 8.8 Hz, 2 H), 7.42 (d, J = 8.2 Hz, 2 H), 7.30 (s, 1 H), 6.85 (dd, J = 8.8, 2.2 Hz, 1 H), 4.81 (s, 2 H), 4.74 (br. s., 1 H), 4.11 (d, J = 10.4 Hz, 1 H), 4.02 (s, 3 H), 3.85-3.92 (m, 1 H), 3.78-3.85 (m, 1 H), 3.62-3.72 (m, 1 H), 2.81 (d, J = 4.9 Hz, 1 H), 2.59 (ddd, J = 9.1, 4.9, 4.7 Hz, 1 H), 2.25-2.37 (m, 1 H). | NH₂Ar prepared as described in PCT Publication No. WO 2005/042541. |
| 9 | 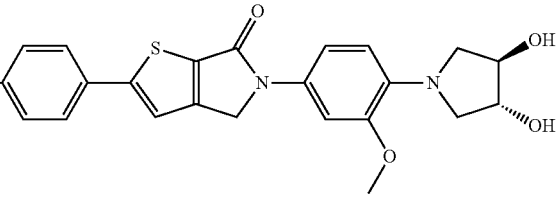 | 3.103 | 457 | ¹H NMR (500 MHz, DMSO-d₆) δ 7.81 (d, J = 8.2 Hz, 2 H), 7.75 (s, 1 H), 7.55 (d, J = 8.8 Hz, 2 H), 7.45 (s, 1 H), 7.17 (d, J = 7.1 Hz, 1 H), 6.69 (d, J = 8.2 Hz, 1 H), 4.96 (s, 2 H), 3.98 (br. s., 3 H), 3.79 (s, 3 H), 3.62 (dd, J = 9.9, 3.8 Hz, 2 H), 3.11 (d, J = 9.9 Hz, 2 H). | NH₂Ar prepared in a similar manner to that described in Ex. 9. |
| 10 | 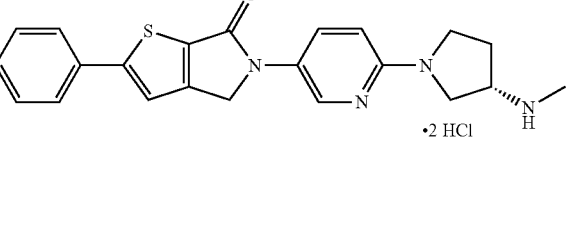 | 2.308 | 425 | ¹H NMR (500 MHz, CD₃OD) δ 8.55 (1 H, s), 8.33 (1 H, d, J = 8.3 Hz), 7.64 (2 H, d, J = 8.3 Hz), 7.49 (1 H, s), 7.38 (2 H, d, J = 8.3 Hz), 7.14 (1 H, d, J = 9.4 Hz), 4.88 (2 H, s), 3.92-4.12 (2 H, m), 3.80 (2 H, d, J = 9.4 Hz), 3.69 (1 H, br. s.), 2.75 (3 H, s), 2.49-2.65 (1 H, m), 2.35 (1 H, br. s). | NH₂Ar prepared and Boc deprotected as described in *Bioorg. Med. Chem. Lett.*, 15:3701 (2005). |

-continued

| Ex. No. | Structure | HPLC retention (min) | LCMS (ES): m/z [M + H]+ | 1H-HMR | Synthetic Comments |
|---|---|---|---|---|---|
| 11 | 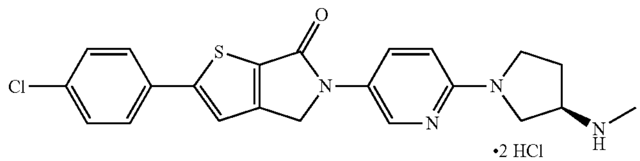 [SMILES: CN[C@@H]1CCN(c2ccc(N3Cc4cc(-c5ccc(Cl)cc5)sc4C3=O)cn2)C1] | 2.305 | 425 | 1H NMR (400 MHz, CD3OD) δ 8.56 (1 H, d, J = 2.2 Hz), 8.34 (1 H, dd, J = 9.7, 2.2 Hz), 7.64 (2 H, d, J = 8.8 Hz), 7.49 (1 H, s), 7.38 (2 H, d, J = 8.4 Hz), 7.16 (1 H, d, J = 9.7 Hz), 4.87 (2 H, s), 3.92-4.11 (2 H, m), 3.75-3.89 (2 H, m), 3.62-3.75 (1 H, m), 2.75 (3 H, s), 2.50-2.63 (1 H, m), 2.28-2.42 (1 H, m). | NH2Ar prepared and Boc deprotected as described in *Bioorg. Med. Chem. Lett.*, 15:3701 (2005). |
| 12 | 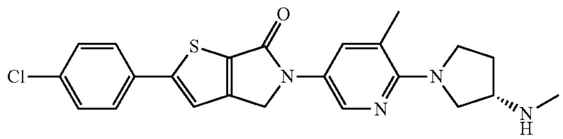 | 2.485 | 439 | 1H NMR (500 MHz, DMSO-d6) δ 8.43 (1 H, br. s.), 7.96 (1 H, br. s.), 7.75-7.85 (3 H, m), 7.56 (2 H, d, J = 8.3 Hz), 4.99 (2 H, s), 3.74 (4 H, br. s.), 3.53 (1 H, br. s.), 2.64 (3 H, br. s.), 2.35-2.44 (4 H, m), 2.24-2.33 (1 H, m), 2.15 (1 H, br. s). | NH2Ar prepared and Boc deprotected similarly as described in *Bioorg. Med. Chem. Lett.*, 15:3701 (2005). |
| 13 | 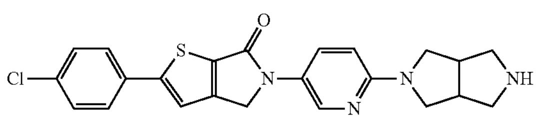 | 2.225 | 437 | 1H NMR (500 MHz, CD3OD) δ 8.48 (1 H, s), 8.18 (1 H, d, J = 8.8 Hz), 7.64 (2 H, d, J = 8.8 Hz), 7.48 (1 H, s), 7.38 (2 H, d, J = 8.8 Hz), 6.97 (1 H, d, J = 9.9 Hz), 4.84 (2 H, s), 3.73 (2 H, dd, J = 10.7, 6.9 Hz), 3.48-3.64 (4 H, m), 3.22-3.34 (4 H, m). | NH2Ar prepared similarly as described in *Bioorg. Med. Chem. Lett.*, 15:3701 (2005). |
| 14 | 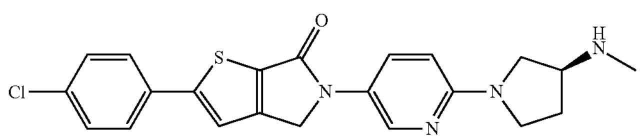 [SMILES: CN[C@H]1CCN(c2ccc(N3Cc4cc(-c5ccc(Cl)cc5)sc4C3=O)cn2)C1] | 2.778 | 426 | 1H NMR (500 MHz, D2O) δ 8.15 (br. s., 2 H), 7.19 (d, J = 8.2 Hz, 2 H), 7.14 (s, 1 H), 6.97 (d, J = 7.1 Hz, 2 H), 4.16 (br. s., 2 H), 3.98 (s, 1 H), 3.83 (br. s., 1 H), 3.61 (br. s., 1 H), 3.55 (br. s., 1 H), 3.49 (br. s., 1 H), 2.80 (s, 3 H), 2.55 (s, 1 H), 2.24 (br. s., 1 H). | NH2Ar prepared similarly as described in *Bioorg. Med. Chem. Lett.*, 15:3701 (2005). |
| 15 | 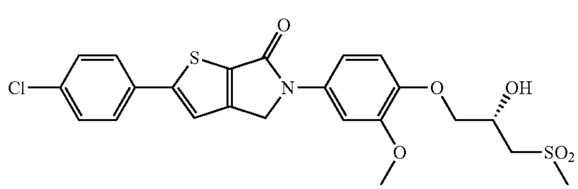 [SMILES: COc1cc(N2Cc3cc(-c4ccc(Cl)cc4)sc3C2=O)ccc1OC[C@H](O)CS(C)(=O)=O] | 3.560 | 508 | 1H NMR (500 MHz, DMSO-d6) δ 7.81 (2 H, d, J = 8.3 Hz), 7.76 (1 H, s), 7.54 (3 H, d, J = 6.6 Hz), 7.22 (1 H, d, J = 8.3 Hz), 7.03 (1 H, d, J = 8.8 Hz), 5.71 (1 H, d, J = 5.5 Hz), 4.99 (2 H, s), 4.28 (1 H, br. s.), 3.86-4.02 (2 H, m), 3.80 (3 H, s), 3.18-3.44 (2 H, m), 3.04 (3 H, s). | |

| Ex. No. | Structure | HPLC retention (min) | LCMS (ES): m/z [M + H]+ | 1H-HMR | Synthetic Comments |
|---|---|---|---|---|---|
| 16 | 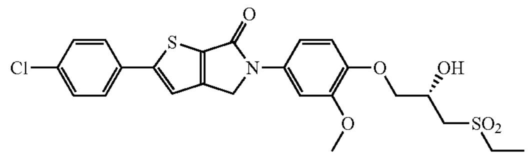 [SMILES: CCS(=O)(=O)C[C@@H](O)COc1ccc(N2Cc3cc(-c4ccc(Cl)cc4)sc3C2=O)cc1OC] | 3.601 | 522 | 1H NMR (400 MHz, DMSO-d6) δ 7.81 (2 H, d, J = 8.8 Hz), 7.76 (1 H, s), 7.55 (3 H, dd, J = 5.5, 2.9 Hz), 7.22 (1 H, dd, J = 8.8, 2.6 Hz), 7.03 (1 H, d, J = 8.8 Hz), 5.70 (1 H, d, J = 5.3 Hz), 4.99 (2 H, s), 4.27 (1 H, br. s.), 3.85-4.02 (2 H, m), 3.80 (3 H, s), 3.34-3.42 (1 H, m), 3.02-3.30 (3 H, m), 1.23 (3 H, t, J = 7.5 Hz). | |
| 17 | 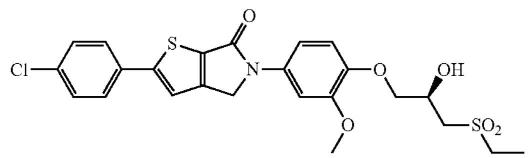 [SMILES: CCS(=O)(=O)C[C@H](O)COc1ccc(N2Cc3cc(-c4ccc(Cl)cc4)sc3C2=O)cc1OC] | 3.626 | 522 | 1H NMR (500 MHz, DMSO-d6) δ 7.82 (2 H, d, J = 8.3 Hz), 7.76 (1 H, s), 7.52-7.59 (3 H, m), 7.23 (1 H, dd, J = 8.8, 2.8 Hz), 7.04 (1 H, d, J = 8.8 Hz), 5.69 (1 H, d, J = 5.5 Hz), 5.00 (2 H, s), 4.24-4.33 (1 H, m), 3.88-4.02 (2 H, m), 3.81 (3 H, s), 3.37 (1 H, dd, J = 14.9, 9.35 Hz), 3.10-3.26 (3 H, m), 1.24 (3 H, t, J = 7.42 Hz). | |
| 18 | 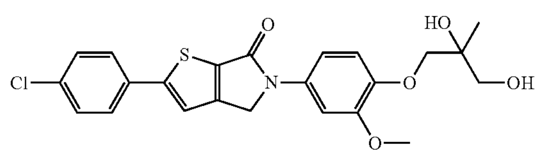 [SMILES: COc1cc(N2Cc3cc(-c4ccc(Cl)cc4)sc3C2=O)ccc1OCC(C)(O)CO] | 3.645 | 460 | 1H NMR (500 MHz, DMSO-d6) δ 7.80 (d, J = 8.53 Hz, 2 H), 7.74 (s, 1 H), 7.54 (d, J = 8.53 Hz, 2 H), 7.52 (d, J = 2.20 Hz, 1 H), 7.20 (dd, J = 8.80, 2.20 Hz, 1 H), 6.99 (d, J = 8.80 Hz, 1 H), 4.97 (s, 2 H), 4.62 (t, J = 5.77 Hz, 1 H), 4.49 (s, 1 H), 3.81 (d, J = 9.35 Hz, 1 H), 3.79 (s, 3 H), 3.71 (d, J = 9.35 Hz, 1 H), 3.35-3.42 (m, 1 H), 3.29-3.35 (m, 1 H), 1.13 (s, 3 H). | |

Example 19

2-(4-Chlorophenyl)-5-(4-(2-hydroxy-2-methylpropoxy)-3-methylphenyl)-4H-thieno[3,2-c]pyrrol-6(5H)-one

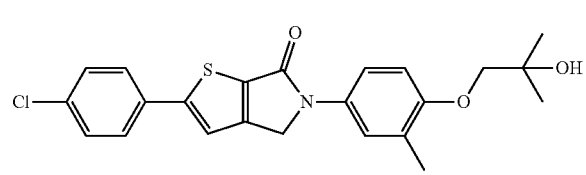 [SMILES: Cc1cc(N2Cc3cc(-c4ccc(Cl)cc4)sc3C2=O)ccc1OCC(C)(C)O]

Part A. 2-(4-Chlorophenyl)-5-(4-hydroxy-3-methylphenyl)-4H-thieno[3,2-c]pyrrol-6(5H)-one

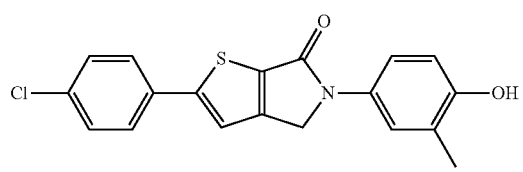 [SMILES: Cc1cc(N2Cc3cc(-c4ccc(Cl)cc4)sc3C2=O)ccc1O]

Using the procedure described in Part E and Part F of Example 1, 175 mg of Part D compound in Example 1, 68.2 mg of 4-amino-2-methylphenol and 121 mg of EDC in 2.6 ml of DMF followed by 73 mg of K2CO3 in 18 ml of DMF afforded 62.5 mg of the title compound as a yellow solid: ¹H NMR (500 MHz, CD₂Cl₂) δ 7.58 (2H, d, J=8.25 Hz), 7.38-7.43 (3H, m), 7.35 (1H, dd, J=8.52, 2.47 Hz), 7.29 (1H, s), 6.77 (1H, d, J=8.25 Hz), 4.71 (2H, s), 2.24 (3H, s); HPLC retention time: 3.740 min; LCMS (ES): m/z 356 [M+H]⁺.

Part B. 2-(4-Chlorophenyl)-5-(4-(2-hydroxy-2-methylpropoxy)-3-methylphenyl)-4H-thieno[3,2-c]pyrrol-6(5H)-one

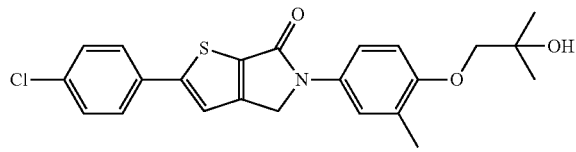 [SMILES: Cc1cc(N2Cc3cc(-c4ccc(Cl)cc4)sc3C2=O)ccc1OCC(C)(C)O]

A mixture of Part A compound (14.0 mg, 0.039 mmol), 2,2-dimethyloxirane (34.9 μL, 0.393 mmol) and K₂CO₃ (10.88 mg, 0.079 mmol) in MeCN (546 μL) and water (546 μL) was heated at 120° C. for 20 min. in a microwave reactor. Upon cooling, the reaction mixture was diluted with water and the solid formed was filtered, washed well with water, air dried under vacuum and purified by Prep. HPLC. The desired fraction was concentrated and lyophilized to afford 7.1 mg of the title compound as a light yellow solid: ¹H NMR (500 MHz, CD₂Cl₂) δ 7.54 (2H, d, J=8.80 Hz), 7.41 (2H, d, J=5.50 Hz), 7.35 (2H, d, J=8.80 Hz), 7.24 (1H, s), 6.78 (1H, d, J=9.35 Hz), 4.67 (2H, s), 3.73 (2H, s), 2.23 (3H, s), 1.27 (6H, s); HPLC retention time: 4.008 min; LCMS (ES): m/z 428 [M+H]⁺.

Example 20

(S)-2-(4-Chlorophenyl)-5-(6-(3-(dimethylamino) pyrrolidin-1-yl)pyridin-3-yl)-4H-thieno[3,2-c]pyrrol-6(5H)-one

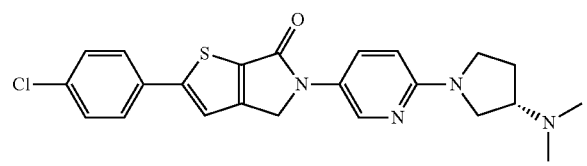 [SMILES: CN(C)[C@H]1CCN(c2ccc(N3Cc4cc(-c5ccc(Cl)cc5)sc4C3=O)cn2)C1]

Part A. (S)-2-(4-Chlorophenyl)-5-(6-(3-(dimethylamino)pyrrolidin-1-yl)pyridin-3-yl)-4H-thieno[3,2-c]pyrrol-6(5H)-one

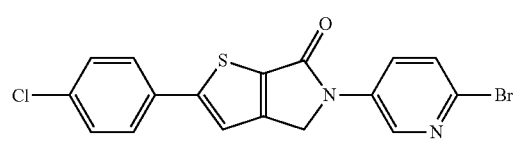 [SMILES: O=C1c2sc(-c3ccc(Cl)cc3)cc2CN1c1ccc(Br)nc1]

Using the procedure described in Part E and Part F of Example 1, 450 mg of Part D compound in Example 1, 185 mg of 6-bromopyridin-3-amine and 234 mg of EDC in 2.6 ml of DMF followed by 141 mg of K₂CO₃ in 3.0 ml of DMF afforded 83 mg of the title compound as a tan solid which was carried forward without further purification: HPLC retention time: 3.880 min; LCMS (ES): m/z 407 [M+H]⁺.

Part 8. (S)-2-(4-Chlorophenyl)-5-(6-(3-(dimethylamino)pyrrolidin-1-yl)pyridin-3-yl)-4H-thieno[3,2-c]pyrrol-6(5H)-one

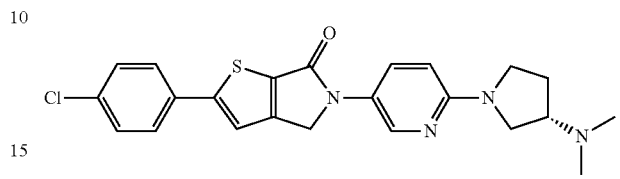

A mixture of Part A compound (10.00 mg, 0.016 mmol) and (S)—N,N-dimethylpyrrolidin-3-amine (64.0 mg, 0.561 mmol) in DMSO (214 μL) was allowed to stir at 150° C. in a microwave reactor for 60 min. Upon cooling to RT, the reaction mixture was diluted with water (5 mL). The solid formed was filtered, washed well with water and purified by Prep. HPLC. The desired fraction was concentrated, dissolved in CH₂Cl₂ (10 mL), washed with sat. NaHCO₃ (3×15 mL), water, brine, dried over anhydrous Na₂SO₄ and concentrated under vacuum to afford 4.6 mg of the title compound as a yellow solid: ¹H NMR (500 MHz, CD₂Cl₂) δ 8.18 (1H, d, J=2.75 Hz), 7.79 (1H, dd, J=8.80, 2.75 Hz), 7.53 (2H, d, J=8.25 Hz), 7.34 (2H, d, J=8.25 Hz), 7.24 (1H, s), 6.33 (1H, d, J=8.80 Hz), 4.62-4.67 (2H, m), 3.66 (1H, dd, J=9.35, 7.15 Hz), 3.55 (1H, t, J=8.80 Hz), 3.31 (1H, td, J=10.04, 6.87 Hz), 3.13 (1H, t, J=8.80 Hz), 2.66-2.79 (1H, m), 2.20 (6H, s), 2.07-2.17 (1H, m), 1.74-1.91 (1H, m); HPLC retention time: 2.317 min; LCMS (ES): m/z 439 [M+H]⁺.

Example 21

(R)-2-(4-Chlorophenyl)-5-(6-(3-(dimethylamino) pyrrolidin-1-yl)pyridin-3-yl)-4H-thieno[3,2-c]pyrrol-6(5H)-one

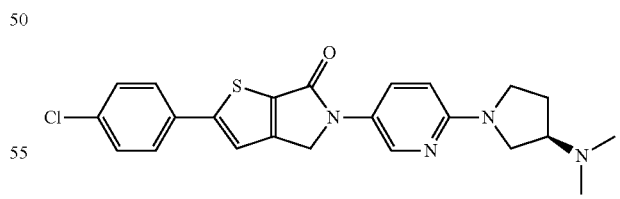

Using the procedure described in Part B of Example 20, 50 mg of Part A compound in Example 20 and 90 mg of (R)—N,N-dimethylpyrrolidin-3-amine in 1.6 ml of DMSO afforded 10.2 mg of the title compound as a yellow solid: ¹H NMR (500 MHz, CD₂Cl₂) δ 8.19 (1H, d, J=2.20 Hz), 7.79 (1H, dd, J=8.80, 2.75 Hz), 7.53 (2H, d, J=8.80 Hz), 7.34 (2H, d, J=8.80 Hz), 7.23 (1H, s), 6.33 (1H, d, J=8.80 Hz), 4.63 (2H, s), 3.66 (1H, dd, J=9.90, 7.15 Hz), 3.55 (1H, t, J=8.80 Hz), 3.31 (1H, td, J=10.04, 6.87 Hz), 3.14 (1H, t, J=9.07 Hz), 2.66-2.81 (1H, m), 2.21 (6H, s), 2.08-2.17 (1H, m), 1.75-1.92 (1H, m). HPLC retention time: 2.330 min; LCMS (ES): m/z 439 [M+H]⁺.

Example 22

2-(4-Chlorophenyl)-5-(4-((1,1-dioxido-4-hydroxytetrahydro-2H-thiopyran-4-yl)methoxy)-3-methoxyphenyl)-4H-thieno[2,3-c]pyrrol-6(5H)-one

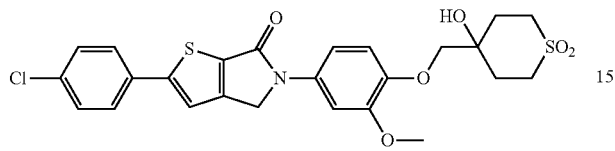

Part A. 4-((2-Methoxy-4-nitrophenoxy)methyl)tetrahydro-2H-thiopyran-4-ol

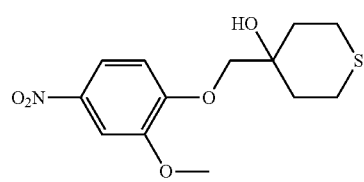 [SMILES: COc1cc([N+](=O)[O-])ccc1OCC1(O)CCSCC1]

A mixture of potassium 2-methoxy-4-nitrophenolate (3.02 g, 14.59 mmol), sodium phosphate monobasic, monohydrate (2.014 g, 14.59 mmol), acetonitrile (12 mL), water (3 mL) and 1-oxa-6-thiaspiro[2.5]octane (1.90 g, 14.59 mmol), prepared as described in patent WO 2005/063729 A1, was heated at 150° C. for 3.5 h in a microwave reactor. After cooling to RT, acetonitrile was mostly removed under vacuum, the remaining material was partitioned between EtOAc (100 mL) and H₂O (15 mL). The aqueous layer was extracted with EtOAc (2×15 mL) and the combined organic layers were dried (Na₂SO₄) and evaporated. The residue was purified by flash chromatography (silica gel, hexanes:EtOAc, 100:0 to 60:40) to afford 1.83 g (42%) of the title compound as a yellow solid: ¹H NMR (500 MHz, DMSO-d₆) δ 7.87 (dd, J=9.07, 2.47 Hz, 1H), 7.73 (d, J=2.75 Hz, 1H), 7.18 (d, J=9.35 Hz, 1H), 4.75 (s, 1H), 3.89 (s, 3H), 3.85 (s, 2H), 2.87-2.97 (m, 2H), 2.49 (s, 1H), 2.38 (d, J=13.20 Hz, 2H), 1.82-1.89 (m, 2H), 1.72-1.82 (m, 2H). HPLC retention time: 2.985 min; LCMS (ES): m/z 282 [M+H]⁺.

Part B. 1,1-Dioxido-4-((2-methoxy-4-nitrophenoxy)methyl)tetrahydro-2H-thiopyran-4-ol

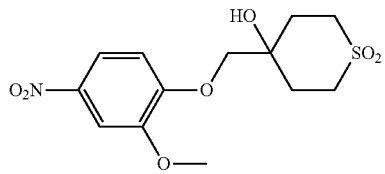

To a 0° C. solution of Part A compound (1.1 g, 3.67 mmol) in CH₂Cl₂ (30 mL) was added m-CPBA (2.059 g, 9.19 mmol) portionwise. The reaction mixture was allowed to warm to RT and stir for 30 min. The white solid formed was dissolved in DMF (10 mL) and stirred with Sat. NaHCO₃ (20 mL) for 30 min. The precipitate was filtered off, washed with water, and dried under vacuum to yield the title compound (1.1 g, 91% yield) as a white solid. ¹H NMR (500 MHz, DMSO-d₆) δ 7.88 (dd, J=8.94, 2.61 Hz, 1H), 7.74 (d, J=2.61 Hz, 1H), 7.19 (d, J=8.94 Hz, 1H), 5.27 (s, 1H), 4.00 (s, 2H), 3.88 (s, 3H), 3.16-3.28 (m, 2H), 2.97-3.07 (m, 2H), 2.08-2.18 (m, 2H), 2.01-2.08 (m, 2H). HPLC retention time: 2.138 min; LCMS (ES): m/z 332 [M+H]⁺.

Part C. 1,1-Dioxido-4-((2-methoxy-4-aminophenoxy)methyl)tetrahydro-2H-thiopyran-4-ol 1,1-dioxide

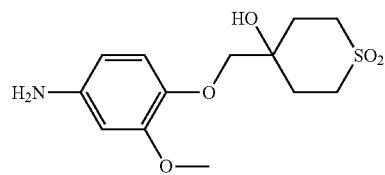 [SMILES: COc1cc([N+](=O)[O-])ccc1OCC1(O)CCS(=O)(=O)CC1]

To a solution of Part B compound (1.0 g, 3.02 mmol) in MeOH (30 mL) was added Palladium on Carbon (0.193 g, 0.091 mmol) and the reaction was allowed to stir under an H₂ (1 atm, balloon) (6.08 mg, 3.02 mmol) atmosphere at RT for 2.0 h. The reaction mixture was filtered through a pad a CELITE®, concentrated, and air dried under vacuum to give the title compound (0.90 g, 99% yield) as a tan solid: ¹H NMR (500 MHz, DMSO-d₆) δ 6.65 (d, J=8.39 Hz, 1H), 6.25 (d, J=2.61 Hz, 1H), 6.03 (dd, J=8.39, 2.61 Hz, 1H), 5.07 (s, 1H), 4.72 (s, 2H), 3.67 (s, 3H), 3.62 (s, 2H), 3.16-3.25 (m, 2H), 2.94-3.02 (m, 2H), 2.09-2.21 (m, 2H), 1.90-2.00 (m, 2H). HPLC retention time: 0.480 min; LCMS (ES): m/z 302 [M+H]⁺.

Part D. 3-(Chloromethyl)-5-(4-chlorophenyl)-N-(4-((1,1-dioxido-4-hydroxytetrahydro-2H-thiopyran-4-yl)methoxy)-3-methoxyphenyl)thiophene-2-carboxamide

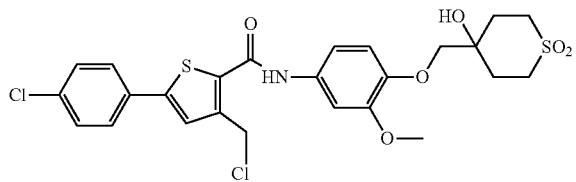 [SMILES: COc1cc(NC(=O)c2sc(-c3ccc(Cl)cc3)cc2CCl)ccc1OCC1(O)CCS(=O)(=O)CC1]

Using the procedure described in Part E of Example 1, Part D compound of Example 1 (230 mg, 0.694 mmol), Part C compound (209 mg, 0.694 mmol), and EDC (133 mg, 0.694 mmol) in DMF (7.0 mL) yielded the title compound (270 mg, 68% yield) as a yellow solid: HPLC retention time: 3.793 min; LCMS (ES): m/z 570 [M+H]+.

Part E. 2-(4-Chlorophenyl)-5-(4-((1,1-dioxido-4-hydroxytetrahydro-2H-thiopyran-4-yl)methoxy)-3-methoxyphenyl)-4H-thieno[2,3-c]pyrrol-6(5H)-one

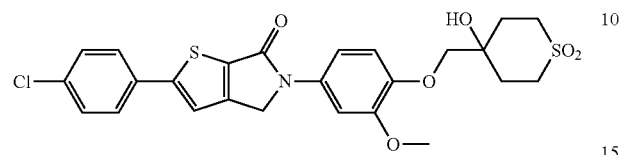

Using the procedure described in Part F of Example 1, Part D compound (270 mg, 0.473 mmol) and K$_2$CO$_3$ (65.4 mg, 0.473 mmol) in DMF (5.00 mL) gave the title compound (240 mg, 93% yield) as a yellow solid: $^1$H NMR (500 MHz, DMSO-d) δ 7.81 (d, J=8.25 Hz, 2H), 7.75 (s, 1H), 7.50-7.59 (m, 3H), 5.19 (s, 1H), 4.99 (br. s., 2H), 3.82 (br. s., 2H), 3.80 (s, 3H), 3.23 (t, J=12.92 Hz, 2H), 3.02 (d, J=12.65 Hz, 2H), 2.16 (t, J=13.75 Hz, 2H), 2.02 (d, J=14.30 Hz, 2H). HPLC retention time: 3.661 min; LCMS (ES): m/z 534 [M+H]+.

Example 23

2-(5-Chloropyridin-2-yl)-5-(4-(cis-3,4-dihydroxy-pyrrolidin-1-yl)-3-methoxyphenyl)-4H-thieno[2,3-c]pyrrol-6(5H)-one

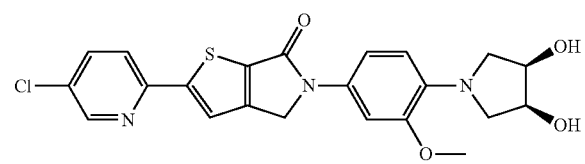 [SMILES: COc1cc(N2Cc3cc(-c4ccc(Cl)cn4)sc3C2=O)ccc1N1C[C@@H](O)[C@@H](O)C1]

Part A. 5-(5-Chloropyridin-2-yl)-3-methylthiophene-2-carbaldehyde

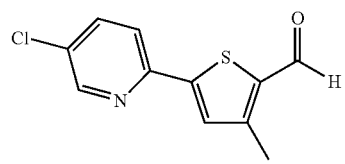

To a degassed solution of 5-formyl-4-methylthiophen-2-ylboronic acid (2.21 g, 13.0 mmol, commercially available), 2-bromo-5-chloropyridine (2.00 g, 10.4 mmol, commercially available) and 2 N Na$_2$CO$_3$ (10.4 mL, 20.8 mmol) in DMF (70.2 mL) was added PdCl$_2$dppf (0.380 g, 0.520 mmol); the flask degassed and heated to 80° C. for 2.0 h. Upon cooling, the reaction mixture was diluted with water (100 mL) and extracted with EtOAc (3×75 ml). The combined organic layers were washed with brine, dried over anhydrous Na$_2$SO$_4$, concentrated and purified by flash chromatography (silica gel, CH$_2$Cl$_2$:EtOAc, 100:0 to 0:100) to afford 2.01 g of the title compound as a yellow solid: $^1$H NMR (500 MHz, DMSO-d$_6$) δ 9.96 (1H, s), 8.57 (1H, s), 7.98 (2H, s), 7.75 (1H, s), 2.49 (3H, s).HPLC retention time: 3.158 min; LCMS (ES): m/z 238 [M+H]+.

Part B. 5-(5-Chloropyridin-2-yl)-3-methylthiophene-2-carboxylic acid

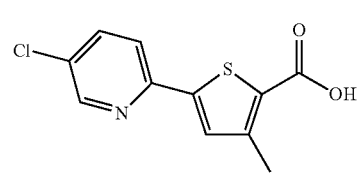 [SMILES: Cc1cc(-c2ccc(Cl)cn2)sc1C(=O)O]

Procedure A:

To a 0° C. mixture of Part A compound (1.74 g, 7.32 mmol), 2.5 N aqueous solution of sodium dihydrogen phosphate (3.02 mL, 7.54 mmol) and 30% H$_2$O$_2$(0.471 mL, 7.69 mmol) in MeCN (73.2 mL) was added a solution of sodium chlorite (1.12 g, 9.88 mmol) in 4.4 mL water dropwise over a period of 2 h. The mixture was slowly warm to RT. After stirring for 7H, sodium sulfite (0.100 mg, mmol) was added and the mixture was allowed to stir for 15 min at which point it was acidified to pH=2 with 1 N HCl. The solid formed was filtered, washed well with water and air dried under vacuum to afford 1.71 g of the title compound as a light yellow solid that was carried forward without further purification.

Procedure B:

To a mixture of Part A compound (14.0 g, 58.9 mmol) and a 2.5 N aqueous solution of sodium dihydrogen phosphate (24.3 ml, 60.7 mmol) in DMSO (475 mL) at RT was added a solution of sodium chlorite (9.0 g, 80.0 mmol) in 21 mL water dropwise over a period of 2 h. The reaction was allowed to stir at RT for 18 h at which point it was diluted with water (300 ml) and acidified to pH=2 with 1 N HCl. The solid formed was filtered, washed well with water and air dried under vacuum to yield 15.0 g (100% yield) of the title compound as an light yellow solid that was carried forward without further purification: $^1$H NMR (500 MHz, DMSO-d$_6$) δ 13.02 (1H, br. s.), 8.61 (1H, s), 8.00 (1H, s), 7.73 (1H, s), 2.47 (3H, s). HPLC retention time: 3.283 min; LCMS (ES): m/z 254 [M+H]+.

Part C. 3-(Bromomethyl)-5-(5-chloropyridin-2-yl)thiophene-2-carboxylic acid

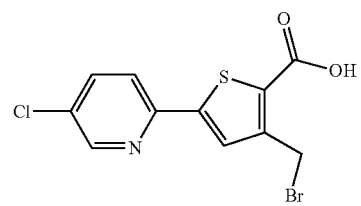 [SMILES: O=C(O)c1sc(-c2ccc(Cl)cn2)cc1CBr]

Using the procedure described in Part D of Example 1, 1.70 g of Part B compound, 0.854 mL of HMDS, 1.20 g of NBS and 110 mg of AIBN in 6.0 mL of CCl$_4$ afforded 1.78 g of the title compound as a tan solid which was carried forward without further purification: HPLC retention time: 3.486 min; LCMS (ES): m/z 334 [M+H]⁺.

Part D.
1-(2-Methoxy-4-nitrophenyl)-2,5-dihydro-1H-pyrrole

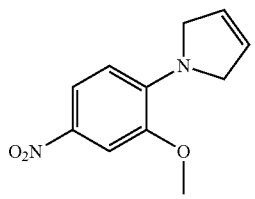 [SMILES: COc1cc([N+](=O)[O-])ccc1N1CC=CC1]

A mixture of 1-chloro-2-methoxy-4-nitrobenzene (2.71 g, 14.47 mmol) and 2,5-dihydro-1H-pyrrole (2.0 g, 28.9 mmol) was stirred at 100° C. under a stream of N₂ for 10 h. The reaction was cooled to RT to give a brown solid which was dissolved in CH₂Cl₂ (200 mL), washed with 100 mL of 1 N NaOH solution and brine, dried over MgSO₄, and concentrated. The resulting brown oil was purified by flash chromatography (silica gel, Hexanes:EtOAc, 100:0 to 80:20) to afford the title compound (2.67 g, 84% yield) as a orange solid: ¹H NMR (500 MHz, CDCl₃) δ 7.84 (dd, J=8.80, 2.50 Hz, 1H), 7.65 (d, J=2.50 Hz, 1H), 6.39 (d, J=8.80 Hz, 1H), 5.89 (s, 2H), 4.46 (s, 4H), 3.83 (s, 3H). HPLC retention time: 3.315 min; LCMS (ES): m/z 221 [M+H]⁺.

Part E. cis-1-(2-Methoxy-4-nitrophenyl)pyrrolidine-3,4-diol

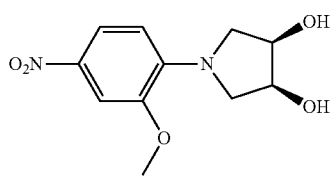 [SMILES: COc1cc([N+](=O)[O-])ccc1N1C[C@@H](O)[C@@H](O)C1]

Part D compound (500 mg, 2.270 mmol) was dissolved in acetone (20 mL) Water (1.4 mL) was added to the mixture followed by 4-methylmorpholine N-oxide (572 mg, 4.88 mmol). Osmium tetroxide (0.088 mL, 7.04 μmol) was then added to the mixture. Reaction stirred at RT for 16 hours and quenched with 1N sodium thiosulfate. Acetone was removed from the mixture under vacuum. The remaining aqueous mixture was extracted with ethyl acetate (3×20 mL). Organic layers were combined, washed successively with water and brine, dried over MgSO₄ and concentrated. The resulting brown oil was purified by flash chromatography (silica gel, CH₂Cl₂:MeOH, 100:0 to 95:5) to afford the title compound (500 mg, 1.967 mmol, 87% yield) as a orange solid: ¹H NMR (500 MHz, CDCl₃) δ 2.43 (br. s., 2H) 3.62 (dd, J=11.27, 4.12 Hz, 2H) 3.83 (dd, J=11.27, 4.12 Hz, 2H) 3.85 (s, 3H) 4.37 (hr. s., 2H) 6.46 (d, J=8.80 Hz, 1H) 7.65 (d, J=2.20 Hz, 1H) 7.83 (dd, J=8.80, 2.20 Hz, 1H). HPLC retention time: 0.187 min; LCMS (ES): m/z 255 [M+H]⁺.

Part F. cis-1-(4-Amino-2-methoxyphenyl)pyrrolidine-3,4-diol

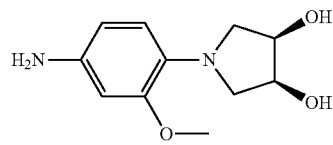 [SMILES: COc1cc(N)ccc1N1C[C@@H](O)[C@@H](O)C1]

Using the procedure described in Part C of Example 22, Part E compound (250 mg, 0.983 mmol) in MeOH (10 mL) afforded the title compound (200 mg, 91% yield) as a light brown oil that was carried forward without further purification: HPLC retention time: 0.168 min; LCMS (ES): m/z 225 [M+H]⁺.

Part G. 3-(Chloromethyl)-5-(5-chloropyridin-2-yl)-N-(4-(cis-3,4-dihydroxypyrrolidin-1-yl)-3-methoxyphenyl)thiophene-2-carboxamide

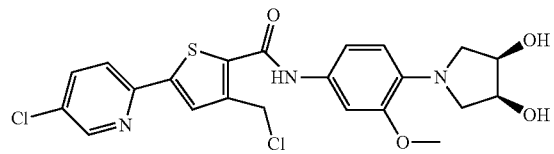 [SMILES: COc1cc(NC(=O)c2sc(-c3ccc(Cl)cn3)cc2CCl)ccc1N1C[C@@H](O)[C@@H](O)C1]

Using the procedure described in Part E of Example 1, Part C compound (100 mg, 0.301 mmol), Part F compound (67.4 mg, 0.301 mmol) and EDC (69.2 mg, 0.361 mmol) in DMF (3.0 mL) afforded the title compound (149 mg) as a light brown oil that was carried forward without further purification: HPLC retention time: 2.855 min; LCMS (ES): m/z 494 [M+H]⁺.

Part H. 2-(5-Chloropyridin-2-yl)-5-(4-(cis-3,4-dihydroxypyrrolidin-1-yl)-3-methoxyphenyl)-4H-thieno[2,3-c]pyrrol-6(5H)-one

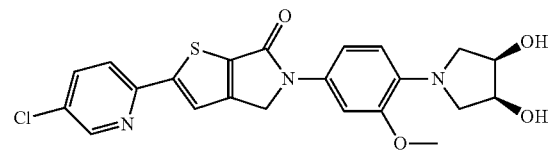 [SMILES: COc1cc(N2Cc3cc(-c4ccc(Cl)cn4)sc3C2=O)ccc1N1C[C@@H](O)[C@@H](O)C1]

Using the procedure described in Part F of Example 1, Part G compound (149 mg, 0.301 mmol) and K₂CO₃ (42 mg, 0.304 mmol) in DMF (3.0 mL) afforded the title compound (40 mg, 29.0% yield) as a dark red solid: ¹H NMR (500 MHz, DMSO-d₆) δ 8.66 (d, J=2.75 Hz, 1H) 8.12-8.18 (m, 1H) 8.05-8.10 (m, 1H) 8.02 (s, 1H) 7.42 (d, J=2.75 Hz, 1H) 7.15 (dd, J=8.52, 2.47 Hz, 1H) 6.60 (d, J=8.80 Hz, 1H) 4.96 (s, 2H) 4.76 (d, J=4.40 Hz, 2H) 4.02-4.11 (m, 2H) 3.77 (s, 3H) 3.49 (dd, J=9.62, 5.22 Hz, 2H) 3.14 (dd, 2H). HPLC retention time: 2.720 min; LCMS (ES): m/z 458 [M+H]⁺.

Examples 24 to 39

These examples were prepared following a similar method to that described in Example 23 using the appropriate 5-substituted 3-(bromomethyl)-thiophene-2-carboxylic acid and aniline. The aniline in Example 28 was prepared as described in U.S. Publication No. US 2007/0093509 A1.

| Ex. No. | Structure | HPLC retention (min) | LCMS (ES): m/z [M + H]$^+$ | $^1$H-NMR |
|---|---|---|---|---|
| 24 | 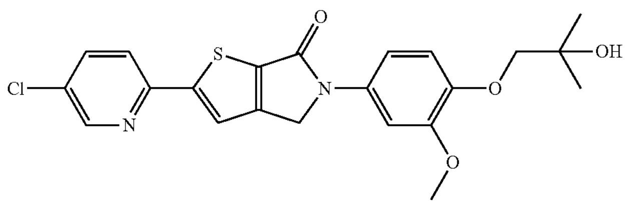 | 3.588 | 445 | $^1$H NMR (500 MHz, DMSO) δ 8.61 (1 H, d, J = 2.75 Hz), 8.10 (1 H, d, J = 8.80 Hz), 8.02 (1 H, dd, J = 8.52, 2.47 Hz), 7.98 (1 H, s), 7.48 (1 H, d, J = 2.20 Hz), 7.17 (1 H, dd, J = 8.52, 2.47 Hz), 6.95 (1 H, d, J = 8.80 Hz), 4.95 (2 H, s), 4.52 (1 H, s), 3.75 (3 H, s), 3.65 (2 H, s), 1.16 (6 H, s). |
| 25 | 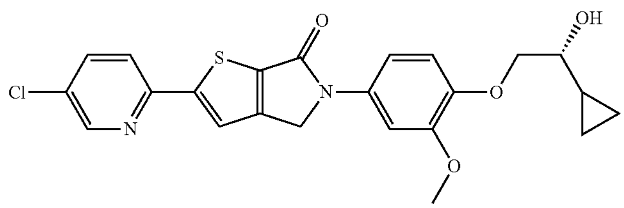 [SMILES: COc1cc(N2Cc3cc(-c4ccc(Cl)cn4)sc3C2=O)ccc1OC[C@H](O)C1CC1] | 3.631 | 457 | $^1$H NMR (500 MHz, CD$_2$Cl$_2$) δ 8.49 (1 H, d, J = 2.20 Hz), 7.67-7.75 (1 H, m), 7.60-7.66 (1 H, m), 7.58 (1 H, s), 7.54 (1 H, d, J = 2.20 Hz), 6.97 (1 H, dd, J = 8.52, 2.47 Hz), 6.85-6.93 (1 H, m), 4.71 (2 H, s), 4.08 (1 H, dd, J = 9.90, 2.75 Hz), 3.87 (1 H, t, J = 8.80 Hz), 3.81 (3 H, s), 3.20 (1 H, td, J = 8.11, 2.47 Hz), 0.76-0.94 (1 H, m), 0.38-0.56 (2 H, m), 0.27-0.37 (1 H, m), 0.16-0.28 (1 H, m). |
| 26 | 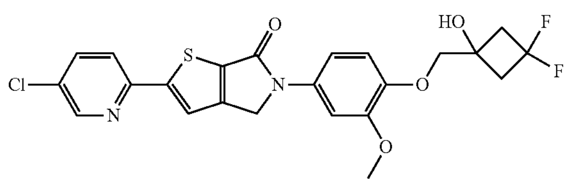 [SMILES: COc1cc(N2Cc3cc(-c4ccc(Cl)cn4)sc3C2=O)ccc1OCC1(O)CC(F)(F)C1] | 3.691 | 493 | $^1$H NMR (400 MHz, CDCl$_3$) δ 8.51 (1 H, d, J = 1.76 Hz), 7.76 (1 H, d, J = 2.20 Hz), 7.69 (1 H, dd, J = 8.57, 2.42 Hz), 7.49-7.64 (2 H, m), 6.76-7.04 (2 H, m), 4.72 (2 H, s), 4.01 (2 H, s), 3.85 (3 H, s), 2.62-2.85 (4 H, m). |
| 27 | 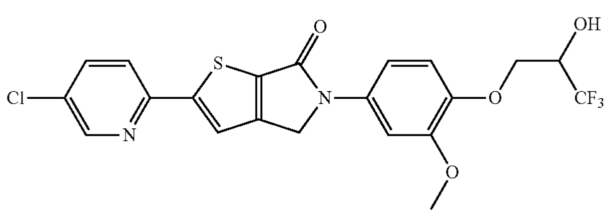 [SMILES: COc1cc(N2Cc3cc(-c4ccc(Cl)cn4)sc3C2=O)ccc1OCC(O)C(F)(F)F] | 3.660 | 485 | $^1$H NMR (500 MHz, DMSO) δ 8.65 (1 H, d, J = 2.20 Hz), 8.15 (1 H, d, J = 8.25 Hz), 8.02-8.10 (1 H, m), 7.99-8.04 (1 H, m), 7.56 (1 H, d, J = 2.20 Hz), 7.23 (1 H, dd, J = 8.80, 2.20 Hz), 7.07 (1 H, d, J = 8.80 Hz), 6.65 (1 H, d, J = 6.05 Hz), 5.00 (2 H, s), 4.37 (1 H, br. s.), 4.16 (1 H, dd, J = 10.45, 3.85 Hz), 4.04 (1 H, dd, J = 10.45, 7.15 Hz), 3.78-3.82 (3 H, m). |
| 28 | 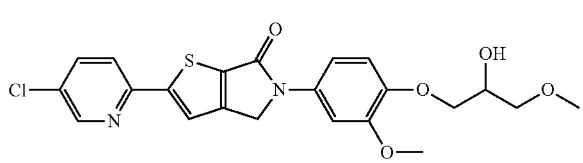 [SMILES: COCC(O)COc1ccc(N2Cc3cc(-c4ccc(Cl)cn4)sc3C2=O)cc1OC] | 3.425 | 461 | $^1$H NMR (500 MHz, CDCl$_3$) δ 8.53 (d, J = 2.75 Hz, 1 H) 7.73 (d, J = 2.75 Hz, 1 H) 7.69 (dd, J = 8.25, 2.20 Hz, 1 H) 7.61 (d, J = 8.25 Hz, 1 H) 7.51 (s, 1 H) 4.75 (s, 2 H) 4.16 (br. s., 1 H) 4.06-4.10 (m, 1 H) 3.99-4.05 (m, 1 H) 3.89 (s, 3 H) 3.50-3.59 (m, 2 H) 3.40 (s, 3 H). |
| 29 | 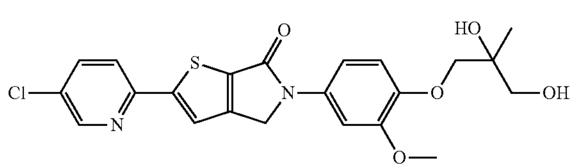 [SMILES: COc1cc(N2Cc3cc(-c4ccc(Cl)cn4)sc3C2=O)ccc1OCC(C)(O)CO] | 3.333 | 461 | $^1$H NMR (500 MHz, DMSO-d$_6$) δ 9.00 (s, 2 H), 8.05 (s, 1 H), 7.52 (d, J = 2.20 Hz, 1 H), 7.24 (dd, J = 8.80, 2.20 Hz, 1 H), 7.04 (d, J = 8.80 Hz, 1 H), 5.68 (d, J = 6.05 Hz, 1 H), 5.01 (s, 2 H), 4.22-4.32 (m, 1 H), 3.87-4.02 (m, 2 H), 3.80 (s, 3 H), 3.36 (dd, J = 14.85, 8.80 Hz, 1 H), 3.17-3.25 (m, 2 H), 3.08-3.17 (m, 1 H), 1.23 (t, J = 7.42 Hz, 3 H). |

| Ex. No. | Structure | HPLC retention (min) | LCMS (ES): m/z [M + H]+ | 1H-NMR |
|---|---|---|---|---|
| 30 | 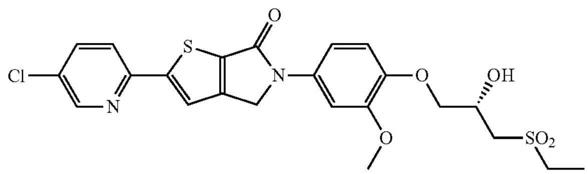 [SMILES: CCS(=O)(=O)C[C@@H](O)COc1ccc(N2Cc3cc(-c4ccc(Cl)cn4)sc3C2=O)cc1OC] | 3.293 | 523 | 1H NMR (400 MHz, DMSO) δ 8.66 (1 H, d, J = 2.20 Hz), 8.11-8.20 (1 H, m), 8.04-8.11 (1 H, m), 8.04 (1 H, s), 7.55 (1 H, d, J = 2.64 Hz), 7.23 (1 H, dd, J = 8.79, 2.64 Hz), 7.03 (1 H, d, J = 8.79 Hz), 5.70 (1 H, d, J = 5.71 Hz), 5.00 (2 H, s), 4.17-4.34 (1 H, m), 3.87-4.03 (2 H, m), 3.80 (3 H, s), 3.34-3.41 (1 H, m), 3.02-3.28 (3 H, m), 1.23 (3 H, t, J = 7.47 Hz). |
| 31 | 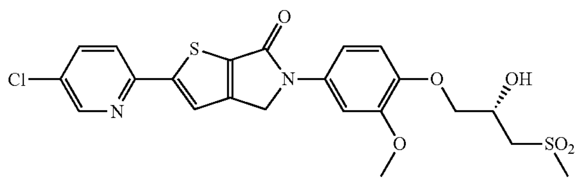 | 3.250 | 509 | 1H NMR (400 MHz, DMSO-d6) δ 8.65 (1 H, d, J = 2.20 Hz), 8.10-8.19 (1 H, m), 8.02-8.10 (1 H, m), 8.02 (1 H, s), 7.54 (1 H, d, J = 2.20 Hz), 7.23 (1 H, dd, J = 8.79, 2.20 Hz), 7.03 (1 H, d, J = 8.79 Hz), 5.70 (1 H, d, J = 5.50 Hz), 5.00 (2 H, s), 4.21-4.37 (1 H, m), 3.84-4.05 (2 H, m), 3.80 (3 H, s), 3.17-3.53 (2 H, m), 3.04 (3 H, s). |
| 32 | 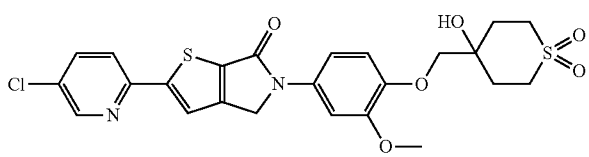 [SMILES: COc1cc(N2Cc3cc(-c4ccc(Cl)cn4)sc3C2=O)ccc1OCC1(O)CCS(=O)(=O)CC1] | 3.331 | 535 | 1H NMR (500 MHz, DMSO-d6) δ 8.65 (d, J = 2.20 Hz, 1 H), 8.14 (d, J = 8.80 Hz, 1 H), 8.06 (dd, J = 8.80, 2.20 Hz, 1 H), 8.02 (s, 1 H), 7.53 (d, J = 2.20 Hz, 1 H), 7.23 (dd, J = 8.80, 2.20 Hz, 1 H), 7.02 (d, J = 8.80 Hz, 1 H), 5.20 (s, 1 H), 4.99 (s, 3 H), 3.82 (s, 2 H), 3.80 (s, 3 H), 3.18-3.28 (m, 2 H), 2.98-3.06 (m, 2 H), 2.11-2.21 (m, 2 H), 1.97-2.05 (m, 2 H). |
| 33 | 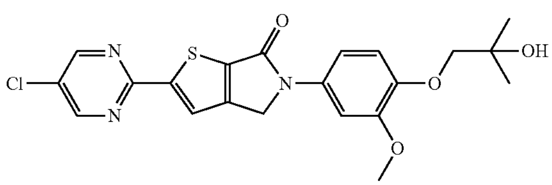 [SMILES: COc1cc(N2Cc3cc(-c4ncc(Cl)cn4)sc3C2=O)ccc1OCC(C)(C)O] | 3.588 | 446 | 1H NMR (500 MHz, DMSO-d6) δ 9.00 (2 H, s), 8.06 (1 H, s), 7.50 (1 H, d, J = 2.20 Hz), 7.22 (1 H, dd, J = 8.80, 2.75 Hz), 7.00 (1 H, d, J = 8.80 Hz), 5.00 (2 H, s), 4.57 (1 H, br. s.), 3.80 (3 H, s), 3.69 (2 H, s), 1.20 (6 H, s). |
| 34 | 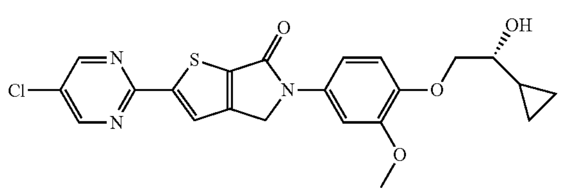 [SMILES: COc1cc(N2Cc3cc(-c4ncc(Cl)cn4)sc3C2=O)ccc1OC[C@H](O)C1CC1] | 3.621 | 458 | 1H NMR (500 MHz, DMSO-d6) δ 9.08 (2 H, s), 8.14 (1 H, s), 7.57 (1 H, d, J = 2.20 Hz), 7.30 (1 H, dd, J = 8.52, 2.47 Hz), 7.10 (1 H, d, J = 8.80 Hz), 5.08 (2 H, s), 4.89 (1 H, d, J = 4.95 Hz), 3.94-4.11 (2 H, m), 3.87 (3 H, s), 0.91-1.14 (1 H, m), 0.41-0.51 (2 H, m), 0.24-0.43 (2 H, m). |
| 35 | 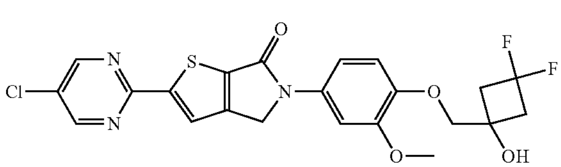 [SMILES: COc1cc(N2Cc3cc(-c4ncc(Cl)cn4)sc3C2=O)ccc1OCC1(O)CC(F)(F)C1] | 3.658 | 494 | 1H NMR (500 MHz, CDCl3) δ 8.69 (s, 2 H) 7.95 (s, 1 H) 7.82 (s, 1 H) 6.89-7.05 (m, 2 H) 4.81 (s, 2 H) 4.08 (s, 2 H) 3.92 (s, 3 H) 3.69 (s, 1 H) 2.65-2.88 (m, 4 H). |
| 36 | 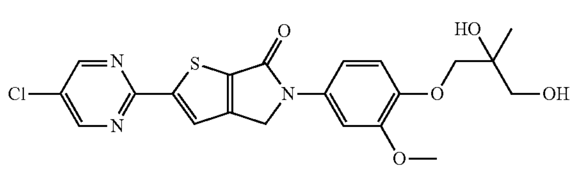 [SMILES: COc1cc(N2Cc3cc(-c4ncc(Cl)cn4)sc3C2=O)ccc1OCC(C)(O)CO] | 3.298 | 462 | 1H NMR (500 MHz, DMSO-d6) δ 8.98 (s, 2 H), 8.03 (s, 1 H), 7.49 (d, J = 2.20 Hz, 1 H), 7.21 (dd, J = 8.80, 2.20 Hz, 1 H), 6.99 (d, J = 8.80 Hz, 1 H), 4.98 (s, 2 H), 4.62 (t, J = 5.77 Hz, 1 H), 4.49 (s, 1 H), 3.82 (d, J = 8.80 Hz, 1 H), 3.79 (s, 3 H), 3.72 (d, J = 8.80 Hz, 1 H), 3.36-3.42 (m, 1 H), 3.28-3.35 (m, 1 H), 1.13 (s, 3 H). |

-continued

| Ex. No. | Structure | HPLC retention (min) | LCMS (ES): m/z [M + H]+ | 1H-NMR |
|---|---|---|---|---|
| 37 | 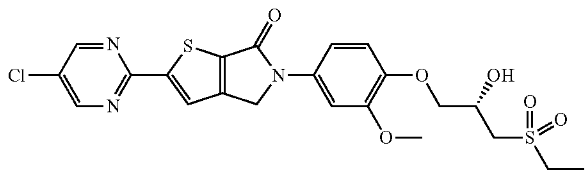 [SMILES: CCS(=O)(=O)C[C@@H](O)COc1ccc(N2Cc3cc(-c4ncc(Cl)cn4)sc3C2=O)cc1OC] | 3.256 | 524 | 1H NMR (500 MHz, DMSO-d6) δ 9.00 (s, 2 H), 8.05 (s, 1 H), 7.52 (d, J = 2.20 Hz, 1 H), 7.24 (dd, J = 8.80, 2.20 Hz, 1 H), 7.04 (d, J = 8.80 Hz, 1 H), 5.68 (d, J = 6.05 Hz, 1 H), 5.01 (s, 2 H), 4.22-4.32 (m, 1 H), 3.87-4.02 (m, 2 H), 3.80 (s, 3 H), 3.36 (dd, J = 14.85, 8.80 Hz, 1 H), 3.17-3.25 (m, 2 H), 3.08-3.17 (m, 1 H), 1.23 (t, J = 7.42 Hz, 3 H). |
| 38 | 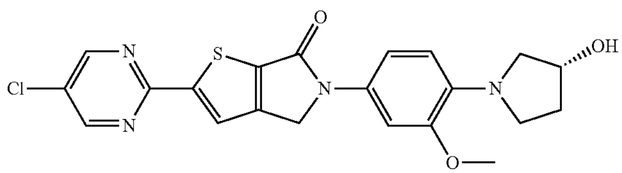 [SMILES: COc1cc(N2Cc3cc(-c4ncc(Cl)cn4)sc3C2=O)ccc1N1CC[C@@H](O)C1] | 2.605 | 443 | 1H NMR (500 MHz, CDCl3) δ 8.61 (s, 2 H) 7.86 (s, 1 H) 7.61 (d, J = 2.20 Hz, 1 H) 6.83-6.89 (m, 1 H) 6.72 (d, J = 8.25 Hz, 1 H) 4.71 (s, 1 H) 3.81 (s, 3 H) 3.51-3.58 (m, 1 H) 3.48 (dd, J = 10.45, 4.95 Hz, 1 H) 3.25 (d, J = 10.45 Hz, 1 H) 3.10-3.17 (m, 1 H) 2.11-2.21 (m, 1 H) 1.91 (d, J = 13.75 Hz, 1 H) 1.16-1.23 (m, 1 H) 0.73-0.86 (m, 1 H). |
| 39 | 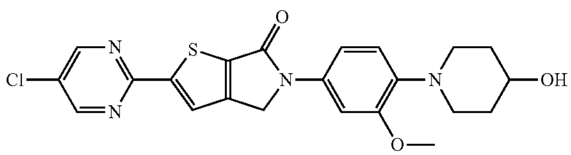 [SMILES: COc1cc(N2Cc3cc(-c4ncc(Cl)cn4)sc3C2=O)ccc1N1CCC(O)CC1] | 2.400 | 457 | 1H NMR (500 MHz, CDCl3) δ 8.68 (s, 2 H) 7.95 (s, 1 H) 7.72 (s, 1 H) 6.96 (s, 2 H) 4.81 (s, 2 H) 3.93 (s, 3 H) 3.79-3.88 (m, 1 H) 3.32-3.41 (m, 2 H) 2.73-2.85 (m, 2 H) 2.01-2.13 (m, 2 H) 1.74-1.86 (m, 2 H) 1.49-1.69 (m, 1 H). |

Example 40

2-(5-Chlorothiazol-2-yl)-5-(4-(2-hydroxy-2-methyl-propoxy)-3-methoxyphenyl)-4H-thieno[2,3-c]pyrrol-6(5H)-one

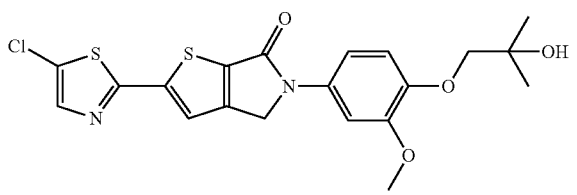 [SMILES: COc1cc(N2Cc3cc(-c4ncc(Cl)s4)sc3C2=O)ccc1OCC(C)(C)O]

Part A. 2-Bromo-5-chlorothiazole

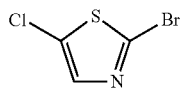

Commercially available 2-amino-5-chlorothiazole hydrochloride was liberated from its HCl salt via basification with sat. NaHCO3 followed by extraction with EtOAc (3×). The combined organic layers were dried over anhydrous Na2SO4 and concentrated to afford 5-chlorothiazol-2-amine. To a suspension of Copper(II) bromide (0.939 mL, 20.06 mmol) and tent-butyl nitrite (3.34 mL, 25.08 mmol) in 59 mL of MeCN was added a solution of 5-chlorothiazol-2-amine (2.25 g, 16.72 mmol) in 31 ml of MeCN dropwise over a period of 30 min. After addition, the reaction was allowed to stir at RT for 18 h. The reaction mixture was concentrated to near dryness, diluted with 60 ml of EtOAc and 60 mL of 2 N NaOH and filtered through a pad of CELITE®. The organic layer was separated, washed with water, brine, dried over anhydrous Na2SO4 and concentrated to afford 934 mg of the title compound as a brown oil that was carried forward without further purification: HPLC retention time: 2.548 min; LCMS (ES): m/z 200 [M+H]+.

Part B. 5-(5-Chlorothiazol-2-yl)-3-methylthiophene-2-carbaldehyde

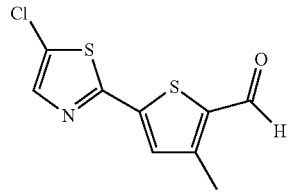

Using the procedure described in Part B of Example 1, 857 mg of 5-formyl-4-methylthiophen-2-ylboronic acid, 800 mg of Part A compound, 4.0 ml of a 2 N solution of Na2CO3 and 147 mg of PdCl2dppf in DMF (27.2 mL) afforded 200 mg of the title compound as a yellow/tan solid: 1H NMR (400 MHz, DMSO-$d_6$) δ 10.06 (1H, s), 7.99 (1H, s), 7.70 (1H, s), 2.56 (3H, s). HPLC retention time: 3.221 min; LCMS (ES): m/z 244 [M+H]$^+$.

Part C. 5-(5-Chlorothiazol-2-yl)-3-methylthiophene-2-carboxylic acid

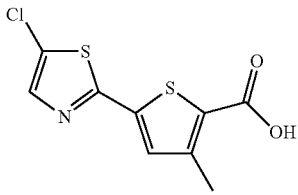

Using the procedure described in Part C of Example 1, 200 mg of Part B compound, 125 mg of sodium chlorite in 0.500 ml of water, 88 µL of 30% $H_2O_2$ and 0.388 ml of a 2.5 M solution of sodium dihydrogen phosphate in 8.2 mL of MeCN followed by 30 mg of sodium sulfite afforded 196 mg of the title compound as a light yellow solid: $^1$H NMR (500 MHz, DMSO-$d_6$) δ 13.23 (1H, s), 7.85 (1H, s), 7.53 (1H, s), 2.39 (3H, s); HPLC retention time: 3.463 min; LCMS (ES): m/z 260 [M+H]$^+$.

Part D. 3-(Bromomethyl)-5-(5-chlorothiazol-2-yl)thiophene-2-carboxylic acid

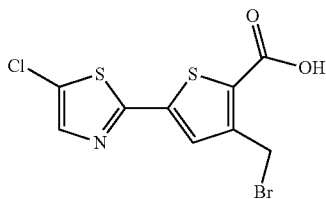 [SMILES: O=C(O)c1sc(-c2ncc(Cl)s2)cc1CBr]

Using the procedure described in Part D of Example 1, 192 mg of Part C compound, 94 µL of HMDS, 132 mg of NBS and 12.2 mg of AIBN in 0.637 mL of $CCl_4$ afforded 134 mg of the title compound as a light orange/yellow solid which was carried forward without further purification: HPLC retention time: 3.633 min; LCMS (ES): m/z 340 [M+H]$^+$.

Part E. 3-(Chloromethyl)-5-(5-chlorothiazol-2-yl)-N-(4-(2-hydroxy-2-methylpropoxy)-3-methoxyphenyl)thiophene-2-carboxamide

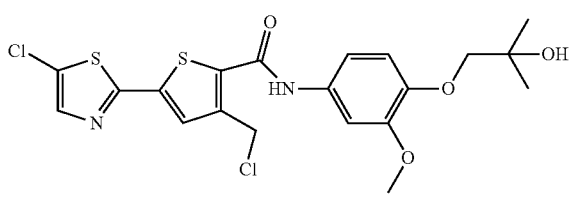 [SMILES: COc1cc(NC(=O)c2sc(-c3ncc(Cl)s3)cc2CCl)ccc1OCC(C)(C)O]

Using the procedure described in Part E of Example 1, 50 mg of Part D compound, 32.8 mg of 1-(4-amino-2-methoxyphenoxy)-2-methylpropan-2-ol and 28.3 mg of EDC in 0.738 mL of DMF afforded 17.5 mg of the title compound as a yellow solid which was carried forward without further purification: HPLC retention time: 3.838 min; LCMS (ES): m/z 487 [M+H]$^+$.

Part F. 2-(5-Chlorothiazol-2-yl)-5-(4-(2-hydroxy-2-methylpropoxy)-3-methoxyphenyl)-4H-thieno[2,3-c]pyrrol-6(5H)-one

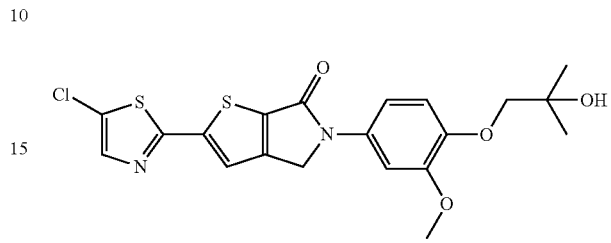

Using the procedure described in Part F of Example 1, 17.1 mg of Part E compound and 4.8 mg of $K_2CO_3$ in 1.40 mL of DMF afforded 7.5 mg of the title compound as a yellow solid: $^1$H NMR (500 MHz, $CD_3OD$) δ 7.72 (1H, s), 7.66 (1H, s), 7.55 (1H, br. s.), 7.11 (1H, br. s.), 7.00 (1H, d, J=8.25 Hz), 4.90 (2H, br. s.), 3.90 (3H, s), 3.80 (2H, s), 1.32 (6H, s). HPLC retention time: 3.600 min; LCMS (ES): m/z 451 [M+H]$^+$.

Example 41

5-(4-(2-Hydroxy-2-methylpropoxy)-3-methoxyphenyl)-2-(6-methoxypyridin-3-yl)-4H-thieno[3,2-c]pyrrol-6(5H)-one, trifluoroacetic acid salt

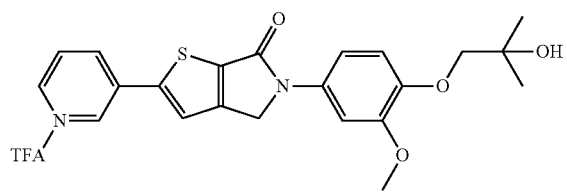

Part A. 5-Bromo-3-methylthiophene-2-carboxylic acid

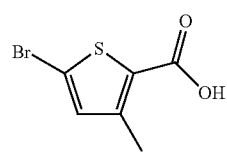

Using the procedure described in Part C of Example 1, 1.000 g of Part A compound in Example 1, 0.744 g of sodium chlorite in 12.4 ml of water, 0.523 mL of 30% $H_2O_2$ and 0.201 ml of a 2.5 M solution of sodium dihydrogen phosphate in 49 mL of MeCN followed by 100 mg of sodium sulfite afforded 853 mg (79% yield) of the title compound as a yellow solid:

$^1$H NMR (500 MHz, DMSO-d$_6$) δ 13.20 (1H, br. s.), 7.21 (1H, s), 2.43 (3H, s). HPLC retention time: 3.090 min; LCMS (ES): m/z 221 [M+H]$^+$.

Part B.
5-Bromo-3-(bromomethyl)thiophene-2-carboxylic acid

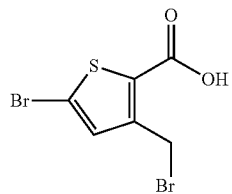 [SMILES: O=C(O)c1sc(Br)cc1CBr]

Using the procedure described in Part D of Example 1, 850 mg of Part A compound, 0.496 mL of HMDS, 692 mg of NBS and 64 mg of AIBN in 3.35 mL of CCl$_4$ afforded 545 mg (47% yield) of the title compound as a light yellow solid which was carried forward without further purification.

Part C. 2-Bromo-5-(4-(2-hydroxy-2-methylpropoxy)-3-methoxyphenyl)-4H-thieno[3,2-c]pyrrol-6(5H)-one

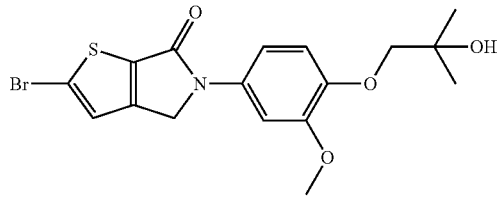 [SMILES: COc1cc(N2Cc3cc(Br)sc3C2=O)ccc1OCC(C)(C)O]

A solution of Part B compound (545 mg, 1.817 mmol), 1-(4-amino-2-methoxyphenoxy)-2-methylpropan-2-ol (403 mg, 1.908 mmol) and EDC (418 mg, 2.180 mmol) in DMF (9.1 mL) was allowed to stir at RT for 18 h. The reaction mixture was diluted with water (25 mL) and extracted with EtOAc (3×20 mL). The organic layers were washed with water and brine, dried over anhydrous Na$_2$SO$_4$ and concentrated to a crude brown solid. To a solution of this material in DMF (70 mL) was added K$_2$CO$_3$ (251 mg, 1.817 mmol). After stirring at RT for 1H, the reaction was diluted with water (100 mL) and extracted with EtOAc (3×75 mL). The combined organic layers were washed with water, brine, dried over anhydrous Na$_2$SO$_4$ and concentrated. The residue was purified by flash chromatography (silica gel, hexanes:EtOAc, 100:0 to 0:100) to afford 284 mg (38% yield) of the title compound as a light yellow solid: $^1$H NMR (400 MHz, CD$_3$OD) δ 7.50 (1H, d, J=2.64 Hz), 7.33 (1H, s), 7.00-7.17 (1H, m), 6.99 (1H, d, 8.79 Hz), 4.87 (2H, s), 3.88 (3H, s), 3.79 (2H, s), 1.29-1.35 (6H, m). HPLC retention time: 3.246 min; LCMS (ES): m/z 414 [M+H]$^+$.

Part D. 5-(4-(2-Hydroxy-2-methylpropoxy)-3-methoxyphenyl)-2-(6-methoxypyridin-3-yl)-4H-thieno[3,2-c]pyrrol-6(5H)-one, trifluoroacetic acid salt

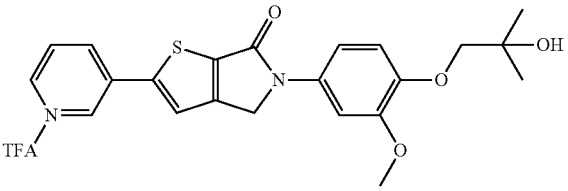

To a mixture of Part C compound (25.0 mg, 0.061 mmol) and Pd(PPh$_3$)$_4$ (2.1 mg, 1.82 umol) in degassed DMF (0.610 mL) was added a 2N solution of Na$_2$CO$_3$ (76 μL, 0.152 mmol) followed by pyridin-3-ylboronic acid (8.20 mg, 0.067 mmol) and the reaction mixture was heated to 100° C. for 1 h. Upon cooling to RT, the reaction mixture was diluted with EtOAc (10 mL), washed with water, brine, dried over Na$_2$SO$_4$, concentrated and purified by Prep. HPLC. The desired fraction was concentrated and lyophilized to afford 16.2 mg of the title compound as a yellow solid as the TFA salt: $^1$H NMR (500 MHz, CD$_2$Cl$_2$) δ 9.05 (1H, s), 8.65 (1H, d, J=5.50 Hz), 8.33 (1H, d, J=8.25 Hz), 7.66-7.90 (1H, m), 7.40-7.60 (2H, m), 6.98 (1H, dd, J=8.52, 2.47 Hz), 6.87 (1H, d, J=8.25 Hz), 4.67-4.95 (2H, m), 3.81 (3H, s), 3.75 (2H, s), 1.24 (6H, s); HPLC retention time: 2.550 min; LCMS (ES): m/z 411 [M+H]$^+$.

Example 42 to 49

These examples were prepared following the method described in Example 1 from commercially available boronic acids respectively. HCl salts were prepared via neutralization of the corresponding TFA salts using sat. NaHCO$_3$ followed by dissolution in CH$_2$Cl$_2$ and subjection to 1.0 M HCl in ether. The material was then lyophilized to afford the corresponding HCl salt.

| Ex. No. | Structure | HPLC retention (min) | LCMS (ES): m/z [M + H]$^+$ | $^1$H-NMR |
|---|---|---|---|---|
| 42 | 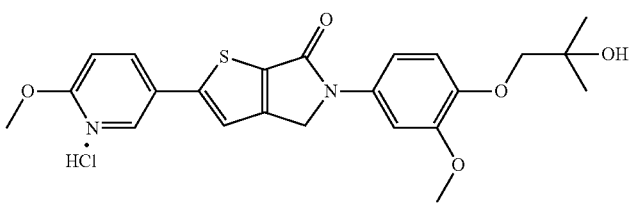 [SMILES: COc1ccc(-c2cc3c(s2)C(=O)N(c2ccc(OCC(C)(C)O)c(OC)c2)C3)cn1 ; Cl] | 3.53 | 441 | $^1$H NMR (500 MHz, CD$_2$Cl$_2$) δ 8.41 (1 H, d, J = 2.20 Hz), 7.79 (1 H, dd, J = 8.80, 2.20 Hz), 7.53 (1 H, d, J = 2.20 Hz), 7.18 (1 H, s), 6.97 (1 H, dd, J = 8.52, 2.47 Hz), 6.87 (1 H, d, J = 8.25 Hz), 6.77 (1 H, d, J = 8.25 Hz), 4.69 (2 H, s), 3.91 (3 H, s), 3.81 (3 H, s), 3.73 (2 H, s), 1.23 (6 H, s). |

-continued

| Ex. No. | Structure | HPLC retention (min) | LCMS (ES): m/z [M + H]⁺ | ¹H-NMR |
|---|---|---|---|---|
| 43 | (pyridin-4-yl thienopyrrolone structure, ·HCl) | 2.14 | 411 | ¹H NMR (500 MHz, CD₃OD) δ 8.69 (2 H, d, J = 3.85 Hz), 8.21 (2 H, d, J = 4.40 Hz), 8.05 (1 H, s), 7.48 (1 H, s), 7.06 (1 H, d, J = 8.80 Hz), 6.92 (1 H, d, J = 8.80 Hz), 4.90 (2 H, s), 3.81 (3 H, s), 3.71 (2 H, s), 1.23 (6 H, s). |
| 44 | (6-chloropyridin-3-yl structure) | 3.38 | 445 | ¹H NMR (400 MHz, CD₂Cl₂) δ 8.61 (1 H, d, J = 2.20 Hz), 7.83 (1 H, dd, J = 8.35, 2.64 Hz), 7.53 (1 H, d, J = 2.64 Hz), 7.34 (1 H, d, J = 8.35 Hz), 7.30 (1 H, s), 6.94-7.01 (1 H, m), 6.83-6.91 (1 H, m), 4.71 (2 H, s), 3.81 (3 H, s), 3.73 (2 H, s), 1.23 (6 H, s); |
| 45 | (6-methylpyridin-3-yl structure, ·TFA) | 2.39 | 425 | ¹H NMR (400 MHz, CD₃OD) δ 8.85 (1 H, d, J = 2.20 Hz), 8.30 (1 H, dd, J = 8.35, 2.20 Hz), 7.63 (1 H, s), 7.58 (1 H, d, J = 8.35 Hz), 7.47 (1 H, d, J = 2.64 Hz), 7.05 (1 H, dd, J = 8.57, 2.42 Hz), 6.92 (1 H, d, J = 8.79 Hz), 4.86 (2 H, s), 3.81 (3 H, s), 3.71 (2 H, s), 2.60 (3 H, s), 1.23 (6 H, s) |
| 46 | (3,4-dichlorophenyl structure) | 4.05 | 478 | ¹H NMR (500 MHz, CD₂Cl₂) δ 7.75 (1 H, s), 7.57 (1 H, d, J = 2.20 Hz), 7.49 (2 H, s), 7.31 (1 H, s), 7.01 (1 H, dd, J = 8.80, 2.75 Hz), 6.91 (1 H, d, J = 8.80 Hz), 4.74 (2 H, s), 3.86 (3 H, s), 3.78 (2 H, s), 1.27 (6 H, s) |
| 47 | (4-trifluoromethoxyphenyl structure) | 3.92 | 494 | ¹H NMR (500 MHz, CD₂Cl₂) δ 7.64 (2 H, d, J = 8.80 Hz), 7.51 (1 H, d, J = 2.20 Hz), 7.26 (1 H, s), 7.23 (2 H, d, J = 8.25 Hz), 6.96 (1 H, dd, J = 8.80, 2.20 Hz), 6.85 (1 H, d, J = 8.80 Hz), 4.71 (2 H, s), 3.84 (3 H, s), 3.72 (2 H, s), 1.23 (6 H, s) |
| 48 | (4-trifluoromethylphenyl structure) | 3.87 | 478 | ¹H NMR (500 MHz, CD₂Cl₂) δ 7.72 (2 H, d, J = 8.25 Hz), 7.62 (2 H, d, J = 7.70 Hz), 7.53 (1 H, d, J = 2.20 Hz), 7.35 (1 H, s), 6.97 (1 H, dd, J = 8.80, 2.20 Hz), 6.87 (1 H, d, J = 8.80 Hz), 4.71 (2 H, s), 3.81 (3 H, s), 3.73 (2 H, s), 1.23 (6 H, s). |

Example 49

5-(4-(2-Hydroxy-2-methylpropoxy)-3-methoxyphenyl)-2-(pyridin-2-yl)-4H-thieno[2,3-c]pyrrol-6(5H)-one, trifluoroacetic acid salt

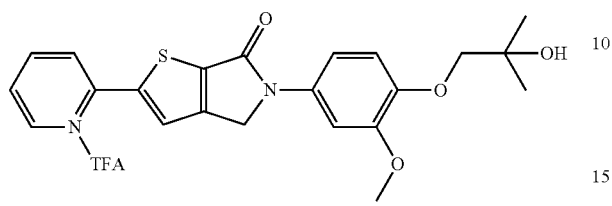

Part A.
3-Methyl-5-(pyridin-2-yl)thiophene-2-carbaldehyde

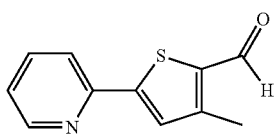

To a N$_2$ purged mixture of Part A compound in Example 1 (100 mg, 0.488 mmol) and 2-(trimethylstannyl)pyridine (0.134 mL, 0.780 mmol) in degassed DMF (1.50 mL) was added Pd(PPh$_3$)$_4$ (14.09 mg, 0.012 mmol) and the reaction was allowed to stir at 100° C. for 4.0 h. Upon cooling to RT, the reaction mixture was diluted with water (15 mL) and extracted with EtOAc (3×10 mL). The combined organic layers were washed with brine, dried over anhydrous Na$_2$SO$_4$, concentrated and purified by flash chromatography (silica gel, CH$_2$Cl$_2$:MeOH, 100:0 to 90:10) to afford 41 mg (41% yield) of the title compound as a yellow solid: $^1$H NMR (500 MHz, CDCl$_3$) δ 10.04 (1H, s), 8.62 (1H, d, J=3.85 Hz), 7.74 (1H, t, J=7.70 Hz), 7.66-7.71 (1H, m), 7.47 (1H, s), 7.16 (1H, s), 2.60 (3H, s). HPLC retention time: 2.360 min; LCMS (ES): m/z 204 [M+H]$^+$.

Part B.
3-Methyl-5-(pyridin-2-yl)thiophene-2-carboxylic acid, hydrochloric acid salt

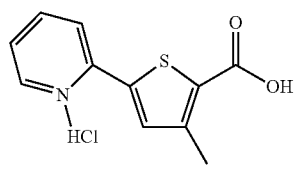

Using the procedure describe in Part C of Example 1, 41 mg of Part A compound, 30.8 mg of sodium chlorite in 0.500 mL of water, 83 µL of a 2.5 M aqueous solution of sodium dihydrogen phosphate and 13 µL of 30% H$_2$O$_2$ in 2.02 ml of MeCN afforded 22 mg of the title compound as a light yellow solid: $^1$H NMR (400 MHz, CD$_3$OD) δ 8.51 (1H, d, J=4.83 Hz), 7.78-7.92 (2H, m), 7.54 (1H, s), 7.32 (1H, ddd, J 6.81, 4.83, 1.98 Hz), 2.54 (3H, s); HPLC retention time: 2.466 min; LCMS (ES): m/z 220 [M+H]$^+$.

Part C. 3-(Chloromethyl)-5-(pyridin-2-yl)thiophene-2-carboxylic acid, hydrochloric acid salt

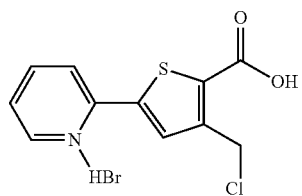

Using the procedure described in Part D of Example 1, 22 mg of Part B compound, 11 µL of HMDS, 15.3 mg of NBS and 1.4 mg of AIBN in 74 µL of CCl$_4$ afforded 36.4 mg of the title compound as a tan solid which was carried forward without further purification: HPLC retention time: 2.818 min; LCMS (ES): m/z 254 [M+H]$^+$.

Part D. 5-(4-(2-Hydroxy-2-methylpropoxy)-3-methoxyphenyl)-2-(pyridin-2-yl)-4H-thieno[2,3-c]pyrrol-6(5H)-one, trifluoroacetic acid salt

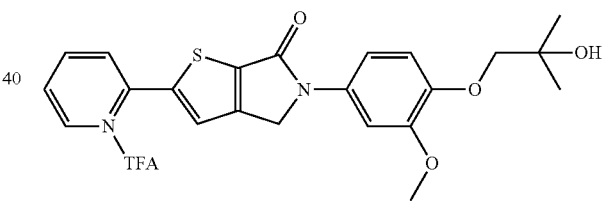

A solution of Part E compound (36.4 mg, 0.125 mmol), 1-(4-amino-2-methoxyphenoxy)-2-methylpropan-2-ol (26.5 mg, 0.125 mmol) and EDC (29.0, 0.151 mmol) in DMF (0.627 mL) was allowed to stir at RT for 2 h. The reaction was diluted with EtOAc (10 mL), washed with water (15 mL), 1N HCl (15 mL), brine, dried over anhydrous Na$_2$SO$_4$, concentrated and air dried under vacuum. This crude material was dissolved in DMF (5 mL) and K$_2$CO$_3$ (17.3 mg, 0.125 mmol) was added. The reaction was allowed to stir at RT for 1 h at which point it was diluted with water (20 mL). The solid formed was filtered and purified by Prep HPLC to afford 3.5 mg (5% yield) of the title compound as an orange solid: $^1$H NMR (500 MHz, CD$_3$OD) δ 8.54 (1H, d, J=4.95 Hz), 7.91-7.97 (1H, m), 7.83-7.90 (1H, m), 7.78 (1H, s), 7.56 (1H, d, J=2.75 Hz), 7.31-7.41 (1H, m), 7.13 (1H, dd, J=8.80, 2.20

Hz), 7.00 (1H, d, J=8.80 Hz), 4.91 (2H, s), 3.90 (3H, s), 3.80 (2H, s), 1.32 (6H, s)HPLC retention time: 3.113 min; LCMS (ES): m/z 411 [M+H]$^+$.

Example 50

2-(5-Chlorothiophen-2-yl)-5-(4-(2-hydroxy-2-methylpropoxy)-3-methoxyphenyl)-4H-thieno[2,3-c]pyrrol-6(5H)-one

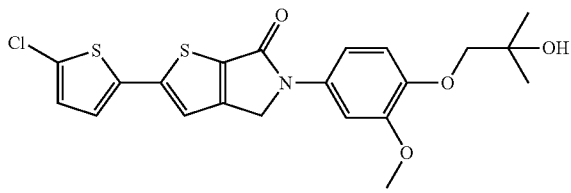 [SMILES: COc1cc(N2Cc3cc(-c4ccc(Cl)s4)sc3C2=O)ccc1OCC(C)(C)O]

In a sealed tube were added a degassed mixture of the compound in Part C of Example 41 (50.0 mg, 0.121 mmol), 5,5,5',5'-tetramethyl-2,2'-bi(1,3,2-dioxaborinane) (38.4 mg, 0.170 mmol), 2-bromo-5-chlorothiophene (22.17 μL, 0.121 mmol) and potassium acetate (29.8 mg, 0.303 mmol) in a mixture of 1,4-dioxane (303 μL) and DMSO (303 μL). 1,1' Bis(diphenylphisphino)ferrocenedichloro palladium(II) dichloride (7.98 mg, 10.91 μmol) was added and the reaction was allowed to stir at 90° C. for 16 h. Upon cooling, the reaction mixture was diluted with EtOAc (10 mL) and subsequently washed with water and brine. The organic layer was dried over anhydrous Na$_2$SO$_4$, concentrated, and purified by Prep. HPLC. The desired fraction was concentrated and lyophilized to afford 6.8 mg of the title compound as a light yellow solid: $^1$H NMR (400 MHz, CD$_3$OD) δ 7.54 (1H, d, J=2.64 Hz), 7.32 (1H, s), 7.25 (1H, d, J=3.95 Hz), 7.11 (1H, dd, J=8.57, 2.42 Hz), 6.93-7.06 (2H, m), 4.88 (2H, s), 3.89 (3H, s), 3.79 (2H, s), 1.32 (6H, s); HPLC retention time: 3.896 min; LCMS (ES): m/z 450 [M+H]$^+$.

Example 51

2-(3-Chloro-1H-pyrazol-1-yl)-5-(4-(2-hydroxy-2-methylpropoxy)-3-methoxyphenyl)-4H-thieno[2,3-c]pyrrol-6(5H)-one

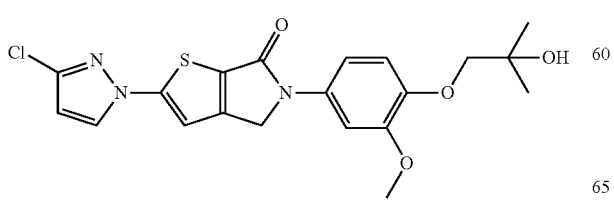

Part A. 5-(3-chloro-1H-pyrazol-1-yl)-3-methylthiophene-2-carbaldehyde

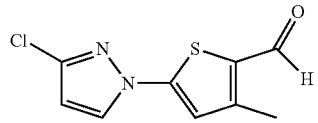

A sealed tube was charged with Copper(I) oxide (5.82 μL, 0.244 mmol), salicylaldoxime (134 mg, 0.975 mmol), 3-chloro-1H-pyrazole (500 mg, 4.88 mmol), Cs$_2$CO$_3$ (3178 mg, 9.75 mmol) and Part A compound of Example 1(150 mg, 7.32 mmol) and MeCN (4.877 mL). The tube was purged with N$_2$ and the reaction stirred at 82° C. for 5 h. After cooling to RT, the mixture was diluted with CH$_2$Cl$_2$ (10 mL) and filtered through a pad of CELITE®. The filtrate was concentrated and purified by flash chromatography (silica gel, hexanes:EtOAc, 100:0 to 50:50) to afford 420 mg (38% yield) of the title compound as a brown solid: $^1$H NMR (500 MHz, CD$_3$OD) δ 9.88 (1H, s), 8.34 (1H, s), 7.62 (1H, s), 7.07 (1H, s), 2.48 (3H, s). HPLC retention time 2.923 min., LCMS (ES): m/z 227 [M+H]$^+$.

Part B. 5-(3-Chloro-1H-pyrazol-1-yl)-3-methylthiophene-2-carboxylic acid

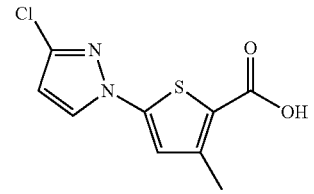

Using the procedure described in Part C of Example 1, 283 mg of sodium chlorite in 2.50 ml of water, 420 mg of Part A compound, 0.119 mL of 30% H$_2$O$_2$ and 0.763 ml of a 2.5 M solution of sodium dihydrogen phosphate in 18.5 mL MeCN afforded 350 mg (78% yield) of the title compound as a yellow solid: HPLC retention time: 3.113 min; LCMS (ES): m/z 243 [M+H]$^+$.

Part C. 3-(Bromomethyl)-5-(3-chloro-1H-pyrazol-1-yl)thiophene-2-carboxylic acid

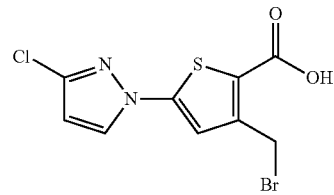 [SMILES: O=C(O)c1sc(-n2ccc(Cl)n2)cc1CBr]

Using the procedure described in Part D of Example 1, 350 mg of Part A compound, 0.184 mL of HMDS, 257 mg of NBS and 24 mg of AIBN in 1.24 mL of CCl$_4$ afforded 337 mg (72% yield) of the title compound as a yellow solid which was carried forward without further purification: HPLC retention time: 3.325 min; LCMS (ES): m/z 323 [M+H]+.

Part D. 2-(3-Chloro-1H-pyrazol-1-yl)-5-(4-(2-hydroxy-2-methylpropoxy)-3-methoxyphenyl)-4H-thieno[2,3-c]pyrrol-6(5H)-one

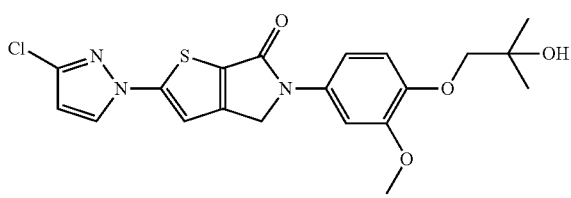 [SMILES: COc1cc(N2Cc3cc(-n4ccc(Cl)n4)sc3C2=O)ccc1OCC(C)(C)O]

A solution of Part C compound (150 mg, 0.466 mmol), 1-(4-amino-2-methoxyphenoxy)-2-methylpropan-2-ol (133 mg, 0.630 mmol) and EDC (89 mg, 0.466 mmol) in DMF (2.332 mL) was allowed to stir at RT for 4 h. The reaction was diluted with EtOAc (15 mL), washed with water (25 mL), 1N HCl, brine, dried over anhydrous Na$_2$SO$_4$, concentrated and air dried under vacuum. This crude material was dissolved in DMF (15 mL) and K$_2$CO$_3$ (64.5 mg, 0.466 mmol) was added. The reaction was allowed to stir at RT for 2 h at which point it was diluted with water (25 mL). The solid formed was filtered and purified by flash chromatography (silica gel, hexanes:EtOAc, 100:0 to 0:100) to afford 39 mg (20% yield) of the title compound as a yellow solid: $^1$H NMR (500 MHz, DMSO-d$_6$) δ 8.94 (1H, s), 7.96 (1H, s), 7.57 (1H, s), 7.49 (1H, d, J=2.75 Hz), 7.19 (1H, dd, J=8.80, 2.75 Hz), 6.99 (1H, d, J=8.80 Hz), 4.98 (2H, s), 4.57 (1H, s), 3.79 (3H, s), 3.68 (2H, s), 1.20 (6H, s). HPLC retention time: 3.43 min; LCMS (ES): m/z 434 [M+H]+.

Example 52

2-(4-Chlorophenyl)-5-(4-(2-hydroxy-2-methylpropoxy)-3-methoxyphenyl)-4H-pyrrolo[3,4-d]thiazol-6(5H)-one

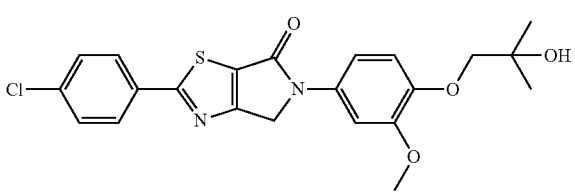 [SMILES: COc1cc(N2Cc3nc(-c4ccc(Cl)cc4)sc3C2=O)ccc1OCC(C)(C)O]

Part A. 4-(Bromomethyl)-2-(4-chlorophenyl)thiazole-5-carboxylic acid

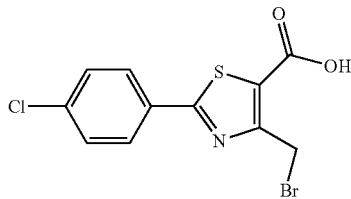 [SMILES: O=C(O)c1sc(-c2ccc(Cl)cc2)nc1CBr]

Following the procedure described in Part D of Example 1, 1.00 g of commercially available of 2-(4-chlorophenyl)-4-methylthiazole-5-carboxylic acid, 0.502 mL of HMDS, 0.702 g of NBS and 32 mg of AIBN in 3.40 mL of CCl$_4$ afforded the title compound (0.940 g, 72% yield) as a yellow/orange solid: $^1$H NMR (500 MHz, DMSO-d$_6$) δ 11.06 (1H, br. s.), 8.02 (2H, d, J=8.25 Hz), 7.61 (2H, d, J=8.80 Hz), 5.01 (2H, s); HPLC retention time: 3.591 min; LCMS (ES): m/z 334 [M+H]+.

Part B. 2-(4-(Chlorophenyl)-N-(4-(2-hydroxy-2-methylpropoxy)-3-methoxyphenyl)-4-(hydroxymethyl)thiazole-5-carboxamide

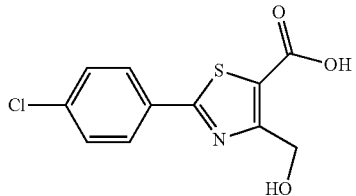 [SMILES: O=C(O)c1sc(-c2ccc(Cl)cc2)nc1CO]

A mixture of Part A compound (1.05 g, 3.16 mmol) and NaOH (0.126 g, 3.16 mmol) in water (15.8 mL) was allowed to stir at reflux for 4.5 h. Upon cooling, the reaction mixture was diluted with 1N HCl (25 mL). The solid formed was filtered, washed well with water and air dried under vacuum to afford 656 mg (77% yield) of the title compound as a colorless solid that was carried forward without further purification: HPLC retention time: 3.108 min; LCMS (ES): m/z 270 [M+H]+.

Part C. 2-(4-Chlorophenyl)-N-(4-(2-hydroxy-2-methylpropoxy)-3-methoxyphenyl)-4-(hydroxymethyl)thiazole-5-carboxamide

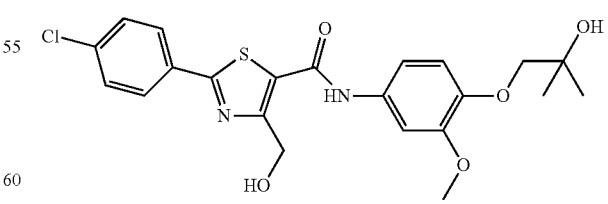

A solution of Part B compound (262 mg, 0.971 mmol), 1-(4-amino-2-methoxyphenoxy)-2-methylpropan-2-ol (215 mg, 1.020 mmol), EDC (223 mg, 1.166 mmol) and HOBT (179 mg, 1.166 mmol) in DMF (4.86 mL) was allowed to stir at RT for 24 h. The reaction mixture was diluted with EtOAc (10 mL), washed with sat. NaHCO₃ (3×15 mL) and brine. The organic layer was dried over anhydrous Na₂SO₄ and concentrated. The residue was purified by flash chromatography (silica gel, hexanes:EtOAc, 100:0 to 0:100) to afford 67 mg of the title compound as a yellow solid: ¹H NMR (500 MHz, CDCl₃) δ 9.89 (1H, br. s.), 7.75 (2H, d, J=8.80 Hz), 7.38 (1H, d, J=2.20 Hz), 7.32 (2H, d, J=8.80 Hz), 6.86 (1H, dd, J=8.52, 2.47 Hz), 6.69-6.81 (1H, m), 5.01 (2H, d, J=6.05 Hz), 3.80 (3H, s), 3.74 (2H, s), 2.85 (1H, s), 1.27 (6H, s); HPLC retention time: 3.783 min; LCMS (ES): ink 463 [M+H]⁺.

Part D. 2-(4-Chlorophenyl)-5-(4-(2-hydroxy-2-methylpropoxy)-3-methoxyphenyl)-4H-pyrrolo[3,4-d]thiazol-6(5H)-one

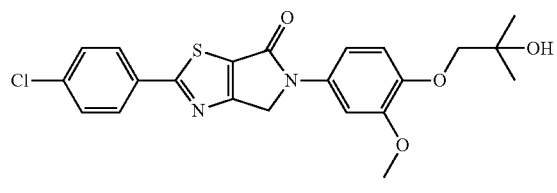 [SMILES: COc1cc(N2Cc3nc(-c4ccc(Cl)cc4)oc3C2=O)ccc1OCC(C)(C)O]

To a solution of Part C compound (52.0 mg, 0.112 mmol) in THF (960 μL) was added PPh₃ (35.4 mg, 0.135 mmol) and DEAD (53.4 μL, 0.135 mmol) and the reaction was allowed to stir at RT for 1.0 h. After concentration, the residue was purified by flash chromatography (silica gel, hexanes:EtOAc, 100:0 to 50:50) to afford 10.1 mg of the title compound as a light yellow solid: ¹H NMR (400 MHz, CDCl₃) δ 7.88 (d, J=8.79 Hz, 2H), 7.55 (s, 1H), 7.41 (d, J=8.79 Hz, 2H), 6.80-6.97 (m, 2H), 4.82 (s, 2H), 3.84 (s, 3H), 3.78 (s, 2H), 2.67 (s, 1H), 1.28 (s, 6H); HPLC retention time: 3.834 min; LCMS (ES): m/z 445 [M+H]⁺.

Example 53

2-(4-Chlorophenyl)-5-(4-(2-hydroxy-2-methylpropoxy)-3-methoxyphenyl)-4H-pyrrolo[3,4-d]oxazol-6(5H)-one

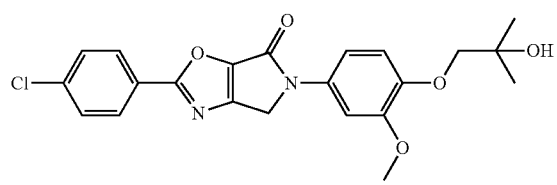

Part A. 2-(4-Chlorobenzamido)propanoic acid

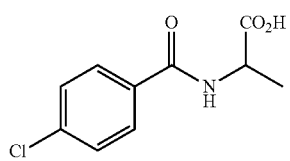

To a solution of L-Alanine (2.67 g, 30.0 mmol) and KOH (3.90 g, 69.5 mmol) in water (50.0 mL) was added 4-chlorobenzoyl chloride (5.25 g, 30.0 mmol). After stirring at RT for 16H, the reaction mixture was cooled to 0° C., acidified to pH=2 with 10 M HCl and extracted with EtOAc (3×75 mL). The combined organic layers were washed with brine, dried over anhydrous Na₂SO₄, concentrated and air dried under vacuum to afford 5.80 g (85% yield) of the title compound as a white solid that was carried forward without further purification: ¹H NMR (500 MHz, DMSO-d₆) δ 12.62 (1H, br. s.), 8.76 (1H, d, J=7.15 Hz), 7.90 (2H, d, J=8.25 Hz), 7.55 (2H, d, J=8.25 Hz), 4.40 (1H, qd, J=7.33, 7.15 Hz), 1.38 (3H, d, J=7.15 Hz); HPLC retention time: 2.223 min; LCMS (ES): m/z 228 [M+H]⁺.

Part B. Methyl 2-(4-chlorophenyl)-4-methyloxazole-5-carboxylate

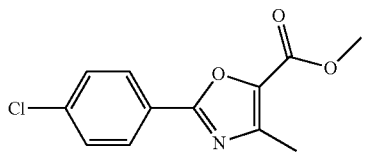 [SMILES: COC(=O)c1oc(-c2ccc(Cl)cc2)nc1C]

To a slurry of Part A compound (5.000 g, 21.96 mmol) in THF (220 mL) was added oxalyl chloride (19.23 mL, 220 mmol) and the reaction was allowed to stir RT overnight. The solvent was removed in vacuo and trace oxalyl chloride was removed via toluene azeotropically. The residue was cooled to 0° C. prior to addition of NEt₃ (4.59 mL, 32.9 mmol) followed by MeOH (145 mL). The ice bath was removed and the reaction was allowed to stir at RT for 3 h. Following concentration, the residue was purified by flash chromatography (silica gel, hexanes:EtOAc, 100:0 to 40:60) to afford 2.25 g (41% yield) of the title compound as a white solid: ¹H NMR (500 MHz, CDCl₃) δ 8.06 (d, J=8.8 Hz, 2H), 7.46 (d, J=8.2 Hz, 2H), 3.95 (s, 3H), 2.54 (s, 3H); HPLC retention time: 3.596 min; LCMS (ES): m/z 252 [M+H]⁺.

Part C. 2-(4-Chlorophenyl)-4-methyloxazole-5-carboxylic acid

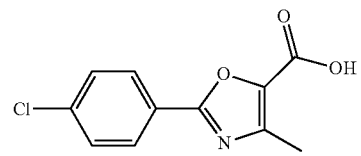 [SMILES: Cc1nc(-c2ccc(Cl)cc2)oc1C(=O)O]

To a solution of Part B compound (2.25 g, 8.94 mmol) in EtOH (85 mL) and water (4.47 mL) was added sodium hydroxide (358 mg, 8.94 mmol) and the reaction mixture was allowed to reflux for 1.5 h. Following concentration, 1 N HCl (100 mL) and water (100 mL) were added and the solid formed was filtered, washed well with water and air dried under vacuum to afford 1.89 g (89% yield) of the title compound as a colorless solid that was carried forward without further purification: ¹H NMR (500 MHz, DMSO-d₆) δ 13.54

(s, 1H), 7.93 (d, J=8.25 Hz, 2H), 7.56 (d, J=8.80 Hz, 2H), 2.36 (s, 3H); HPLC retention time: 3.298 min; LCMS (ES): m/z 238 [M+H]⁺.

Part D. 4-(Bromomethyl)-2-(4-chlorophenyl)oxazole-5-carboxylic acid

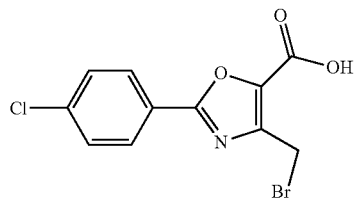

Using the procedure described in Part D of Example 1, 890 mg of Part C compound, 0.477 mL of HMDS, 0.667 g of NBS and 31 mg of AIBN in 3.23 mL of CCl₄ afforded 1.03 g of the title compound as a tan solid: ¹H NMR (400 MHz, methanol-d₃) δ 8.09 (2H, d, J=8.79 Hz), 7.57 (2H, d, J=8.79 Hz), 4.76 (2H, s); HPLC retention time: 3.451 min; LCMS (ES): m/z 318 [M+H]⁺.

Part E. 4-(Bromomethyl)-2-(4-chlorophenyl)-N-(4-(2-hydroxy-2-methylpropoxy)-3-methoxyphenyl) oxazole-5-carboxamide

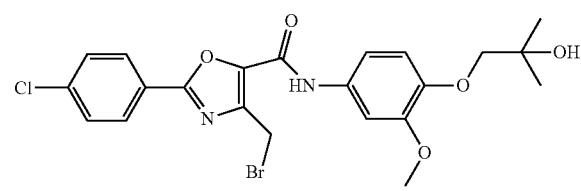 [SMILES: COc1cc(NC(=O)c2oc(-c3ccc(Cl)cc3)nc2CBr)ccc1OCC(C)(C)O]

A solution of Part D compound (100 mg, 0.316 mmol), 1-(4-amino-2-methoxyphenoxy)-2-methylpropan-2-ol (70.1 mg, 0.332 mmol), EDC (72.7 mg, 0.379 mmol) and HOBT (58.1 mg, 0.379 mmol) in 1,2-DCE (1.58 mL) was allowed to stir at RT for 30 min. The reaction mixture was diluted with EtOAc (10 mL), washed with sat. NaHCO₃ (3×15 mL), water and brine. The organic layer was dried over anhydrous Na₂SO₄, concentrated and purified by flash chromatography (silica gel, CH₂Cl₂:EtOAc, 100:0 to 10:90) to afford 57 mg of the title compound as a light yellow solid: ¹H NMR (500 MHz, CDCl₃) δ 8.00 (d, J=8.80 Hz, 2H), 7.78-7.87 (m, 1H), 7.43 (d, J=8.25 Hz, 2H), 7.39 (d, J=2.75 Hz, 1H), 6.90-6.98 (m, 1H), 6.84 (d, J=8.80 Hz, 1H), 4.79 (s, 2H), 3.83 (s, 3H), 3.76 (s, 2H), 1.28 (s, 6H); HPLC retention time: 3.938 min; LCMS (ES): m/z 511 [M+H]⁺.

Part F. 2-(4-Chlorophenyl)-5-(4-(2-hydroxy-2-methylpropoxy)-3-methoxyphenyl)-4H-pyrrolo[3,4-d]oxazol-6(5H)-one

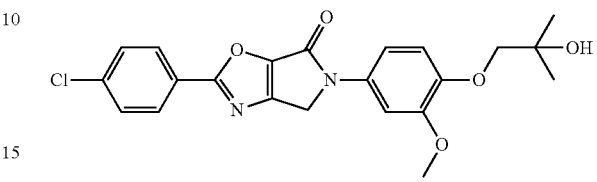

To a solution of Part E compound (25.00 mg, 0.049 mmol) in DMF (4.90 mL) was added K₂CO₃ (13.56 mg, 0.098 mmol). After stirring at RT for 18H, the reaction mixture was diluted with water (5 mL) and extracted with CH₂Cl₂ (3×15 mL). The combined organic layers were washed with water, brine, dried over anhydrous Na₂SO₄ and concentrated. This resulting material was purified by Prep. HPLC. The desired fraction was concentrated and lyophilized to afford 3.0 mg of the title compound as a yellow solid: ¹H NMR (400 MHz, CDCl₃) δ δ 8.09 (d, J=8.79 Hz, 2H), 7.41-7.60 (m, 3H), 6.95 (s, 2H), 4.75 (s, 2H), 3.91 (s, 3H), 3.84 (s, 2H), 1.35 (s, 6H), 1.25 (s, 1H); HPLC retention time: 3.706 min; LCMS (ES): m/z 429 [M+H]⁺.

Example 54

2-(4-Chlorophenyl)-5-(4-(2-hydroxy-2-methylpropoxy)-3-methoxyphenyl)-4H-furo[3,2-c]pyrrol-6(5H)-one

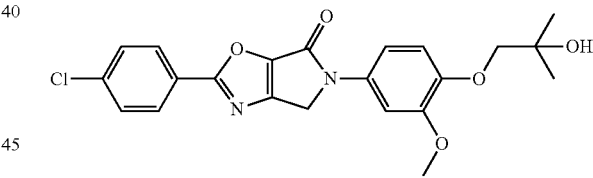

Part A. Methyl 5-bromo-3-methylfuran-2-carboxylate

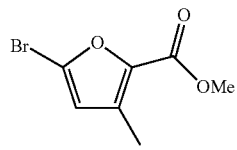

To a solution of methyl 3-methylfuran-2-carboxylate (3.0 g, 21.41 mmol) in ethyl ether (100 mL) was added bromine (1.210 mL, 23.55 mmol) dropwise at RT and the mixture was allowed to stir for 14 h. Evaporation followed by purification by flash chromatography (silica gel, 0% to 10% ethyl acetate in hexanes) yielded the title compound (4.0 g, 85% yield) as a white solid: ¹H NMR (500 MHz, CDCl₃) δ 6.31 (s, 1H), 3.88 (s, 3H), 2.33 (s, 3H); HPLC retention time: 2.776 min, LCMS (ES): m/z 219, 221 [M+H]+.

Part B. Methyl 5-(4-chlorophenyl)-3-methylfuran-2-carboxylate

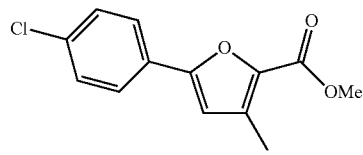 [SMILES: COC(=O)c1oc(-c2ccc(Cl)cc2)cc1C]

A flask containing a mixture of Part A compound (2.60 g, 11.87 mmol), 4-chlorophenylboronic acid (2.320 g, 14.84 mmol), and K$_2$CO$_3$ (3.28 g, 23.74 mmol) in DME (35 mL) was purged with argon and stirred at RT for 5 min. at which point Pd(PPh$_3$)$_4$ (0.343 g, 0.297 mmol) was added. The flask was purged with argon for 2 min and then heated to 90° C. for 9 h. The reaction mixture was filtered through a pad of CELITE® after cooled to RT. The organic layer was separated, dried over anhydrous Na$_2$SO$_4$, and concentrated. The residue was purified by flash chromatography (silica gel, 0% to 10% ethyl acetate in hexanes) to afford the title compound (2.40 g, 81% yield) as a white solid: $^1$H NMR (500 MHz, CDCl$_3$) δ 7.66 (d, J=8.8 Hz, 2H), 7.36 (d, J=8.8 Hz, 2H), 6.58 (s, 1H), 3.91 (s, 3H), 2.38 (s, 3 H); HPLC retention time (Method 1): 3.813 min.; LCMS (ES): m/z 251 [M+H]+.

Part C. 5-(4-Chlorophenyl)-3-methylfuran-2-carboxylic acid

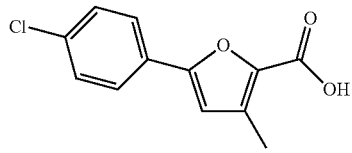 [SMILES: Cc1cc(-c2ccc(Cl)cc2)oc1C(=O)O]

Following the procedure described in Part C of Example 5, 700 mg of Part B compound, 123 mg of sodium hydroxide in EtOH (20 mL) and H$_2$O (1 mL) afforded the title compound (653 mg, 99% yield): $^1$H NMR (500 MHz, DMSO-d$_6$) δ 13.16 (br. s., 1H), 7.77 (s, 1H), 7.61 (d, J=8.2 Hz, 2H), 7.32 (d, J=8.8 Hz, 2H), 6.86 (s, 1H), 2.13 (s, 3H); HPLC retention time: 3.253 min; LCMS (ES): m/z 237 [M+H]+.

Part D. 3-(Bromomethyl)-5-(4-chlorophenyl)furan-2-carboxylic acid

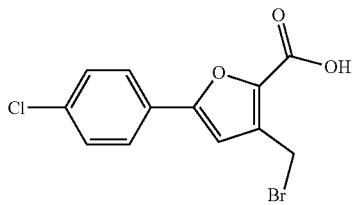 [SMILES: O=C(O)c1oc(-c2ccc(Cl)cc2)cc1CBr]

Using the procedure described in Part D of Example 1, 400 mg of Part C compound, 0.25 mL of HMDS, 300 mg of NBS and 14 mg of AIBN in 1.5 mL of CCl$_4$ afforded the title compound (400 mg, 75% yield): $^1$H NMR (500 MHz, DMSO-d$_6$) δ 7.82 (d, J 8.8 Hz, 2H), 7.55 (d, J=8.8 Hz, 2H), 7.31 (s, 1H), 4.82 (s, 2H); HPLC retention time: 3.223 min; LCMS (ES): m/z 317, 319 [M+H]+.

Part E. 2-(4-Chlorophenyl)-5-(4-(2-hydroxy-2-methylpropoxy)-3-methoxyphenyl)-4H-furo[3,2-c]pyrrol-6(5H)-one

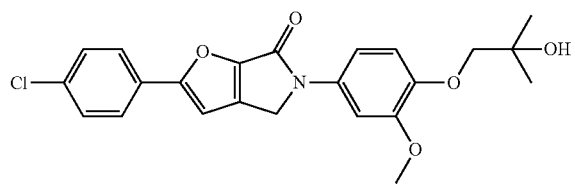

A solution of Part D product (40 mg, 0.127 mmol), EDC (48.6 mg, 0.254 mmol) and 1-(4-amino-2-methoxyphenoxy)-2-methylpropan-2-ol (26.8 mg, 0.127 mmol) in DMF (1.0 mL) was stirred at RT overnight. After K$_2$CO$_3$(35.0 mg, 0.254 mmol) was added, the reaction was stirred overnight. Then the mixture was diluted with EtOAc (~25 mL), washed with water and brine, dried over anhydrous Na$_2$SO$_4$, and concentrated. The resulting brown solution was purified by prep. HPLC to give 10 mg of the title compound as a white solid after lyophilization: $^1$H NMR (400 MHz, CDCl$_3$) δ7.72 (d, J=8.3 Hz, 2H), 7.60 (s, 1H), 7.42 (d, J=8.3 Hz, 2H), 6.94 (br. s., 2H), 6.80 (s, 1H), 4.66 (s, 2H), 3.91 (s, 3H), 3.83 (s, 2H), 1.34 (s, 6H); HPLC retention time: 2.918 min; LCMS (ES): m/z 428 [M+H]+.

Examples 55 and 56

These Examples were prepared following the method described in Example 1.

| Ex. No. | Structure | HPLC retention (min) | LCMS (ES): m/z [M + H]+ | 1H-NMR |
|---|---|---|---|---|
| 55 | 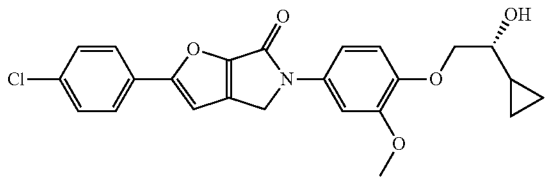 [SMILES: COc1cc(N2Cc3cc(-c4ccc(Cl)cc4)oc3C2=O)ccc1OC[C@H](O)C1CC1] | 3.770 | 440 | 1H NMR (500 MHz, chloroform-d) δ 7.71 (d, J = 8.2 Hz, 2 H), 7.60 (s, 1 H), 7.41 (d, J = 8.2 Hz, 2 H), 6.96 (s, 2 H), 6.79 (s, 1 H), 4.66 (s, 2 H), 4.18 (dd, J = 9.6, 2.5 Hz, 1 H), 3.98 (t, J = 9.1 Hz, 1 H), 3.86-3.94 (m, 3 H), 3.26-3.37 (m, 1 H), 2.23 (br. s., 1 H), 0.88-1.02 (m, 1 H), 0.60 (dd, J = 8.5, 4.1 Hz, 1 H), 0.54 (dd, J = 8.8, 4.4 Hz, 1 H), 0.45 (dd, J = 9.3, 4.9 Hz, 1 H), 0.25-0.34 (m, 1 H). |
| 56 | 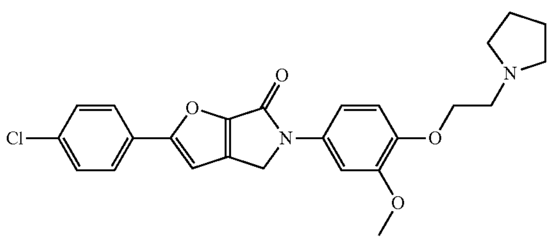 [SMILES: COc1cc(N2Cc3cc(-c4ccc(Cl)cc4)oc3C2=O)ccc1OCCN1CCCC1] | 2.853 | 453 | 1H NMR (500 MHz, methanol-d3) δ 7.83 (d, J = 8.8 Hz, 2 H), 7.62 (s, 1 H), 7.49 (d, J = 8.2 Hz, 2 H), 7.03-7.19 (m, 3 H), 4.81 (s, 2 H), 4.26-4.36 (m, 2 H), 3.89-3.98 (m, 3 H), 3.81 (br. s., 2 H), 3.59-3.70 (m, 2 H), 3.22 (br. s., 2 H), 2.22 (br. s., 2 H), 2.08 (br. s., 2 H). |

Example 57 to 70

Prodrugs were prepared from selected secondary and tertiary alcohols to improve solubility and exposure. Preparation of the Glycine ester and the Valine ester of the alcohols are exemplified below. Examples 59 to 70 were prepared in a similar manner to that described for Examples 57 or 58 using the appropriate alcohol and BOC Glycine or BOC Valine followed by HCl removal of the BOC group.

Example 57

1-(4-(2-(4-Chlorophenyl)-6-oxo-4H-thieno[2,3-c]pyrrol-5(6H)-yl)-2-methoxyphenoxy)-2-methylpropan-2-yl 2-aminoacetate, hydrochloric acid salt

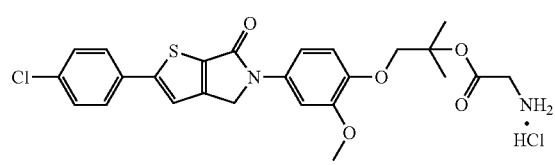 [SMILES: COc1cc(N2Cc3cc(-c4ccc(Cl)cc4)sc3C2=O)ccc1OCC(C)(C)OC(=O)CN ; Cl]

Part A. 1-(4-(2-(4-Chlorophenyl)-6-oxo-4H-thieno[2,3-c]pyrrol-5(6H)-yl)-2-methoxyphenoxy)-2-methylpropan-2-yl 2-(tert-butoxycarbonylamino)acetate

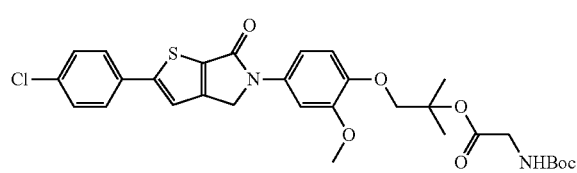 [SMILES: COc1cc(N2Cc3cc(-c4ccc(Cl)cc4)sc3C2=O)ccc1OCC(C)(C)OC(=O)CNC(=O)OC(C)(C)C]

To a refluxing suspension of Part F compound in Example 1 (1.33 g, 3.00 mmol), 4-(pyrrolidin-1-yl)pyridine (0.666 g, 4.49 mmol) and BOC-Gly-OH (1.575 g, 8.99 mmol) in CH2Cl2 (49.9 mL) was added DIC (1.400 mL, 8.99 mmol) dropwise over a period of 1 h. Reflux was continued for 3 h; whereupon the mixture was cooled to RT and hydrazine monohydrate (0.441 mL, 8.99 mmol) was added. After stirring for an additional 1H, the reaction mixture was cooled to 0° C. and filtered. The filtrate was washed with cold 1N HCl (3×75 mL) and cold 10% NaHCO3 (3×75 mL) prior to drying over anhydrous Na2SO4 and concentrating under vacuum. The residue was purified by flash chromatography (silica gel, CH2Cl2:EtOAc, 100:0 to 0:100) to afford 1.10 g (61%) of the title compound as a yellow solid: HPLC retention time: 4.133 min., LCMS (ES): m/z 601 [M+H]+.

Part B. 1-(4-(2-(4-Chlorophenyl)-6-oxo-4H-thieno[2,3-c]pyrrol-5(6H)-yl)-2-methoxyphenoxy)-2-methylpropan-2-yl 2-aminoacetate, hydrochloric acid salt

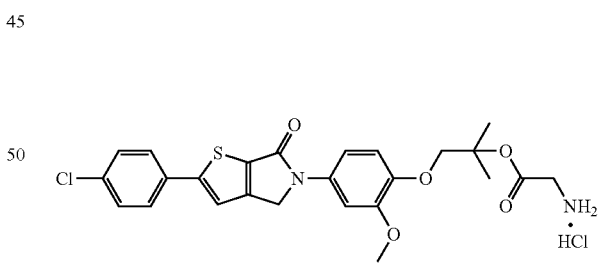

To a 0° C. solution of Part A compound (1.100 g, 1.830 mmol) in 1,4-dioxane (18.4 mL) was added 4 M HCl in 1,4-dioxane (22.87 mL, 91 mmol) dropwise over 20 min. Stirring was continued at RT for 16 h; whereupon the solvent was removed until about ¼ reaction volume left. Ether was added and the solid was filtered, washed well with ether (2×) and lyophilized to afford 974 mg (98% yield) of the title compound as a yellow solid: 1H NMR (500 MHz, DMSO) δ 8.18 (3H, br. s.), 7.81 (2H, d, J=8.25 Hz), 7.76 (1H, s), 7.55 (3H, d, J=8.80 Hz), 7.24 (1H, dd, J=8.80, 2.75 Hz), 7.03 (1H, d, J=8.80 Hz), 4.99 (2H, s), 4.14 (2H, s), 3.81 (3H, s), 3.73

(2H, s), 1.56 (6H, s). HPLC retention time: 3.216 min.; LCMS (ES): m/z 501 [M+H]⁺.

Example 58

(S)-1-(4-(2-(4-Chlorophenyl)-6-oxo-4H-thieno[2,3-c]pyrrol-5(6H)-yl)-2-methoxyphenoxy)-3-(ethylsulfonyl)propan-2-yl 2-aminoacetate, hydrochloric acid salt

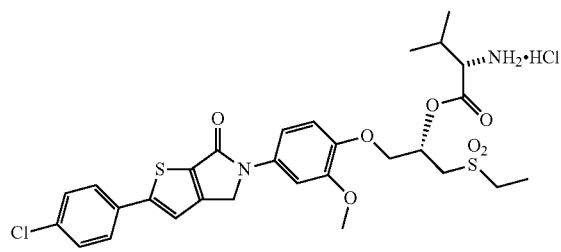

Part A. (S)-((S)-1-(4-(2-(4-Chlorophenyl)-6-oxo-4H-thieno[2,3-c]pyrrol-5(6H)-yl)-2-methoxyphenoxy)-3-(ethylsulfonyl)propan-2-yl) 2-(tert-butoxycarbonylamino)-3-methylbutanoate To a suspension of (S)-2-(4-chlorophenyl)-5-(4-(3-(ethylsulfonyl)-2-hydroxypropoxy)-3-methoxyphenyl)-4H-thieno[2,3-c]pyrrol-6(5H)-one (46.0 mg, 0.088 mmol), DMAP (5.47 mg, 0.045 mmol) and BOC-Val-OH (22.96 mg, 0.106 mmol) in CH₂Cl₂ (0.401 mL) at RT was added DIC (0.022 mL, 0.141 mmol) dropwise over a period of 1 h. After stirring for an additional 2H, the reaction mixture was filtered and the filtrate was washed with cold 1N HCl (3×10 mL) and cold 10% NaHCO₃ (3×10 mL) prior to drying over anhydrous Na₂SO₄ and concentrating under vacuum. The residue was purified by flash chromatography (silica gel, hexanes:EtOAc, 100:0 to 0:100) to afford 50.4 mg (79% yield) of the title compound as a yellow solid: HPLC retention time: 4.153 min., LCMS (ES): m/z 721 [M+H]⁺.

Part B. (S)-1-(4-(2-(4-Chlorophenyl)-6-oxo-4H-thieno[2,3-c]pyrrol-5(6H)-yl)-2-methoxyphenoxy)-3-(ethylsulfonyl)propan-2-yl 2-aminoacetate, hydrochloric acid salt

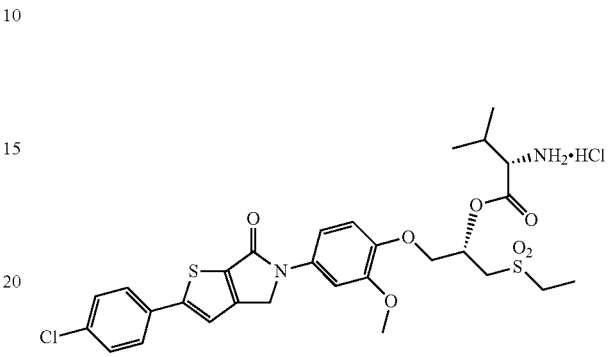

To a 0° C. solution of Part A compound (48.0 mg, 0.067 mmol) in 1,4-dioxane (0.67 mL) was added 4 M HCl in 1,4-dioxane (0.832 mL, 3.33 mmol) dropwise over 20 min. Stirring was continued at RT for 22 h; whereupon the solvent

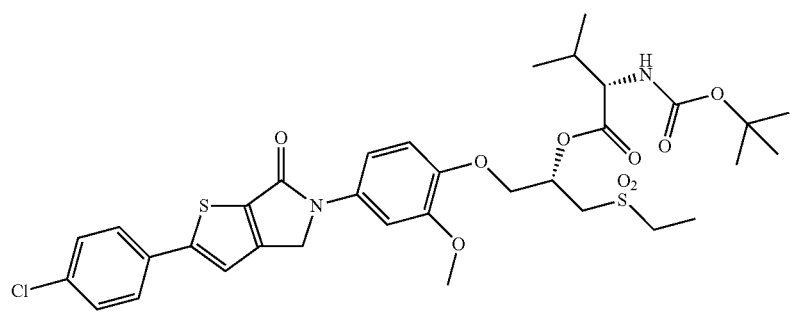 [SMILES: CCS(=O)(=O)C[C@H](COc1ccc(N2Cc3cc(-c4ccc(Cl)cc4)sc3C2=O)cc1OC)OC(=O)[C@@H](NC(=O)OC(C)(C)C)C(C)C]

was removed until about ¼ reaction volume left. Ether was added and the solid was filtered, washed well with ether (2×) and lyophilized to afford 36.4 mg (83% yield) of the title compound as a light yellow solid: ¹H NMR (500 MHz, DMSO) δ 8.36 (3H, br. s.), 7.81 (2H, d, J=8.80 Hz), 7.76 (1H, s), 7.51-7.60 (3H, m), 7.25 (1H, dd, J=8.80, 2.20 Hz), 7.05 (1H, d, J=8.80 Hz), 5.69 (1H, ddd, J=10.17, 5.50, 5.22 Hz), 5.00 (2H, s), 4.12-4.30 (2H, m), 3.73-3.94 (5H, m), 3.63-3.71 (2H, m), 3.12-3.27 (2H, m, J=13.78, 7.15, 6.95, 6.95 Hz), 1.24 (3H, t, J=7.42 Hz). HPLC retention time: 3.055 min.; LCMS (ES): m/z 579 [M+H]⁺.

| | | Prodrug Esters | | | |
|---|---|---|---|---|---|
| Ex. No. | Prodrug of Ex. No. | Structure | HPLC retention (min) | LCMS (ES): m/z [M + H]+ | 1H-NMR |
| 57 | 1 | | 3.216 | 501 | 1H NMR (500 MHz, DMSO-d6) δ 8.18 (3 H, br. s.), 7.81 (2 H, d, J = 8.25 Hz), 7.76 (1 H, s), 7.55 (3 H, d, J = 8.80 Hz), 7.24 (1 H, dd, J = 8.80, 2.75 Hz), 7.03 (1 H, d, J = 8.80 Hz), 4.99 (2 H, s), 4.14 (2 H, s), 3.81 (3 H, s), 3.73 (2 H, s), 1.56 (6 H, s). |
| 58 | 16 | | 3.15 | 621 | 1H NMR (400 MHz, DMSO-d6) δ 8.20 (3 H, br. s.), 7.76 (2 H, d, J = 8.35 Hz), 7.71 (1 H, s), 7.45-7.53 (3 H, m), 7.19 (1 H, dd, J = 8.79, 2.20 Hz), 7.00 (1 H, d, J = 8.79 Hz), 5.57-5.68 (1 H, m), 4.94 (2 H, s), 4.05-4.26 (2 H, m), 3.83-3.88 (1 H, m), 3.76 (3 H, s), 3.55-3.73 (3 H, m), 3.10-3.21 (2 H, m), 1.18 (3 H, t, J = 7.47 Hz), 0.92 (6 H, dd, J = 16.26, 7.03 Hz). |
| 59 | 2 | | 3.405 | 555 | 1H NMR (500 MHz, CD2Cl2) δ 7.72 (2 H, d, J = 8.80 Hz), 7.56 (1 H, d, J = 2.20 Hz), 7.54 (1 H, s), 7.46 (2 H, d, J = 8.25 Hz), 7.14 (1 H, dd, J = 8.52, 2.47 Hz), 7.03 (1 H, d, J = 8.80 Hz), 4.91 (2 H, s), 4.67-4.74 (1 H, m), 4.26-4.35 (2 H, m), 3.93 (1 H, d, J = 4.40 Hz), 3.87 (3 H, s), 2.19-2.48 (1 H, m), 1.21-1.40 (1 H, m), 1.13 (6 H, dd, J = 9.90, 7.15 Hz), 0.61-0.75 (2 H, m), 0.45-0.57 (2 H, m). |
| 60 | 16 | | 3.055 | 579 | 1H NMR (500 MHz, DMSO-d6) δ 8.36 (3 H, br. s.), 7.81 (2 H, d, J = 8.80 Hz), 7.76 (1 H, s), 7.51-7.60 (3 H, m), 7.25 (1 H, dd, J = 8.80, 2.20 Hz), 7.05 (1 H, d, J = 8.80 Hz), 5.69 (1 H, ddd, J = 10.17, 5.50, 5.22 Hz), 5.00 (2 H, s), 4.12-4.30 (2 H, m), 3.73-3.94 (5 H, m), 3.63-3.71 (2 H, m), 3.12-3.27 (2 H, m, J = 13.78, 7.15, 6.95, 6.95, 6.95 Hz), 1.24 (3 H, t, J = 7.42 Hz). |
| 61 | 17 | | 3.066 | 579 | 1H NMR (500 MHz, DMSO-d6) δ 8.36 (3 H, br. s.), 7.81 (2 H, d, J = 8.80 Hz), 7.76 (1 H, s), 7.51-7.59 (3 H, m), 7.25 (1 H, dd, J = 8.80, 2.20 Hz), 7.05 (1 H, d, J = 8.80 Hz), 5.69 (1 H, ddd, J = 10.31, 5.09, 4.95 Hz), 4.99 (2 H, s), 4.12-4.31 (2 H, m), 3.76-3.90 (5 H, m), 3.67 (2 H, d, J = 6.60 Hz), 3.11-3.25 (2 H, m), 1.24 (3 H, t, J = 7.42 Hz). |
| 62 | 7 | | 3.368 | 549 | 1H NMR (400 MHz, DMSO-d6) δ 7.81 (2 H, d, J = 8.35 Hz), 7.76 (1 H, s), 7.50-7.61 (3 H, m), 7.24 (1 H, dd, J = 9.01, 2.42 Hz), 7.05 (1 H, d, J = 8.79 Hz), 4.99 (2 H, s), 4.31 (2 H, s), 3.81 (3 H, s), 3.70 (2 H, s), 2.94-3.26 (4 H, m). |

| Ex. No. | Prodrug of Ex. No. | Structure | HPLC retention (min) | LCMS (ES): m/z [M + H]$^+$ | $^1$H-NMR |
|---|---|---|---|---|---|
| 63 | 26 | 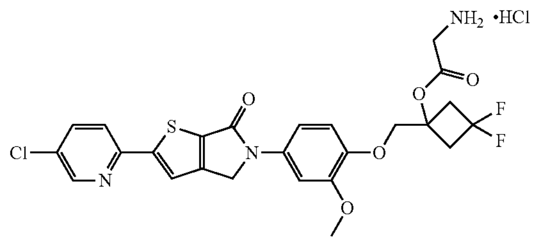 [SMILES: Cl ; COc1cc(N2Cc3cc(-c4ccc(Cl)cn4)sc3C2=O)ccc1OCC1(OC(=O)CN)CC(F)(F)C1] | 3.126 | 550 | $^1$H NMR (500 MHz, CDCl$_3$ (w/ drop DMSO for solubility) δ 8.60 (1 H, d, J = 2.20 Hz), 7.97-8.04 (1 H, m), 7.92-7.97 (1 H, m), 7.86 (1 H, s), 7.62 (1 H, d, J = 2.20 Hz), 7.22 (1 H, dd, J = 8.52, 2.47 Hz), 7.08 (1 H, d, J = 8.80 Hz), 4.97 (2 H, s), 4.44 (2 H, s), 3.91 (3 H, s), 3.86 (2 H, s), 3.16-3.27 (2 H, m), 3.03-3.18 (2 H, m). |
| 64 | 24 | 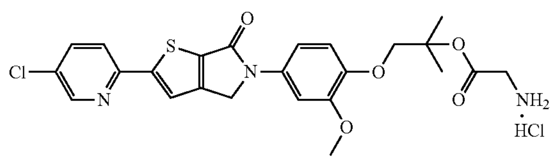 [SMILES: COc1cc(N2Cc3cc(-c4ccc(Cl)cn4)sc3C2=O)ccc1OCC(C)(C)OC(=O)CN ; Cl] | 2.938 | 502 | $^1$H NMR (500 MHz, DMSO-d$_6$) δ 8.60 (1 H, d, J = 2.20 Hz), 8.06-8.17 (4 H, m), 8.02 (1 H, dd, J = 8.25, 2.20 Hz), 7.97 (1 H, s), 7.48 (1 H, d, J = 2.20 Hz), 7.19 (1 H, dd, J = 8.80, 2.20 Hz), 6.98 (1 H, d, J = 8.80 Hz), 4.94 (2 H, s), 4.08 (2 H, s), 3.75 (3 H, s), 3.67 (2 H, s), 1.51 (6 H, s). |
| 65 | 29 | 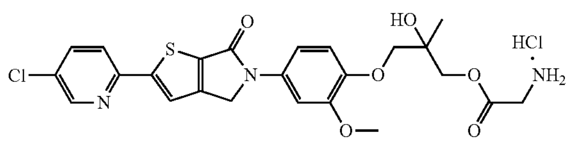 [SMILES: COc1cc(N2Cc3cc(-c4ccc(Cl)cn4)sc3C2=O)ccc1OCC(C)(O)COC(=O)CN ; Cl] | 2.830 | 518 | $^1$H NMR (500 MHz, DMSO-d$_6$) δ 8.66 (d, J = 1.9 Hz, 1 H), 8.37 (br. s., 3 H), 8.13-8.20 (m, 1 H), 8.08 (dd, J = 8.5, 2.5 Hz, 1 H), 8.03 (s, 1 H), 7.54 (d, J = 2.5 Hz, 1 H), 7.25 (dd, J = 8.5, 2.5 Hz, 1 H), 7.04 (d, J = 8.8 Hz, 1 H), 5.12 (s, 1 H), 5.00 (s, 2 H), 4.12-4.26 (m, 2 H), 3.92 (d, J = 9.4 Hz, 1 H), 3.85 (s, 2 H), 3.79-3.84 (m, 4 H), 1.26 (s, 3 H). |
| 66 | 31 | 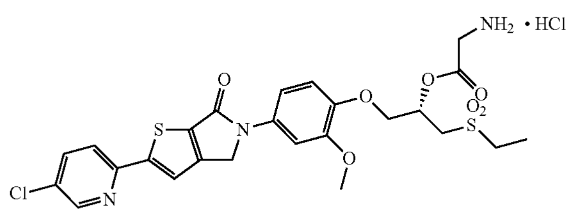 | 2.763 | 580 | $^1$H NMR (500 MHz, DMSO-d$_6$) δ 8.65 (1 H, d, J = 2.20 Hz), 8.35 (3 H, br. s.), 8.15 (1 H, d, J = 8.80 Hz), 8.07 (1 H, dd, J = 8.80, 2.20 Hz), 8.03 (1 H, s), 7.57 (1 H, d, J = 2.20 Hz), 7.22-7.30 (1 H, m), 7.06 (1 H, d, J = 8.80 Hz), 5.62-5.73 (1 H, m), 5.01 (2 H, s), 4.11-4.29 (2 H, m), 3.75-3.91 (5 H, m), 3.65-3.70 (2 H, m), 3.19 (2 H, ddd, J = 13.47, 7.15, 6.87 Hz), 1.24 (3 H, t, J = 7.42 Hz). |
| 67 | 41 | 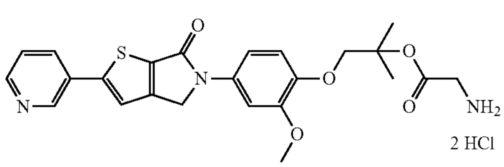 [SMILES: COc1cc(N2Cc3cc(-c4cccnc4)sc3C2=O)ccc1OCC(C)(C)OC(=O)CN] | 2.042 | 468 | $^1$H NMR (400 MHz, DMSO-d$_6$) δ 9.24 (1 H, br. s.), 8.77 (1 H, br. s.), 8.44-8.56 (2 H, m), 8.38 (3 H, br. s.), 8.01 (1 H, br. s.), 7.79 (1 H, br. s.), 7.63 (1 H, d, J = 2.20 Hz), 7.33 (1 H, dd, J = 8.79, 2.20 Hz), 7.12 (1 H, d, J = 8.79 Hz), 5.11 (2 H, s), 4.22 (2 H, s), 3.89 (3 H, s), 3.78 (2 H, d, J = 4.95 Hz), 1.64 (6 H, s). |
| 68 | 33 | 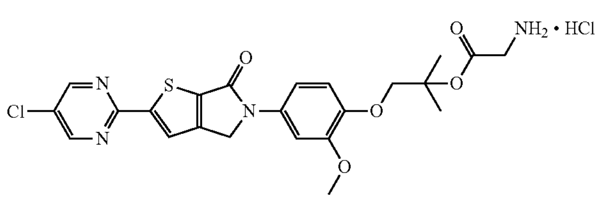 | 2.896 | 503 | $^1$H NMR (500 MHz, DMSO-d$_6$) δ 8.98 (2 H, s), 8.04 (4 H, s), 7.49 (1 H, d, J = 2.75 Hz), 7.22 (1 H, dd, J = 8.80, 2.20 Hz), 7.02 (1 H, d, J = 8.80 Hz), 4.98 (2 H, s), 4.11 (2 H, s), 3.78 (3 H, s), 3.69 (2 H, s), 1.53 (6 H, s). |

Prodrug Esters

| Ex. No. | Prodrug of Ex. No. | Structure | HPLC retention (min) | LCMS (ES): m/z [M + H]+ | 1H-NMR |
|---|---|---|---|---|---|
| 69 | 34 | 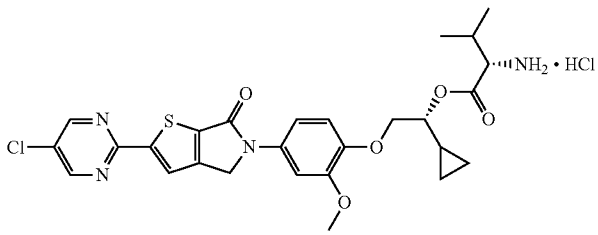 | 3.150 | 557 | 1H NMR (500 MHz, DMSO-d6) δ 9.01 (2 H, s), 8.07 (1 H, s), 7.52 (1 H, d, J = 2.20 Hz), 7.26 (1 H, dd, J = 8.80, 2.20 Hz), 7.06 (1 H, d, J = 8.80 Hz), 5.01 (2 H, s), 4.58-4.69 (1 H, m), 4.21 (2 H, d, J = 4.40 Hz), 3.95 (1 H, d, J = 3.85 Hz), 3.79 (3 H, s), 2.20 (1 H, br. s.), 1.23 (1 H, d, 8.25 Hz), 1.04 (3 H, d, J = 7.15 Hz), 1.00 (3 H, d, J = 7.15 Hz), 0.49-0.64 (3 H, m), 0.41 (1 H, br. s). |
| 70 | 35 | 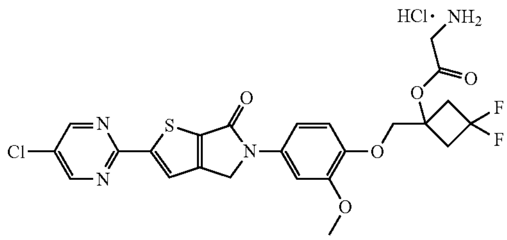 [SMILES: Cl ; COc1cc(N2Cc3cc(-c4ncc(Cl)cn4)sc3C2=O)ccc1OCC1(OC(=O)CN)CC(F)(F)C1] | 3.121 | 551 | 1H NMR (500 MHz, DMSO-d6) δ 9.01 (s, 2 H) 8.31 (br. s., 2 H) 8.07 (s, 1 H) 7.55 (d, J = 2.75 Hz, 1 H) 7.27 (dd, J = 8.52, 2.47 Hz, 1 H) 7.07 (d, J = 8.80 Hz, 1 H) 5.03 (s, 2 H) 4.34 (s, 2 H) 3.82 (s, 2 H) 3.33 (s, 3 H) 3.13-3.25 (m, 2 H) 2.99-3.13 (m, 1 H). |

Biological Evaluation

Radioligand Binding Assay for Assessment of MCHR1 Activity

Membranes from stably transfected HEK-293 cells expressing a mutated (E4Q, A5T) hMCHR1 receptor were prepared by dounce homogenization and differential centrifugation. Binding experiments were carried out with 0.5-1.0 ug of membrane protein incubated in a total of 0.2 ml in 25 mM HEPES (pH 7.4) with 10 mM MgCl$_2$, 2 mM EGTA, and 0.1% BSA (Binding Buffer) for 90 min. For competition binding assays, reactions were carried out in the presence of with 0.06-0.1 nM [Phe$^{13}$, [$^{125}$I]Tyr$^{19}$]-MCH and increasing concentrations of unlabeled test molecules. Reactions were terminated by rapid vacuum filtration over 96 well-GFC UNI-FILTER® plates pre-coated with 0.075 ml binding buffer containing 1% BSA, and washed 3 times with 0.4 ml of Phospho-buffered Saline (pH 7.4) containing 0.01% TX-100. Filters were dried, 0.05 ml microscint 20 was added to each well and radioactivity was subsequently quantified by scintillation counting on a TOPCOUNT® microplate scintillation counter (Packard). Inhibitory constants were determined by nonlinear least squares analysis using a four parameter logistic equation.

| Ex. No. | MCHR1 Human Binding (Ki, nM) |
|---|---|
| 1 | 1.9 |
| 2 | 2.5 |
| 3 | 0.2 |
| 6 | 30.0 |
| 10 | 0.3 |
| 15 | 0.6 |
| 21 | 0.2 |
| 27 | 2.5 |
| 33 | 17.0 |
| 39 | 33.6 |
| 41 | 800 |
| 43 | 1293 |
| 44 | 21.6 |
| 49 | 107 |
| 52 | 68 |
| 53 | 248 |
| 54 | 13.3 |
| 68 | 17.6 |

Assessment of In Vivo MCHR Activity

Male SPRAGUE DAWLEY® (CD, Charles River Breeding Laboratory) rats weighing approximately 240 grams were place in individual plastic cages with ALPHADRI® bedding. The room was maintained at 72° F. and 50% humidity, and a 12/12 light dark cycle with lights out at 1600 hours. The rats were conditioned for 5 days prior to the start of the study to having a choice of foods. A normal chow (HARLAN TEKLAD®, 2018) that contains 18% protein, 5% fat and 73% carbohydrate and a high fat high sugar diet (Research Diets (D2327)) that contains 20% protein, 40% fat and 40% carbohydrate where the carbohydrate is entirely sucrose and the fat is soybean and coconut oil. Studies have revealed that rats exhibit a high preference for the high coconut oil. Studies have revealed that rats exhibit a high preference for the high fat/high sucrose dies (80% preference). Body weight and consumption of both kinds of food as well as water intake were measured daily. Water was available ad lib throughout the study. Food consumption is presented as daily caloric consumption which is the sum of grams of chow multiplied by the Kcal per gram (3.5) plus grams of high fat high sugar multiplied by Kcal per gram (4.59).

Baseline body weight was measured prior to drug treatment on day 0 of the study. Baseline food consumption was the average of the 3 days prior to the first drug treatment. Drug was administered daily p.o. at 2.0 ml/kg at 1500 hours beginning on day 0 and continuing daily through day 4 as a suspension in 0.5% methyl cellulose, 0.1% Tween 80 in water at 3.0, 10 and 30 mg/kg p.o. All data were evaluated using ANOVA and Fishers PLSD statistics.

| Biological Data | | |
|---|---|---|
| Example | Dose (mg/kg) | Weight Reduction versus Vehicle |
| Example 1 (Dosed as prodrug of Example 57) | 30 | 3.9% |
| Example 33 (Dosed as prodrug of Example 68) | 30 | 4.8% |
| Example 31 (Dosed as prodrug of Example 66) | 30 | 3.2% |

The above data shows that the compounds of the invention tested were active in reducing weight of the animals tested.

It should be understood that while this application has been described herein in terms of specific embodiments set forth in detail, such embodiments are presented by way of illustration of the general principles of the application, and the application is not necessarily limited thereto. Certain modifications and variations in any given material, process step or chemical formula will be readily apparent to those skilled in the art without departing from the true spirit and scope of the present application, and all such modifications and variations should be considered within the scope of the claims that follow.

What is claimed is:

1. A compound of Formula I

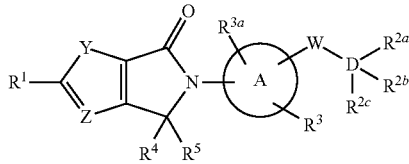

wherein:
Y is O or S;
Z is CH or N;

is selected from the group consisting of phenyl and monocyclic heteroaryl;
$R^1$ is selected from the group consisting of substituted or unsubstituted phenyl or substituted and unsubstituted monocyclic heteroaryl;
D is selected from the group consisting of a direct bond, substituted or unsubstituted $C_1$-$C_4$ alkyl, substituted or unsubstituted $C_3$-$C_7$ cycloalkyl, substituted or unsubstituted $C_3$-$C_7$-cycloalkyl-$C_1$-$C_4$-alkyl, a 4- to 6-membered cyclic amine and an 8-membered bicyclic amine;
W is selected from the group consisting of —O— and —N($R^6$)—; or W is a direct bond provided that

is linked to the nitrogen of a cyclic or bicyclic amine;
$R^{2a}$, $R^{2b}$ and $R^{2c}$ are the same or different and are independently selected from the group consisting of hydrogen, hydroxyl, substituted or unsubstituted $C_1$-$C_4$ alkoxy, substituted or unsubstituted $C_1$-$C_4$ alkyl, polyfluoro-$C_1$-$C_4$-alkyl, substituted or unsubstituted $C_3$-$C_7$ cycloalkyl, substituted or unsubstituted $C_3$-$C_7$ cycloalkoxy, —CN, $NR^{11}R^{11a}$, —$SO_2R^{10}$, —$CO_2R^{10}$, heterocyclyl, halo, hydroxy-$C_1$-$C_4$-alkyl, a substituted or unsubstituted 4- to 6-membered cyclic amine wherein said cyclic amine is optionally substituted with —OH, carbonylamino, alkoxycarbonylamino, or optionally at least one of $R^{2a}$, $R^{2b}$ and $R^{2c}$ is a prodrug moiety selected from an amino acid ester or a phosphoric acid ester wherein said amino acid has the formula

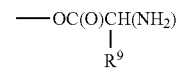

wherein $R^9$ is H or $C_1$-$C_4$ alkyl;
provided that when D is a direct bond, $R^{2a}$, $R^{2b}$ and $R^{2c}$ are the same or different and are independently selected from H, $C_1$-$C_4$ alkyl and $C_3$-$C_7$ cycloalkoxy;
or any two of $R^{2a}$, $R^{2b}$ or $R^{2c}$ may be taken together to form a ring; or
where $R^{2a}$ is OH, $R^{2b}$ and $R^{2c}$ can optionally be taken together with a carbon to which they are attached to form a $C_3$ to $C_7$ cycloalkyl ring which may be optionally substituted with one or two halogen atoms, or $R^{2b}$ and $R^{2c}$ optionally can be taken together with the carbon to which they are attached to form a 6-membered heterocycle which is 1,1-dioxido-tetrahydro-2H-thiopyran;
$R^3$ and $R^{3a}$ are the same or different and are independently selected from the group consisting of hydrogen, hydroxyl, substituted or unsubstituted $C_1$-$C_4$ alkoxy, halo, CN, substituted or unsubstituted $C_1$-$C_4$ alkyl, polyfluoro-$C_1$-$C_4$-alkyl, substituted or unsubstituted $C_3$-$C_7$ cycloalkyl, substituted or unsubstituted $C_3$-$C_7$ cycloalkoxy, amino, alkylamino, dialkylamino, and aminoalkyl, or $R^3$ and/or $R^{3a}$ are absent, or $R^3$ or $R^{3a}$ and D may optionally be taken together with the atoms to which they are attached to form a 5- to 7-membered ring;
$R^4$ and $R^5$ are the same or different and are independently selected from the group consisting of hydrogen and substituted or unsubstituted $C_3$-$C_7$ alkyl;
$R^6$ is selected from the group consisting of hydrogen, substituted or unsubstituted $C_1$-$C_4$ alkyl and substituted or unsubstituted $C_3$-$C_7$ cycloalkyl;
$R^{10}$ is independently selected from the group consisting of substituted or unsubstituted $C_1$-$C_4$ alkyl and substituted or unsubstituted $C_3$-$C_7$ cycloalkyl;
$R^{11}$ and $R^{11a}$ are the same or different and are independently selected from the group consisting of hydrogen, substituted or unsubstituted $C_1$-$C_4$ alkyl, hydroxy-$C_1$-$C_4$-alkyl, hydroxy-$C_1$-$C_4$-alkyl-$C_3$-$C_7$-cycloalkyl, substituted or unsubstituted heterocyclo-$C_1$-$C_4$-alkyl, acyl, $C_1$-$C_4$ alkoxycarbonyl, carboxy-$C_1$-$C_4$-alkyl, substituted or unsubstituted $C_3$-$C_7$ cycloalkyl, and substituted or unsubstituted $C_3$-$C_7$ cycloalkyl-$C_1$-$C_4$-alkyl, where the $R^{11}$ and $R^{11a}$ groups and the N atom to which they are attached may optionally form a 5- to 7-membered ring; and a pharmaceutically acceptable salt or a stereoisomer or a prodrug ester thereof.

2. The compound according to claim 1 wherein $R^1$ is substituted or unsubstituted phenyl, substituted or unsubstituted monocyclic heteroaryl which is

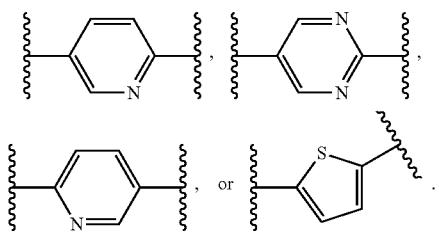

3. The compound according to claim 1 wherein Y is S and Z is CH, or Y is S and Z is N, or Y is O and Z is N, or Y is O and Z is CH.

4. The compound according to claim 1 wherein

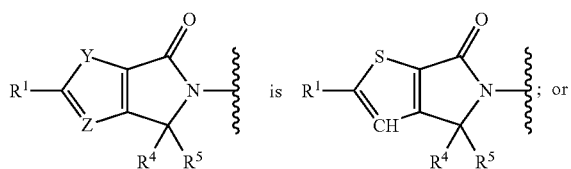

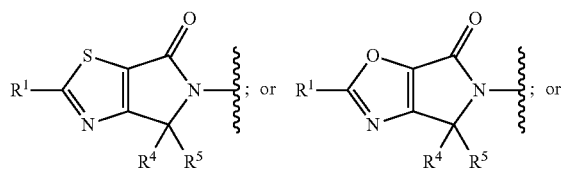

is phenylene or a heteroaryl which is

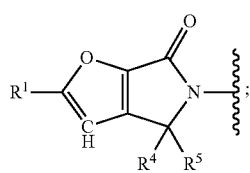

wherein $R^3$ is $C_1$-$C_4$ alkoxy, H, halo or $C_1$-$C_4$ alkyl and $R^{3a}$ is H; or wherein W is O or a bond provided that where W is a bond

is linked to the nitrogen of a cyclic or bicyclic amine;

wherein D is a bond or $C_1$-$C_4$ alkylene which may optionally be substituted with cycloalkyl, $C_1$-$C_4$ alkyl or other substituents for alkyl or a cyclic or bicyclic amine;

wherein $R^{2a}$ is OH, heterocyclyl, or $C_3$-$C_7$ cycloalkyl; or wherein $R^{2b}$ and $R^{2c}$ are each hydrogen, or any of the $R^{2a}$ groups;

wherein $R^1$ is

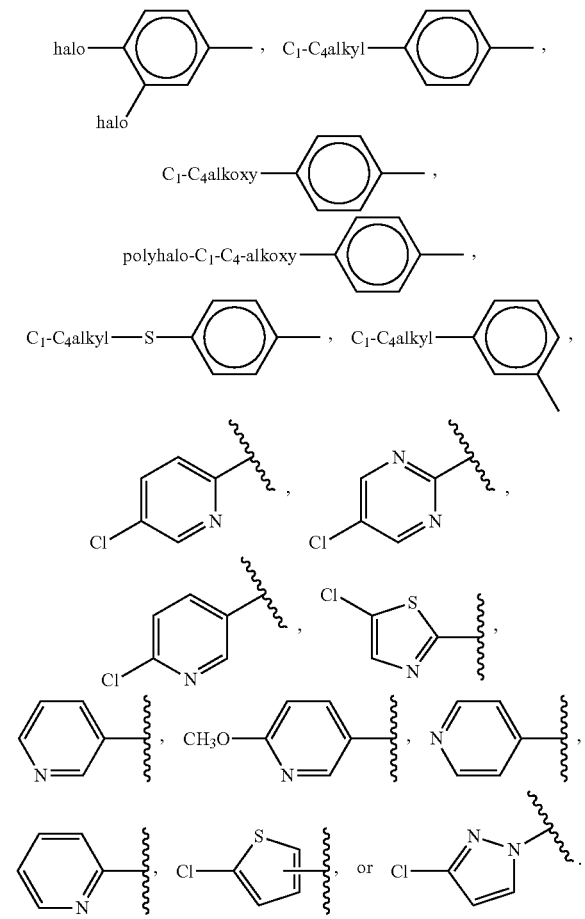

5. The compounds according to claim 1 wherein $R^1$ is

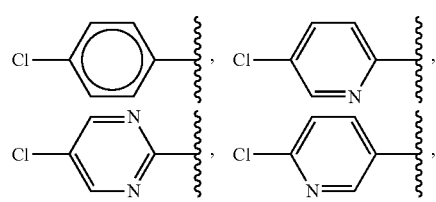

-continued

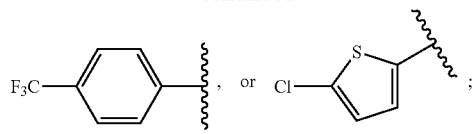

Y is —S— and Z is —CH—; or Y is —O— and Z is —CH—;

$R^4$ and $R^5$ are each H;

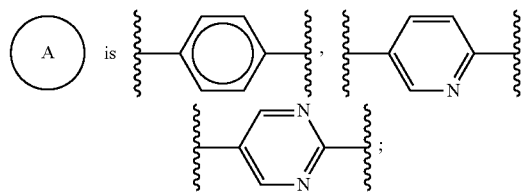

$R^{3a}$ is H, $C_1$-$C_4$ alkoxy which is $CH_3O$ or $C_1$-$C_4$ alkyl which is $CH_3$;

$R^3$ is H or any of the $R^{3a}$ groups set out above;

W is O;

D is $C_1$-$C_4$ alkylene which is

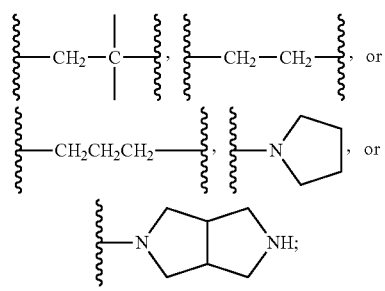

$R^{2a}$ is H, OH, heterocyclo which is

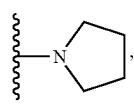

$C_1$-$C_4$ alkylamino which is —$NHCH_3$, $C_3$-$C_7$ cycloalkyl which is

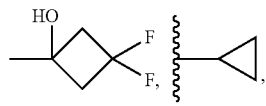

$SO_2R^{10}$ wherein $R^{10}$ is $C_1$-$C_4$ alkyl which is $CH_3$ or $C_2H_5$,

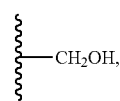

$C_1$-$C_4$ dialkylamino which is

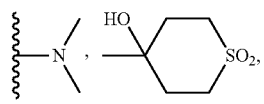

or $CF_3$;

$R^{2b}$ and $R^{2c}$ are independently selected from H, OH, $C_1$-$C_4$ alkyl which is $CH_3$, $CF_3$, $SO_2R^{10}$ where $R^{10}$ is $C_1$-$C_4$ alkyl which is $CH_3$ or $C_2H_5$;

or any of the $R^{2a}$ groups set out above;

or an HCl salt thereof or a TFA salt thereof;

or an amino acid ester prodrug thereof wherein the amino acid has the structure

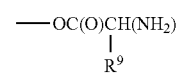

or the HCl salt thereof where $R^9$ is H or i-$C_3C_7$.

6. The compound according to claim 1 wherein

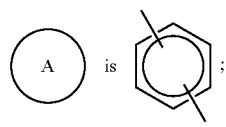

wherein W is O or a bond, provided that where W is a bond

is linked to the nitrogen of a cyclic or bicyclic amine, and D is $CH_2$, $CH_2CH_2$, $CH_2CH_2CH_2$,

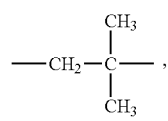

or a bond; or wherein $R^{2a}$ is

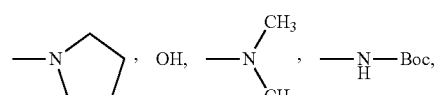

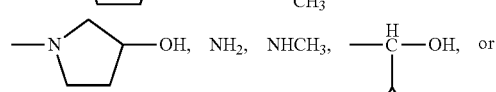

or
wherein R¹ is
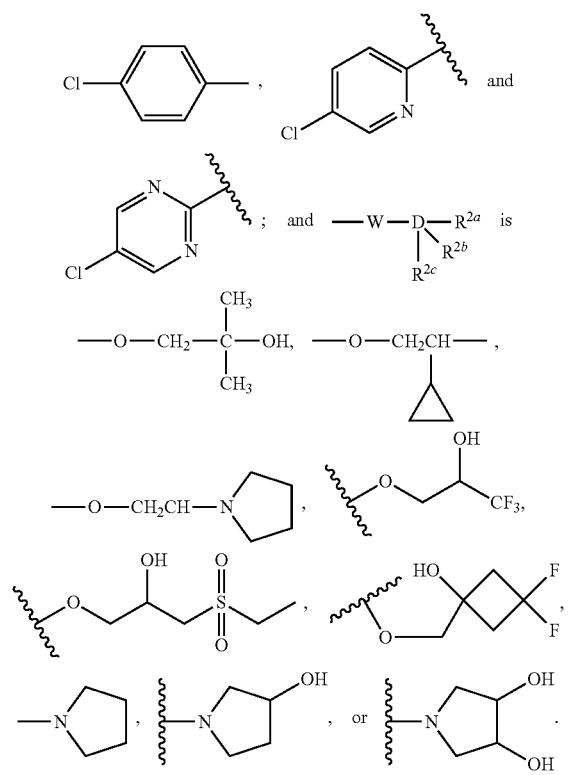
7. The compound according to claim 3 wherein $R^{2a}$ is OH or heterocyclo which is
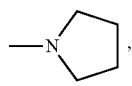
or cycloalkyl which is
or
R¹ is aryl which is
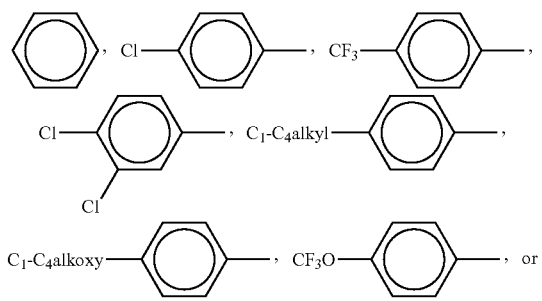
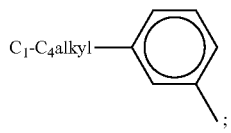
or R¹ is heteroaryl which is
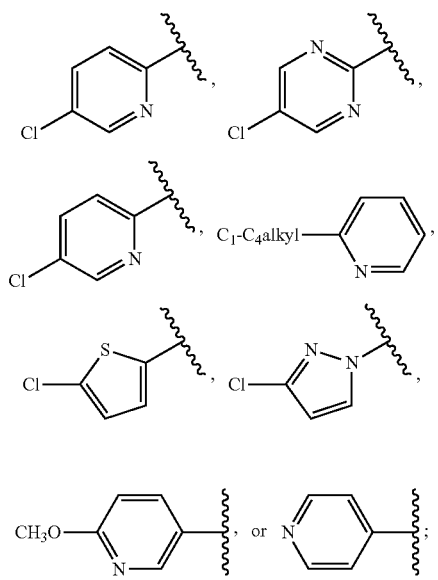
$R^3$ is H, lower alkyl, which is $CH_3$ or $C_1$-$C_4$ alkoxy which is $OCH_3$; or
$R^{3a}$ is H; or
$R^4$ and $R^5$ are each H; or
D is alkylene which is $CH_2$, $CH_2CH_2$, $CH_2CH_2CH_2$,
—CH₂—C(CH₃)₂—,
or a bond; or

| 127 | 128 |
|---|---|
| $R^{2a}$ is heterocyclo which is | $NH_2$, or $NHCH_3$, $C_1$-$C_4$ alkyl which is |
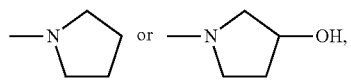 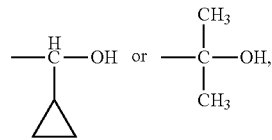
—$NR^{11}R^{11a}$ which is
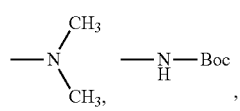
or OH; or
$R^{2b}$ and $R^{2c}$ are independently hydrogen, $CH_3$, OH, $SO_2CH_3$, $SO_2$, $C_2H_5$, $CH_2OH$, or F; or
W is O.
8. The compound according to claim 1, wherein the compound is selected from the group consisting of
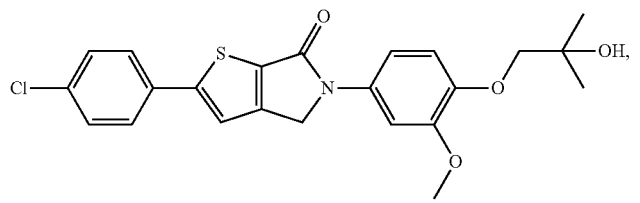
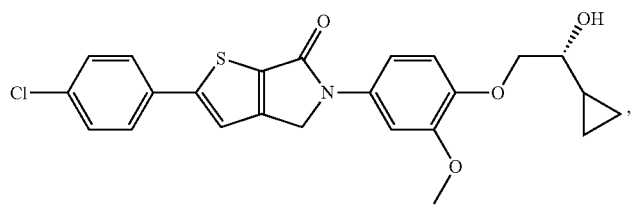
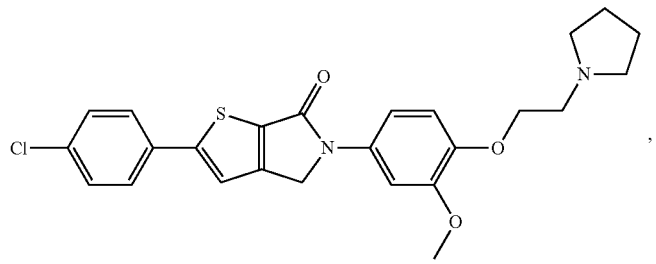
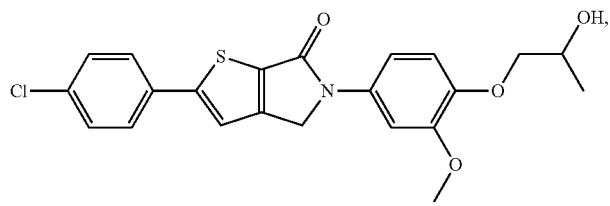
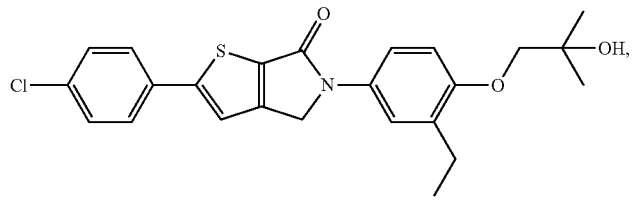
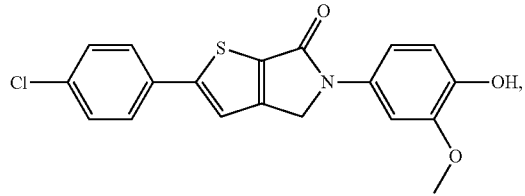

-continued
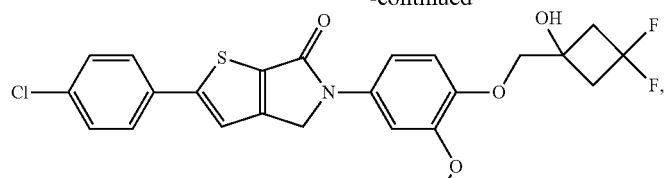
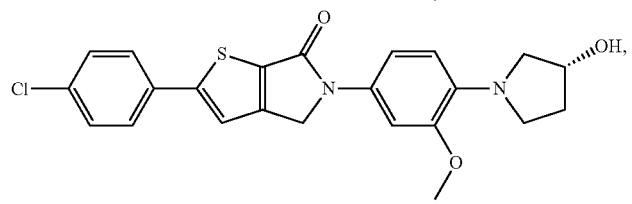
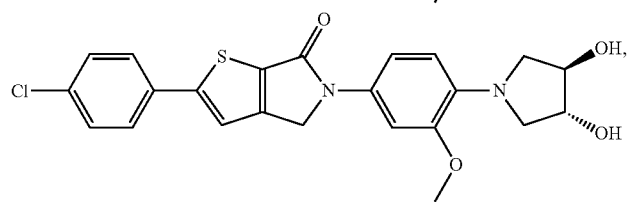
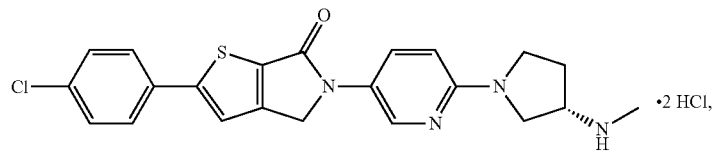
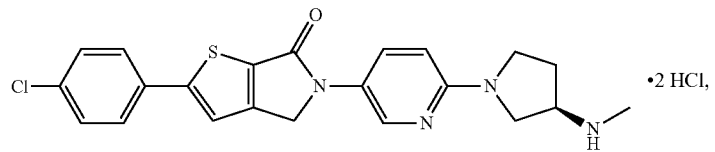
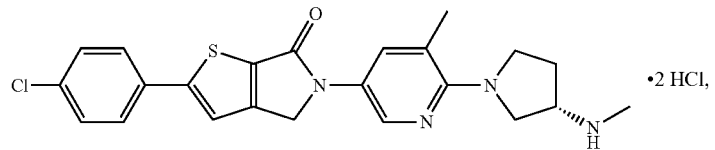
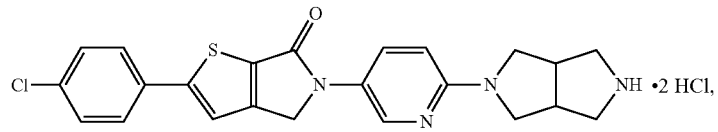
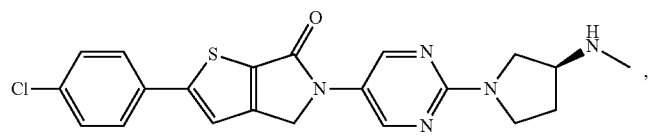
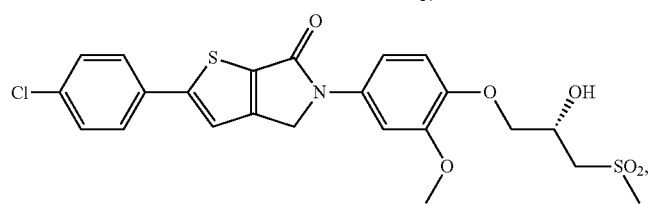
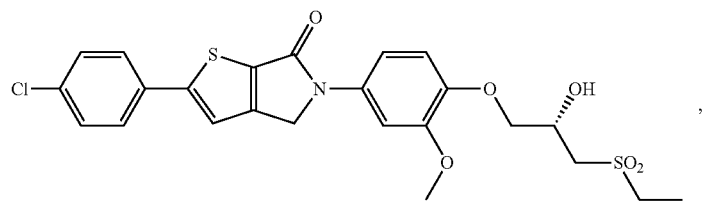

-continued
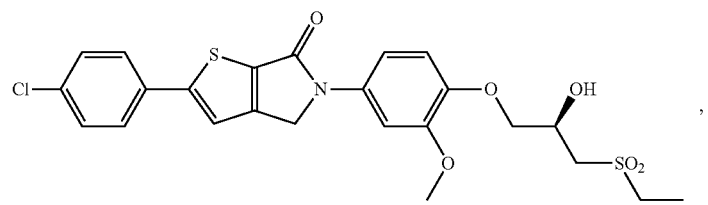
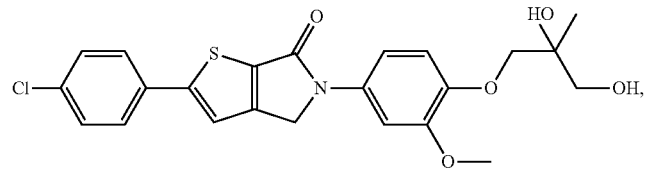
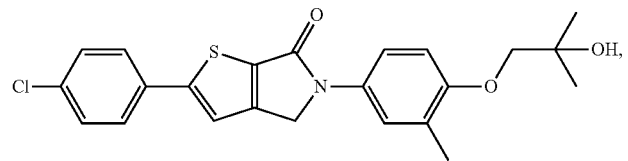
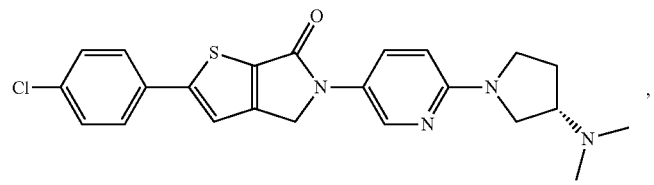
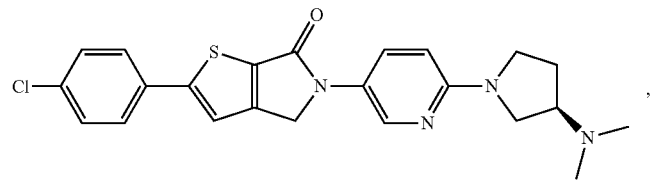
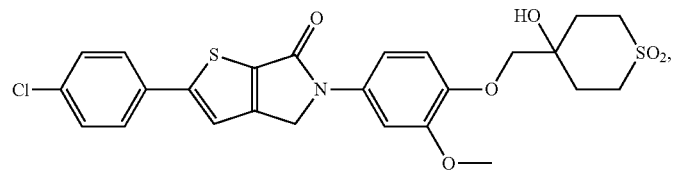
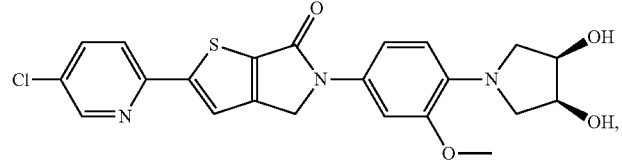
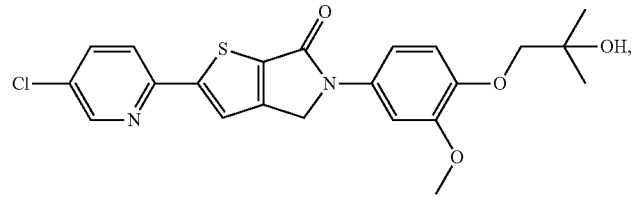
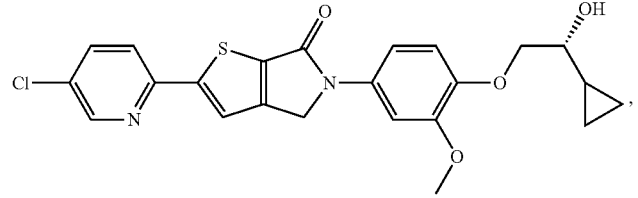

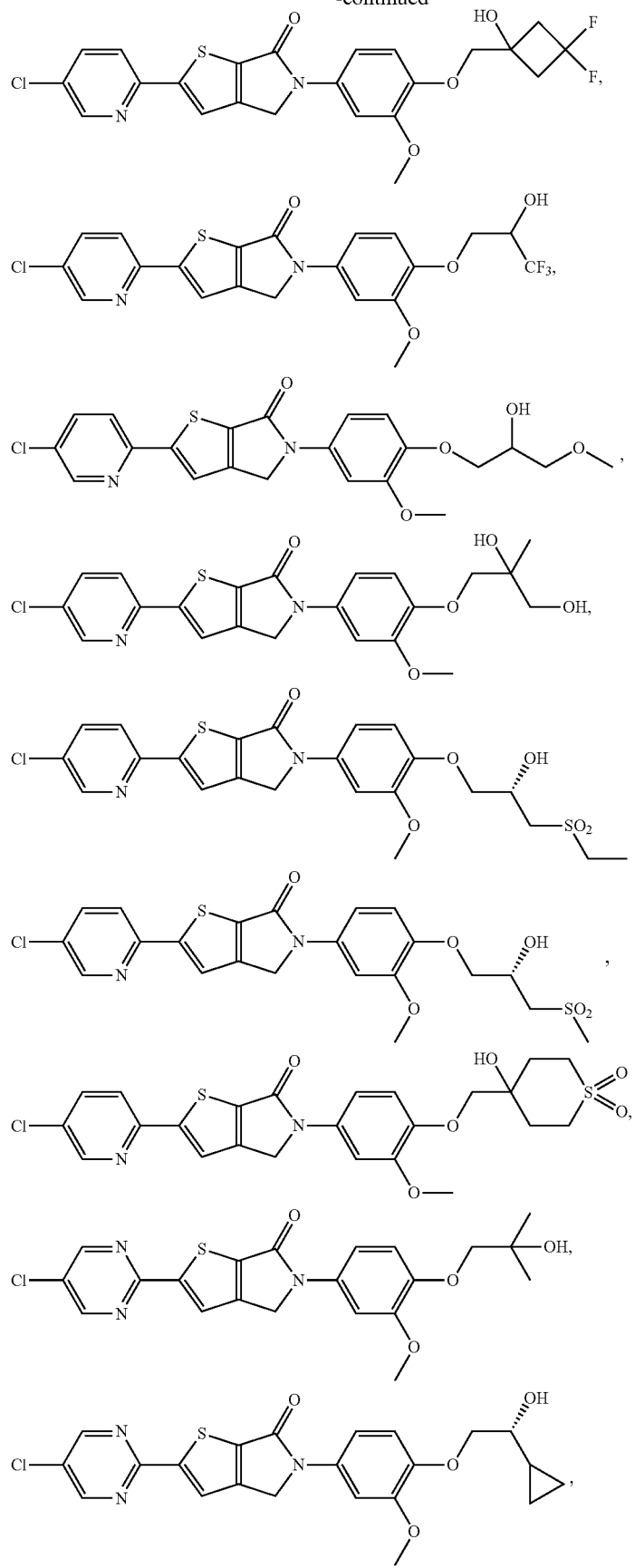

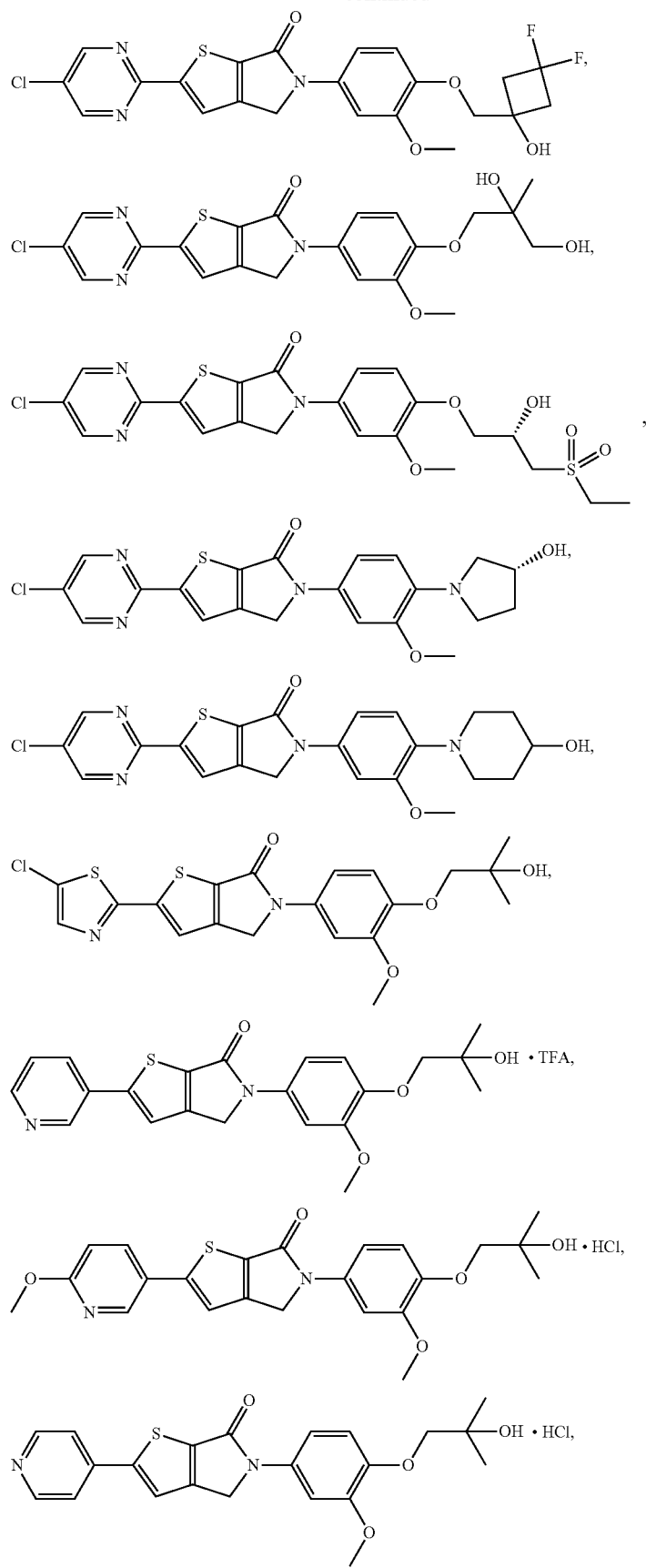

-continued
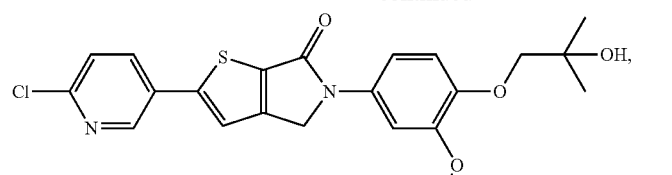
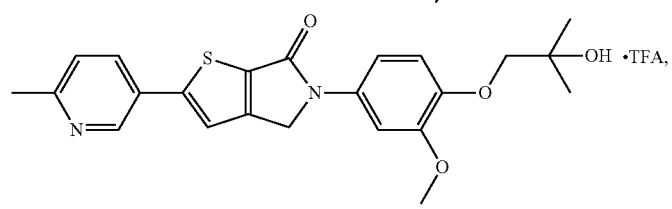
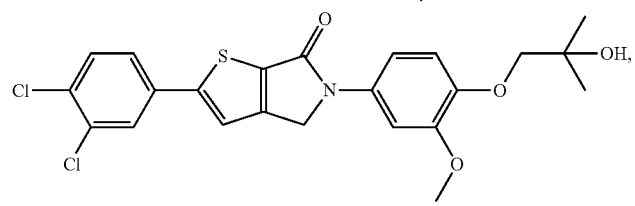
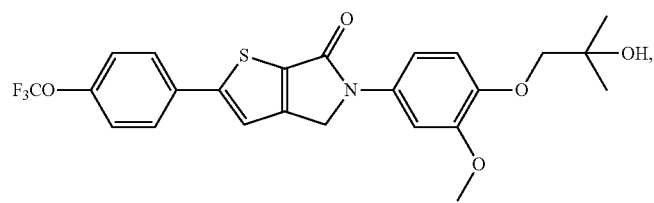
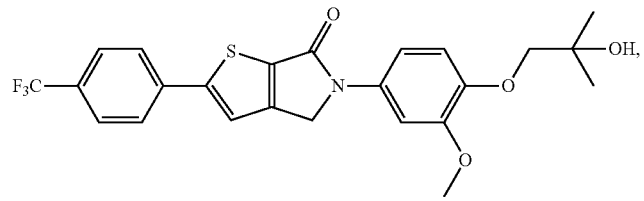
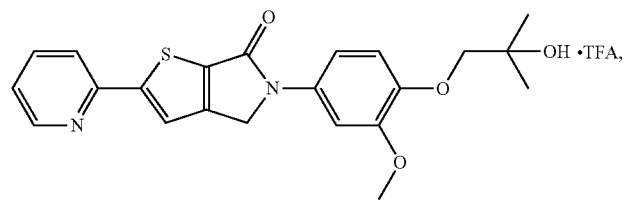
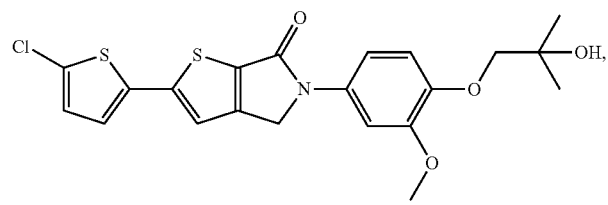
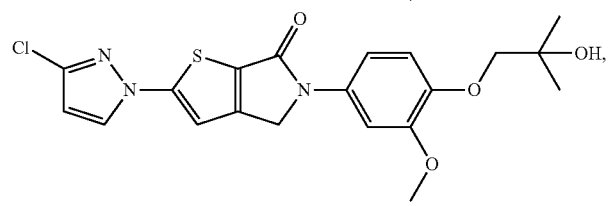

-continued
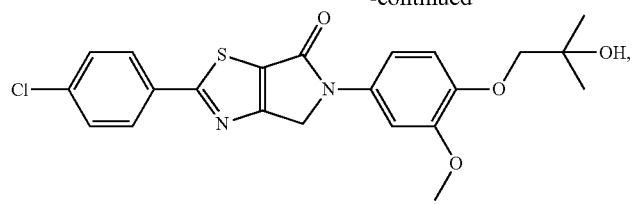
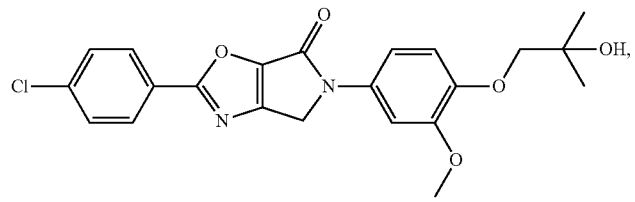
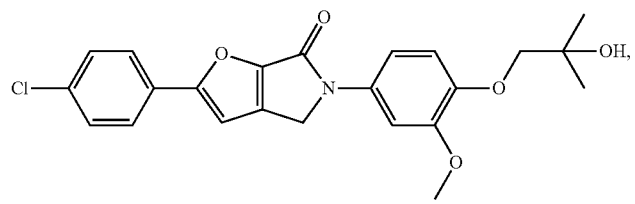
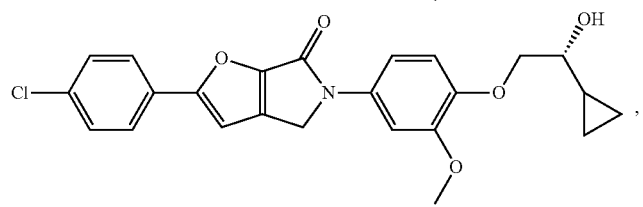
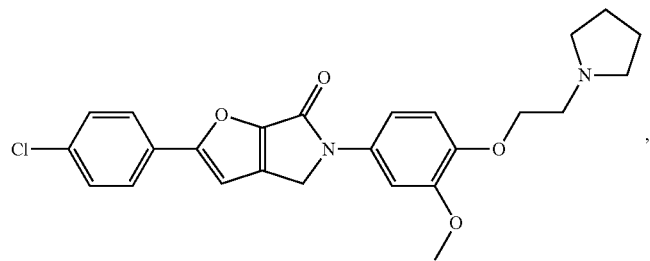
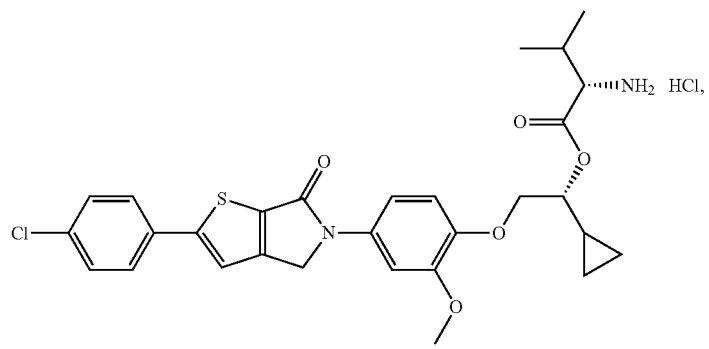
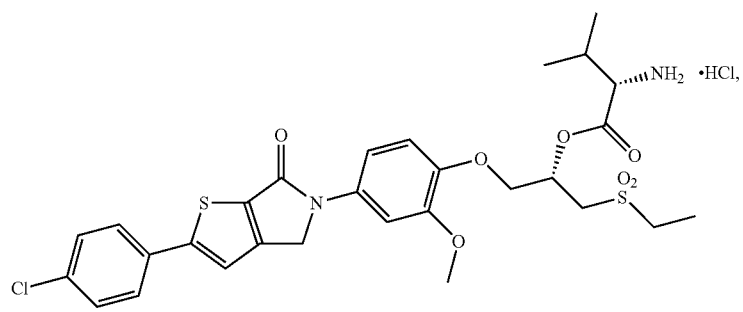

-continued
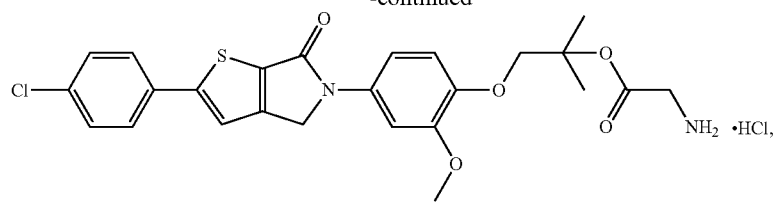
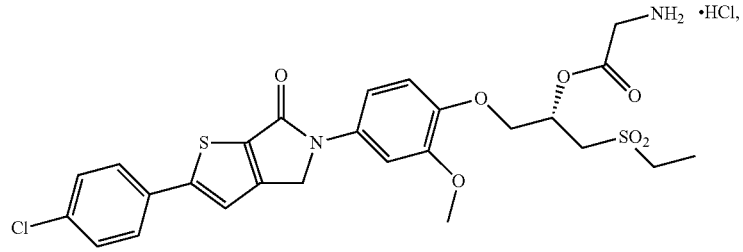
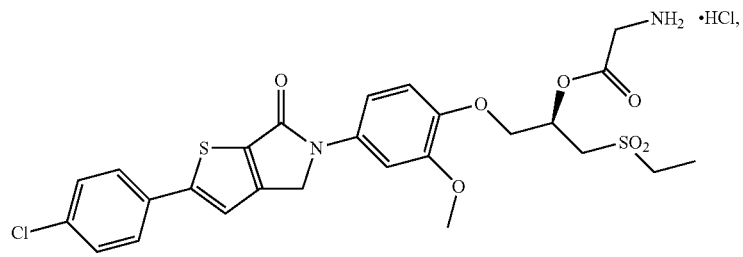
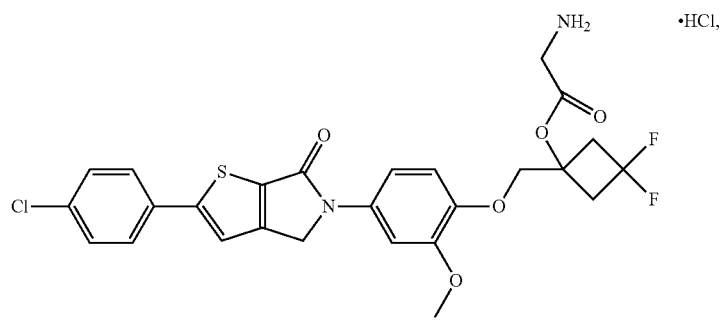
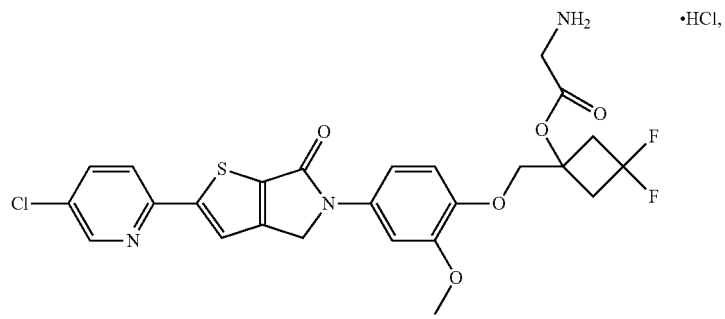
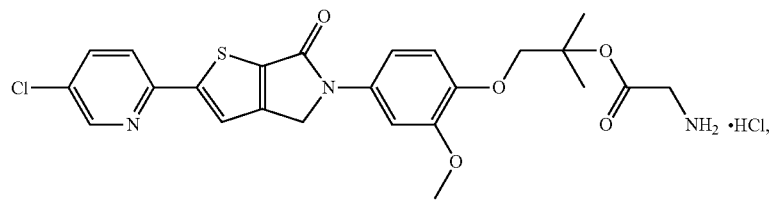
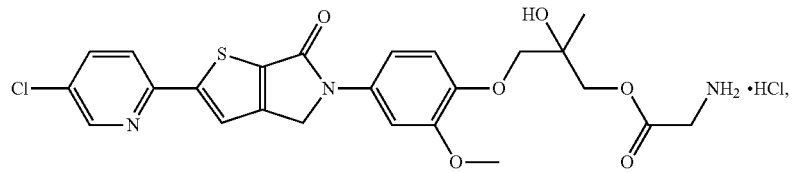

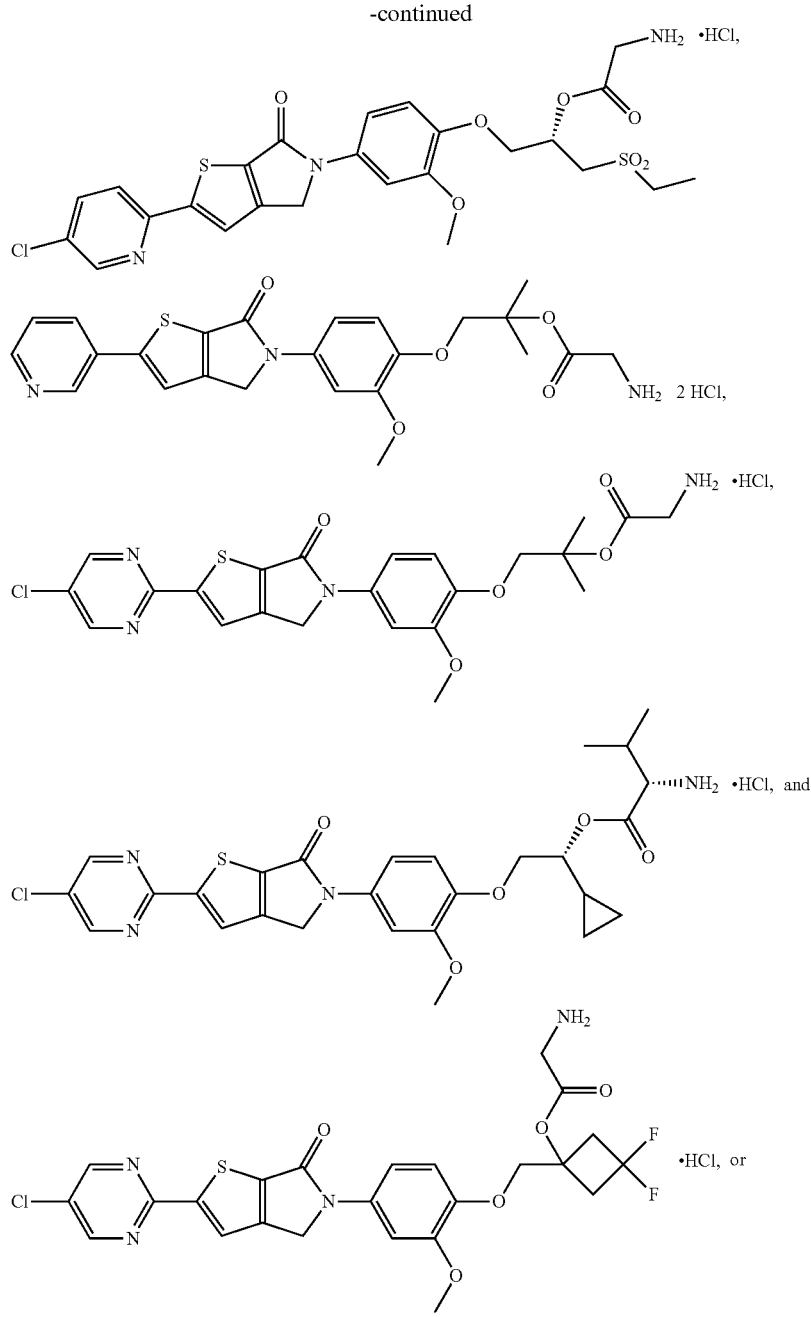
a pharmaceutically acceptable salt of each of the above listed compounds.
9. The compound according to claim 1, wherein the compound is selected from the group consisting of:
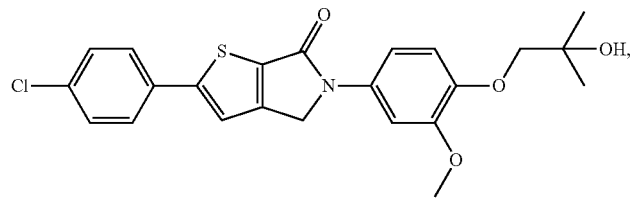

-continued
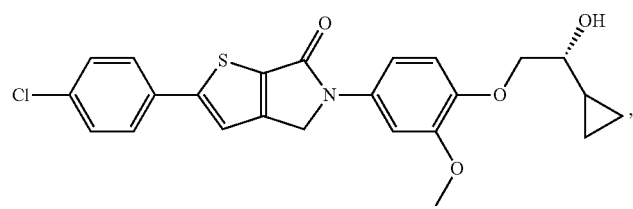
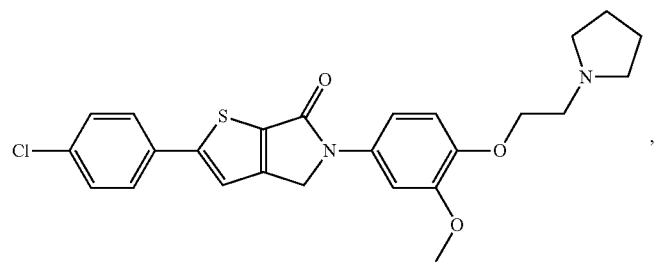
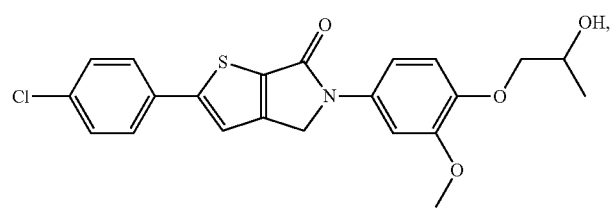
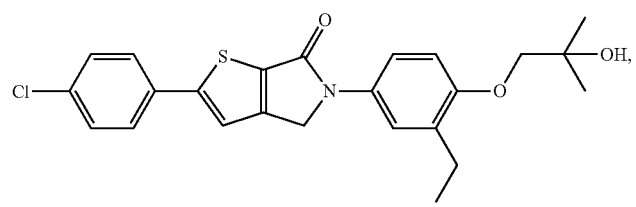
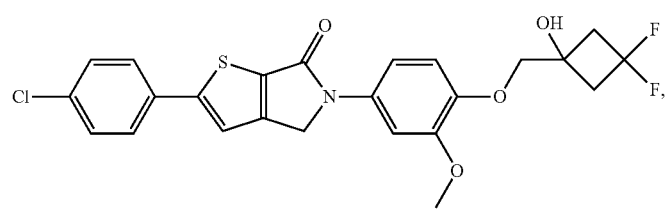
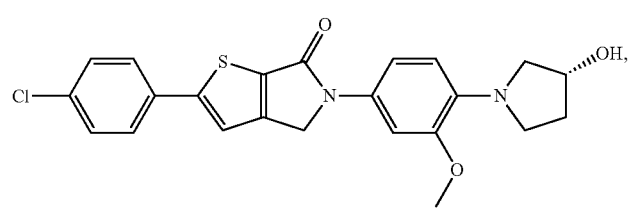
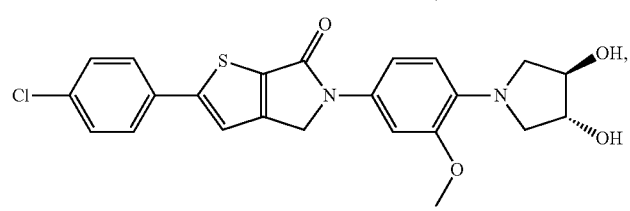
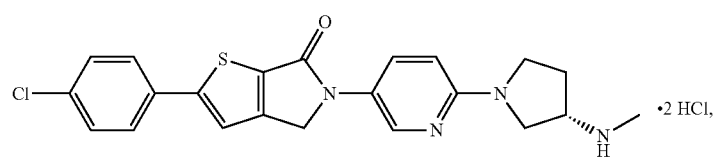

-continued
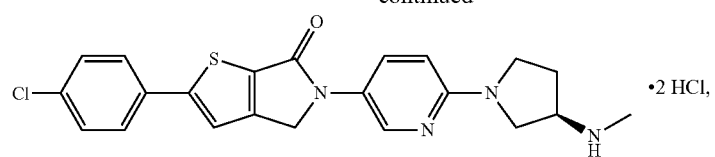 •2 HCl,
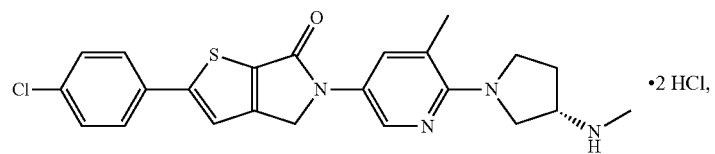 •2 HCl,
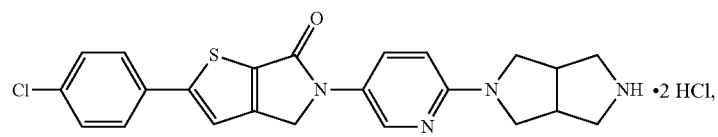 •2 HCl,
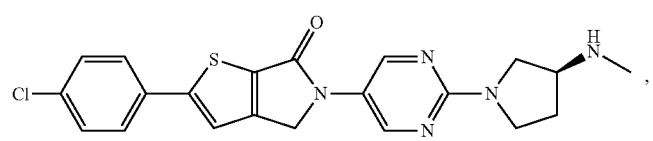,
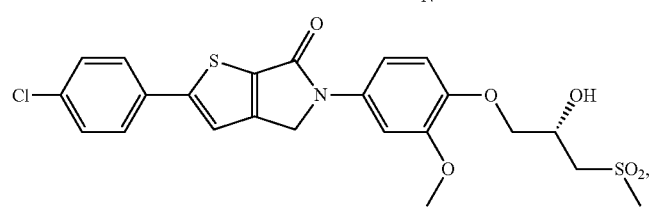
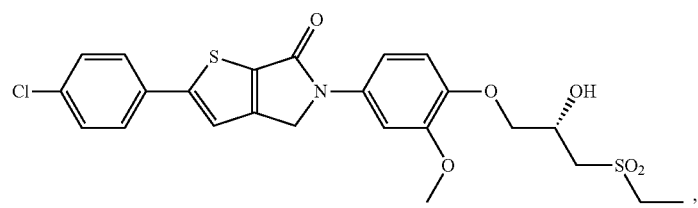,
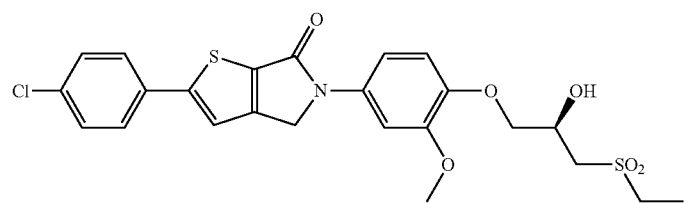,
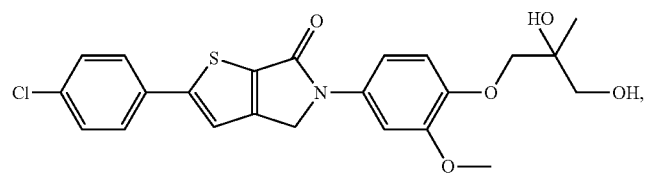,
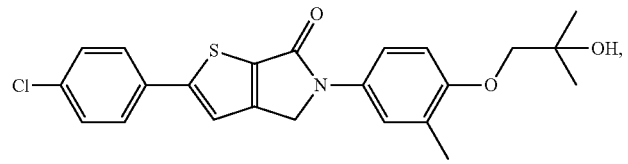,
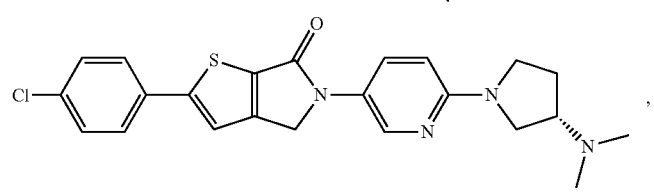,

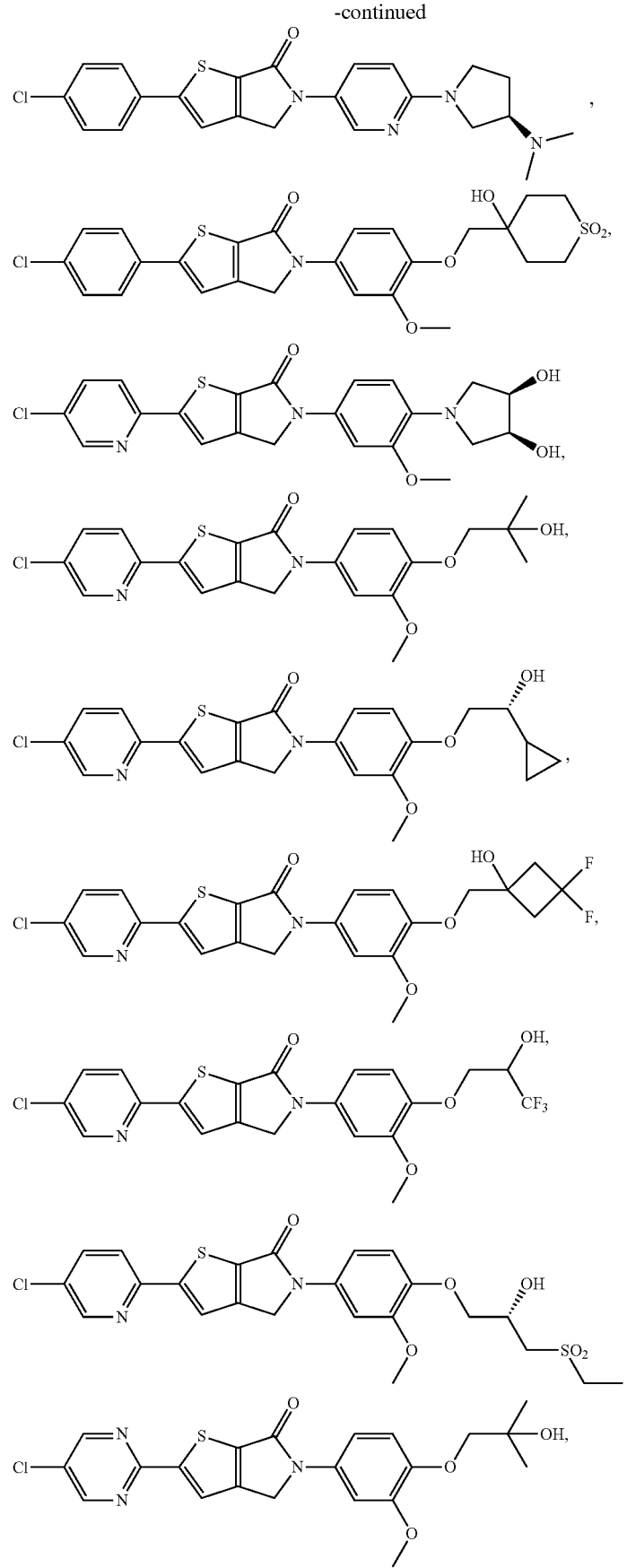

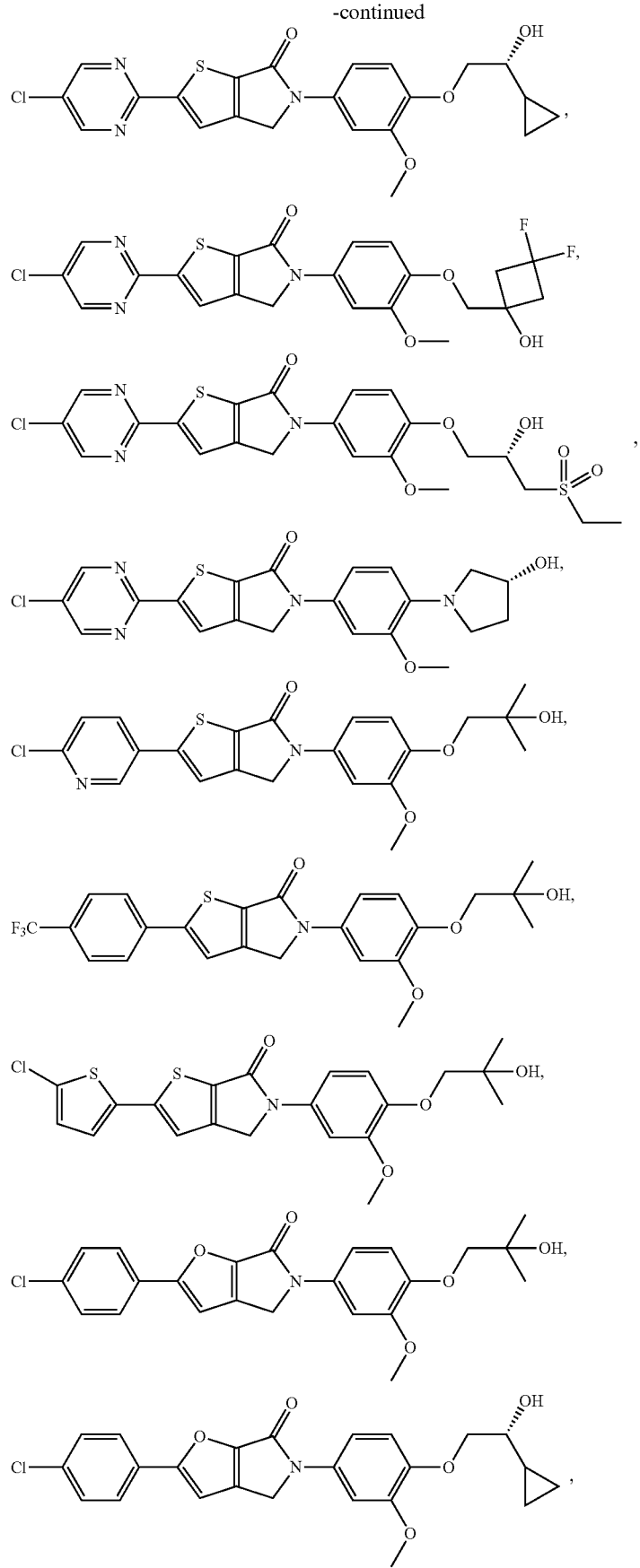

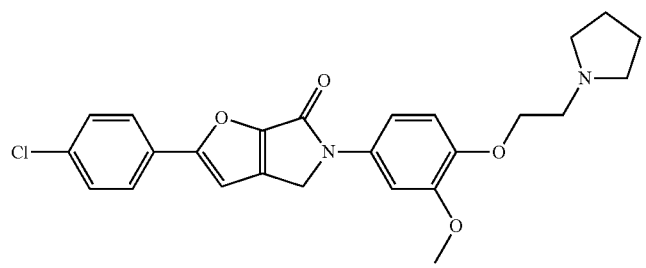
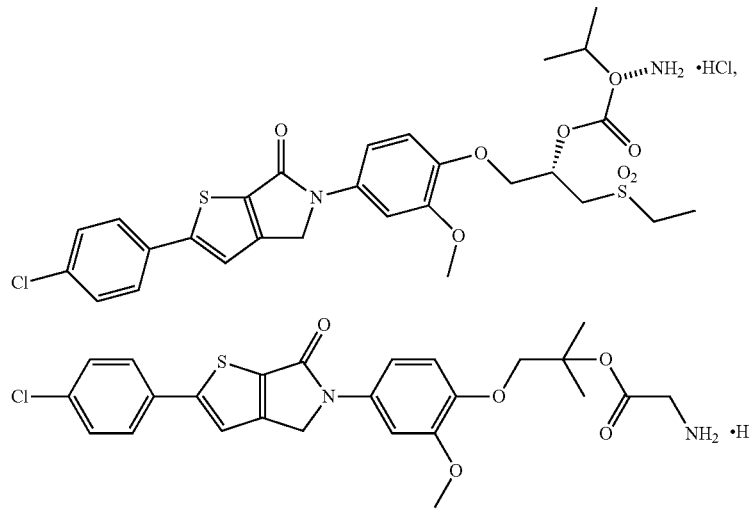
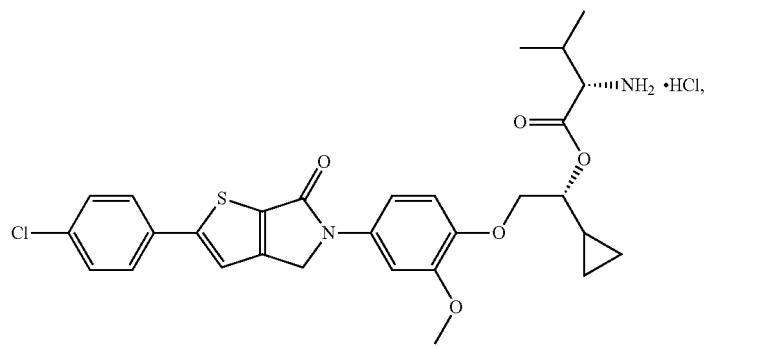
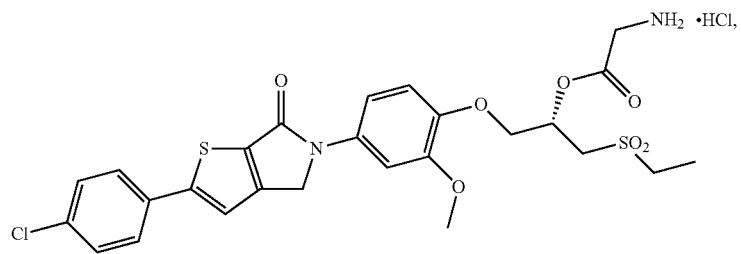
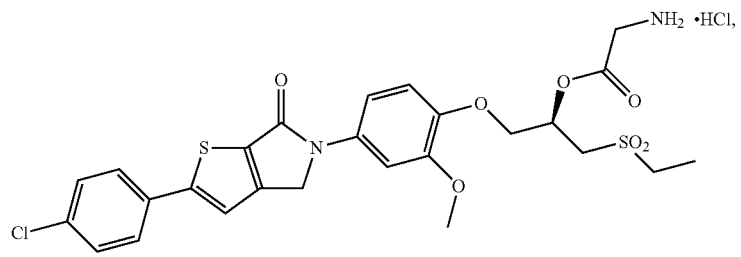

-continued
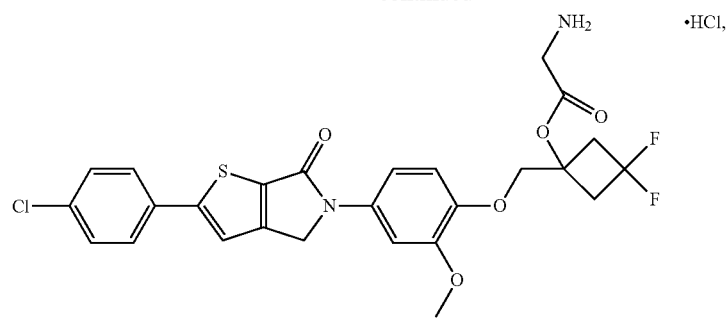
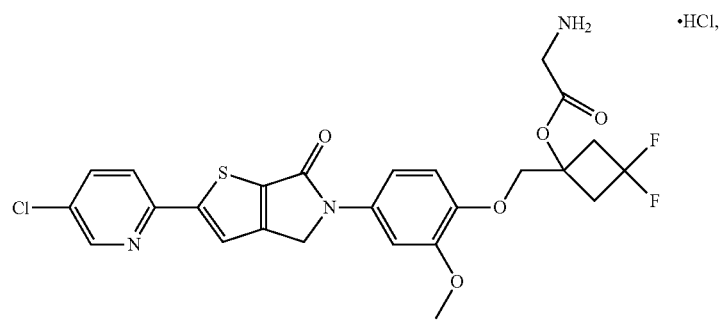
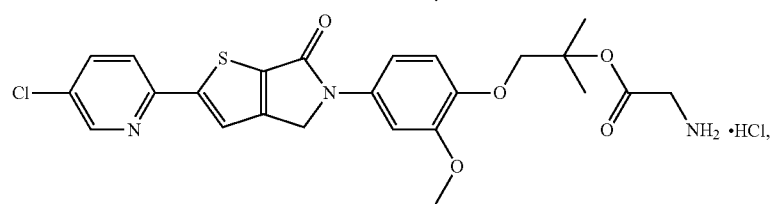
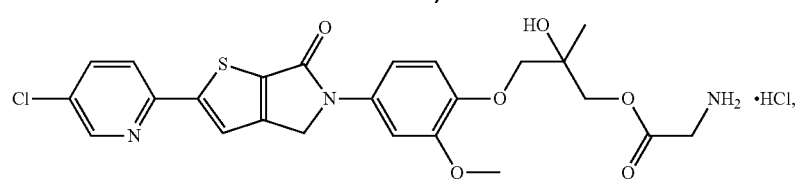
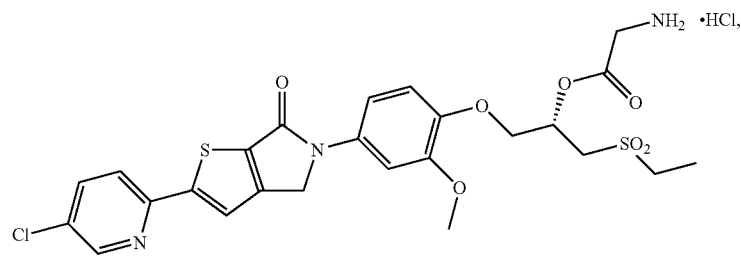
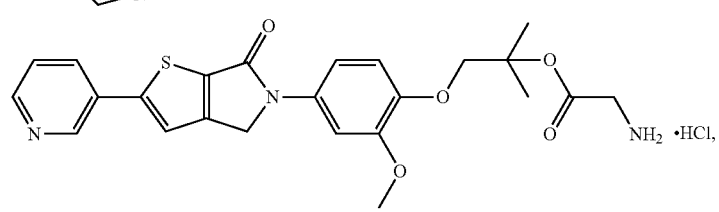
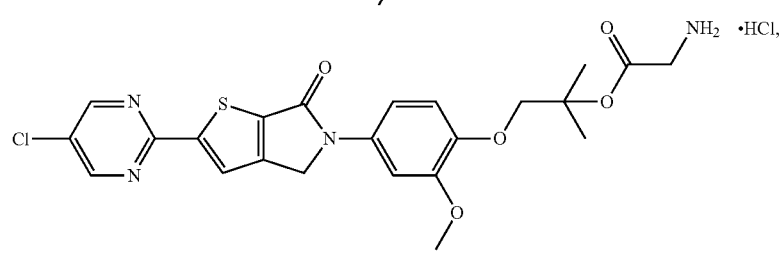

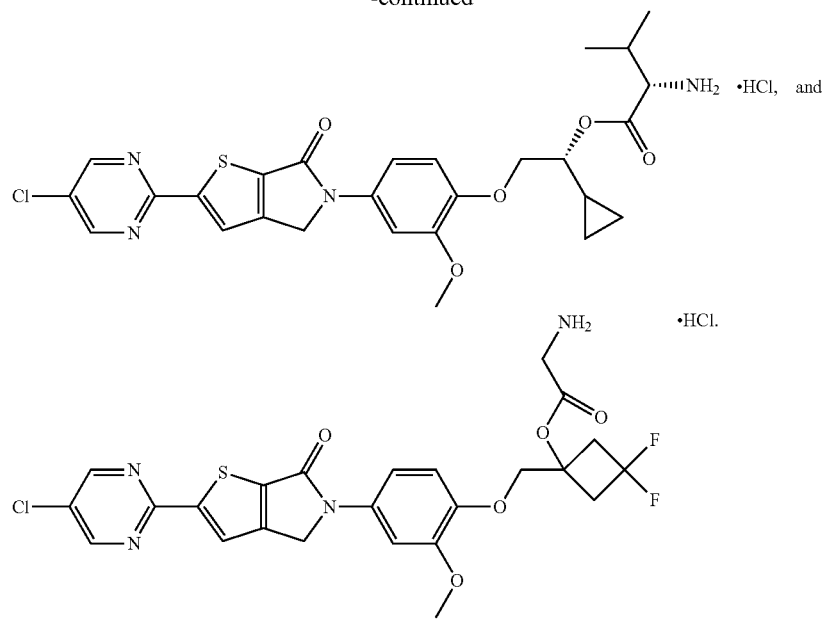

10. A pharmaceutical composition, comprising:
at least one compound according to claim 1; and
at least one pharmaceutically acceptable carrier or diluent, and optionally comprising at least one additional therapeutic agent.

11. A pharmaceutical combination, comprising:
at least one compound according to claim 1; and
at least one additional therapeutic agent which is an anti-obesity agent or an antidiabetic agent.

12. A method for treating obesity comprising administering to a patient in need of such treatment a therapeutically effective amount of a compound according to claim 1.

13. A method for treating diabetes comprising administering to a patient in need of such treatment a therapeutically effective amount of a compound according to claim 1.

* * * * *

UNITED STATES PATENT AND TRADEMARK OFFICE
CERTIFICATE OF CORRECTION

PATENT NO. : 8,344,160 B2
APPLICATION NO. : 13/122833
DATED : January 1, 2013
INVENTOR(S) : Gouhua Zhao et al.

It is certified that error appears in the above-identified patent and that said Letters Patent is hereby corrected as shown below:

In the Claims

Column 122

Line 16, after "$R^1$ is" insert -- 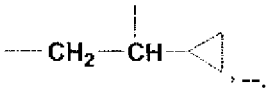 --.

Column 126

Line 65, before "or a bond; or" insert --  --.

Signed and Sealed this
Fourth Day of June, 2013

Teresa Stanek Rea
*Acting Director of the United States Patent and Trademark Office*